US007268135B2

(12) United States Patent
Xiang et al.

(10) Patent No.: US 7,268,135 B2
(45) Date of Patent: Sep. 11, 2007

(54) BIARYL SULFONAMIDES AND METHODS FOR USING SAME

(75) Inventors: Jason Shaoyun Xiang, Winchester, MA (US); Steve Yikkai Tam, Wellesley, MA (US); Yonghan Hu, Burlington, MA (US); Phaik-Eng Sum, Pomona, NY (US); David Brian How, Nyack, NY (US); Darrin William Hopper, New York, NY (US); Matthew Douglas Vera, Royersford, PA (US); Joshua James Sabatini, White Plains, NY (US); Thomas Saltmarsh Rush, III, Lexington, MA (US)

(73) Assignee: Wyeth, Madison, NJ (US)

( * ) Notice: Subject to any disclaimer, the term of this patent is extended or adjusted under 35 U.S.C. 154(b) by 219 days.

(21) Appl. No.: 11/000,711

(22) Filed: Dec. 1, 2004

(65) Prior Publication Data

US 2005/0130973 A1   Jun. 16, 2005

Related U.S. Application Data

(60) Provisional application No. 60/526,883, filed on Dec. 4, 2003.

(51) Int. Cl.
*C07D 217/02* (2006.01)
*A61K 31/50* (2006.01)

(52) U.S. Cl. .................. 514/247; 514/252.1; 514/256; 514/307; 514/310; 514/311; 514/313; 514/352; 514/357; 514/367; 514/370; 514/374; 514/375; 514/406; 514/407; 514/562; 544/224; 544/242; 544/336; 546/147; 546/152; 546/304; 546/341; 548/148; 548/216; 562/430

(58) Field of Classification Search ................ 544/224, 544/242, 336; 546/147, 152, 304, 341; 548/148, 548/216; 562/430; 514/247, 256, 252.1, 514/307, 310, 311, 313, 352, 357, 367, 370, 514/374, 375, 406, 407, 562
See application file for complete search history.

(56) References Cited

FOREIGN PATENT DOCUMENTS

| EP | 0 950 656 A1 | 10/1999 |
| WO | 97/44315 A1 | 11/1997 |
| WO | 00/51993 A2 | 9/2000 |
| WO | 00/51993 A3 | 9/2000 |
| WO | 01/27084 A1 | 4/2001 |

OTHER PUBLICATIONS

U.S. Appl. No. 11/001,589, filed Dec. 1, 2004, Levin et al.
Tamura, Y. et al., "Highly Selective and Orally Active Inhibitors of Type IV Collagenase (MMP-9 and MMP-2): *N*-Sulfonylamino Acid Derivatives," *J Med Chem*, 1998, 41:640-649.
Tang, B. L., "ADAMTS: a novel family of extracellular matrix proteases,", *Int J Biochem Cell Biol*, 2001, 33:33-44.
Abbaszade I. et al., "Cloning and Characterization of ADAMTS11, an Aggrecanase from the ADAMTS family," *J Biol Chem*, Aug. 13, 1999, 274(33): 23443-23450.
Colige, A. et al., "cDNA cloning and expression of bovine procollagen I N-proteinase: A new member of the superfamily of zinc-metalloproteinases with binding sites for cells and other matrix components," *Proc Natl Acad Sci USA*, Mar. 1997, 94, 2374-2379.
Vázquez F. et al., "METH-1, a Human Orgholog of ADAMTS-1, and METH-2 Are Members of a New Family of Proteins with Angio-inhibitory Activity," *J Biol Chem*, Aug. 13, 1999, 274(33): 23349-23357.
Masui T., et al., "An Alu-linked Repetitive Sequence Corresponding to 280 Amino Acids Is Expressed in a Novel Bovine Protein, but Not in Its Human Homologue," *J Biol Chem*, Jan. 31, 1997, 272(5), 2801-2807.
Kuno, K. et al., "Molecular Cloning of a Gene Encoding a New Type of Metalloproteinase-disintegrin Family Protein with Thrombospondin Motifs as an Inflammation Associated Gene," *J Biol Chem*, Jan. 3, 1997, 272(1), 556-562.
Bundgaard, H. (ed.), *Design of Prodrugs*, Elsevier (1985), Ch. 1 (pp. 1-92), Ch. 4 (pp. 157-176), Ch. 5 (pp. 177-198), and Ch. 6 (pp. 199-241).
Widder, et al. (ed.), *Methods in Enzymology*, vol. 112, Academic Press (1985), pp. 309-396.
Krogsgaard-Larsen, et al., (ed). *Design and Application of Prodrugs, Textbook of Drug Design and Development*, Chapter 5, 113-191, 1991.
Bundgaard, H., "Means to enhance penetration; Prodrugs as a means to improve the delivery of peptide drugs," *Advanced Drug Deliver Reviews*, 1992, 8, 1-38.
Bundgaard, H. et al., "Glycolamide Esters as Biolabile Prodrugs of Carboxylic Acid Agents: Synthesis, Stability, Bioconversion, and Physicochemical Properties," *J. of Pharmaceutical Sciences*, Apr. 1988, 77(4):285-298.
Higuchi and Stella (eds.), *Prodrugs as Novel Drug Delivery Systems*, American Chemical Society (1975), pp. 1-115 and 196-223.
Laemmli, U. K., "Cleavage of Structural Proteins during the Assembly of the Head of Bacteriophage T4," *Nature*, Aug. 15, 1970, 227:680-685.
Oaklet, B. R. et al., "A Simplified Ultrasensitive Silver Stain for Detecting Proteins in Polyacrylamide Gels," *Anal. Biochem*, 1980, 105:361-363.
Towbin, H. et al., "Electrophoretic transfer of proteins from polyacrylamide gels to nitrocellulose sheets: Procedure and some applications," *Proc. Natl. Acad. Sci. USA*, Sep. 1979, 76(9), 4350-4354.
Hughes, C. E. et al., "Monoclonal antibodies that specifically recognize neoepitope sequences generated by 'aggrecanase' and matrix metalloproteinase cleavage of aggrecan: application to catabolism in situ and in vitro," *Biochem J*, Feb. 1, 1995, 305(3), 799-804.
Romero, D. L. et al, "Discovery, Synthesis, and Bioactivity of Bis(heteroaryl)piperazines. 1. A Novel Class of Non-Nucleoside HIV-1 Reverse Transcriptase Inhibitors," *J. Med. Chem*. 1994, 37, 999-1014.

(Continued)

*Primary Examiner*—Zinna N. Davis
(74) *Attorney, Agent, or Firm*—Woodcock Washburn LLP

(57) ABSTRACT

The present invention relates to biaryl sulfonamides and their use as, for example, metalloproteinase inhibitors.

11 Claims, No Drawings

OTHER PUBLICATIONS

Emmott, P. et al., "Preparation of Some Naphthofurans," *J. Chem. Soc.* (Jul. 1957) pp. 3144-3148.

Evans, D. A. et al., "Synthesis of Diaryl Ethers through the Copper-Promoted Arylation of Phenols with Arylboronic Acids. An Expedient Synthesis of Thyroxine," *Tetrahedron Lett.*, May 7, 1998, 39(19):2937-2940.

Bencze, W. L. et. al, "The Absolute Configuration of a Hypolipidemic 1-Aryl Tetralin, Nafenopin," *Tetrahedron* 1970, 26:5407-5414.

Werner, A. W. et al., "Porphyrins with Four Azole Substituents in meso Positions: X-Ray Crystal Structure of Meso-tetrakis-(1-benzylpyrazol-4-yl)-porphyrin at 200 K," *Tetrahedron*, Apr. 17, 1995, 51(16): 4779-4800.

Burtner, R.R. et al., "Antispasmodics. I. Basic Esters of Some Arylacetic Acids," *J. Am. Chem. Soc.*, 1943, 65:262-267.

Abramov, M. A. et al., "Nucleophilic Intramolecular Cyclization Reactions of Alkylnechalcogenolates," *Tetrahedron*, Jun. 9, 2000, 56(24): 3933-3940.

Knight, C.G. et al., "A novel-coumarin-labelled peptide for sensitive continuous assays of the matrix metalloproteinases," *FEBS Lett.* (Jan. 1992) 296(3):263-266.

*Remington's Pharmaceutical Sciences*, 17th Ed., Gennaro, A. R. (Ed.), Mack Publishing Company, Easton, PA (1985) pp. 1409-1677.

BIARYL SULFONAMIDES AND METHODS FOR USING SAME

CROSS REFERENCE TO RELATED APPLICATIONS

This application claims benefit to U.S. Provisional Application No. 60/526,883, filed Dec. 4, 2003, the entirety of which is incorporated by reference herein.

FIELD OF THE INVENTION

The present invention relates to biaryl sulfonamides and their use as, for example, novel metalloproteinase inhibitors.

BACKGROUND OF THE INVENTION

Metalloproteinases, including matrix metalloproteinases and aggrecanases, are known to have a role in the breakdown of connective tissue. Matrix metalloproteinases ("MMPs") constitute a superfamily of proteolytic enzymes that are genetically related and capable of degrading almost all the constituents of extracellular matrix and basement membrane that restrict cell movement. Aggrecanases are members of the ADAMTS (A disintegrin and metalloproteinase with thrombospondin motifs) family of proteins. Aggrecanase-1 and aggrecanase-2 have been designated ADAMTS-4 and ADAMTS-5, respectively (Tang B L, *Int J Biochem Cell Biol* 2001, 33, 33–44).

The ADAMTS family is involved in cleaving aggrecan, a cartilage component also known as the large aggregating chondroitin sulphate proteoglycan (Abbaszade I et al., J Biol Chem 1999, 274, 23443–23450), procollagen processing (Colige A et al., Proc Natl Acad Sci USA 1997, 94, 2374–2379), angiogenesis (Vazquez F et al., J Biol Chem 1999, 274, 23349–23357), inflammation (Kuno K et al., J Biol Chem 1997, 272, 556–562) and tumor invasion (Masui T., et al., J Biol Chem 1997, 272, 556–562). MMPs have been shown to cleave aggrecan as well.

The loss of aggrecan has been implicated in the degradation of articular cartilage in arthritic diseases, for example osteoarthritis is a debilitating disease which affects at least 30 million Americans. Degradation of articular cartilage and the resulting chronic pain can severely reduce quality of life. An early and important characteristic of the osteoarthritic process is loss of aggrecan from the extracellular matrix, resulting in deficiencies in the biomechanical characteristics of the cartilage. Likewise, MMPs and aggrecanases are known to play a role in many disorders in which extracellular protein degradation or destruction occurs, such as cancer, asthma, chronic obstructive pulmonary disease ("COPD"), atherosclerosis, age-related macular degeneration, myocardial infarction, corneal ulceration and other ocular surface diseases, hepatitis, aortic aneurysms, tendonitis, central nervous system diseases, abnormal wound healing, angiogenesis, restenosis, cirrhosis, multiple sclerosis, glomerulonephritis, graft versus host disease, diabetes, inflammatory bowel disease, shock, invertebral disc degeneration, stroke, osteopenia, and periodontal diseases.

Therefore, metalloproteinase inhibitors are needed, including inhibitors of MMPs and aggrecanases.

SUMMARY OF THE INVENTION

In one embodiment, the present invention provides novel comprises biaryl sulfonamide compounds. Preferred compounds of the invention are those of the formula I:

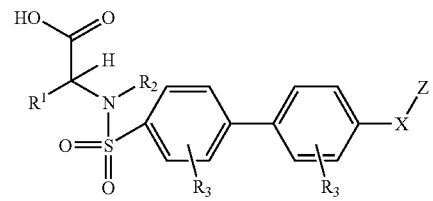

wherein:
$R^1$ is H or C1–C6 alkyl;
$R^2$ is H, C1–C6 alkyl, $(CH_2)_n R^{2'}$, phenyl, or benzyl;
n is 0–6;
$R^{2'}$ is aryl, heteroaryl, cycloalkyl, or heterocycloalkyl;
$R^3$ is, independently with respect to each occurrence, H, halogen, $OC(halogen)_3$, $C(halogen)_3$, alkoxy, or C1–C6 alkyl;
X is selected from $CH_2O$, $OCH_2$, $C(R^3)=C(R^3)$, $C(R^3)_2-C(R^3)_2$, $CH_2NHC(=O)$, $O(C=O)NH$, O, $C(=O)CH_2$, $SO_2CH_2C(=O)NH$, $SO_2NH$, $OC(=O)$, $CH_2S(O)$, and $CH_2S(O)_2$; and
Z is at least one aryl or heteroaryl moiety.

In another aspect, the present invention provides methods for using biaryl sulfonamide compounds to modulate and, preferably, inhibit metalloproteinases. Preferred methods involve in vitro and in vivo contacting of the metalloproteinase with a biaryl sulfonamide. Preferred methods of this type are ones in which the activity of the metalloproteinase is determined before or after such contacting and, optionally, the determination is used to assess the extent to which the compound modulates the activity of the enzyme.

DETAILED DESCRIPTION OF THE INVENTION

In accordance with the present invention it has been discovered that biaryl sulfonamide compounds find use in inhibiting metalloproteinases. Such compounds are therefore useful in the treatment of cancer, osteoarthritis, rheumatoid arthritis, asthma, COPD, atherosclerosis, age-related macular degeneration, myocardial infarction, corneal ulceration and other ocular surface diseases, hepatitis, aortic aneurysms, tendonitis, central nervous system diseases, abnormal wound healing, angiogenesis, restenosis, cirrhosis, multiple sclerosis, glomerulonephritis, graft versus host disease, diabetes, inflammatory bowel disease, shock, invertebral disc degeneration, stroke, osteopenia, and periodontal diseases. The metalloproteinase is preferably Aggrecanase-1 (also known as ADAMTS4, and abbreviated herein as "Agg-1") or MMP-13.

In one embodiment, the biaryl sulfonamide compound is of the formula I:

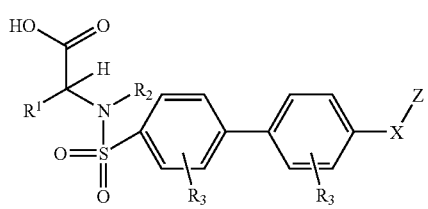

wherein:

R¹ is H or C1–C6 alkyl;

R² is H, C1–C6 alkyl, $(CH_2)_nR^{2'}$, phenyl, or benzyl;

n is 0–6;

$R^{2'}$ is aryl, heteroaryl, cycloalkyl, or heterocycloalkyl;

R³ is, independently with respect to each occurrence, H, halogen, $OC(halogen)_3$, $C(halogen)_3$, alkoxy, or C1–C6 alkyl;

X is selected from $CH_2O$, $OCH_2$, $C(R^3)=C(R^3)$, $C(R^3)_2$—$C(R^3)_2$, $CH_2NHC(=O)$, $O(C=O)NH$, O, $C(=O)CH_2$, $SO_2CH_2C(=O)NH$, $SO_2NH$, $OC(=O)$, $CH_2S(O)$, and $CH_2S(O)_2S(O)_2$; and Z is at least one aryl or heteroaryl moiety.

It has been discovered that the R-configuration isomer at the alpha carbon is a better inhibitor of Agg-1, whereas both enantiomers are effective MMP inhibitors.

It is understood that the foregoing definition includes pharmaceutically acceptable salts and pro-drugs of these compounds.

In one embodiment, Z is pyridine, pyrimidine, pyrazine, pyridazine, phenyl, naphthalene, furan, thiophene, pyrrole, pyrazole, imidazole, oxazole, isoxazole, thiazole, benzothiazole, quinoline, or isoquinoline, or

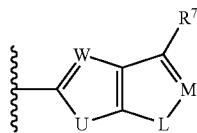

wherein:

U is selected from S, O, $C(R^3)=C(R^3)$, $C(R^3)=N$, and $N(R^4)$;

W is selected from $C(R^3)$, and N;

M is selected from $C(R^3)$, and N;

L is selected from S, O, $C(R^3)=C(R^3)$, $C(R^3)=N$, and $N(R^4)$;

R⁴ and R⁵ are, independently with respect to each occurrence, a bond to the other, H, C1–C6 alkyl, or phenyl;

R⁷ is selected from a bond to R³, H, halogen, $C(halogen)_3$, $NR^4R^5$, $N[(CH_2)_2]_2O$, $N[(CH_2)_2]_2NR^4$, $NHSO_2R^4$, $NR^4C(=O)R^5$, $NHC(=O)OR^4$, $NO_2$, $SO_2NR^4R^5$, $SO_2R^4$, $OR^4$, $C(=O)R^4$, $COOR^4$, $CONR^4R^5$, CN, phenyl, heteroaryl, C1-C6 alkyl, C2–C6 alkenyl, or C2–C6 alkynyl; and R⁸ is selected from H, phenyl, heteroaryl, and C1–C6 alkyl.

When R⁷ is substituted, it is preferably substituted with $NR^4R^5$, $N[(CH_2)_2]_2O$, $N[(CH_2)_2]_2NR^4$, $NHSO_2R^4$, $NR^4C(=O)R^5$, $NHC(=O)OR^4$, $NO_2$, $SO_2NR^4R^5$, $SO_2R^4$, $C(=O)R^4$, $C(=O)R^4$, $COOR^4$, $CONR^4R^5$, CN, phenyl, or heteroaryl.

R⁸, when substituted, is preferably substituted with $NR^4R^5$, $N[(CH_2)_2]_2O$, $N[(CH_2)_2]_2NR^4$, $NR^4SO_2R^5$, $NR^4C(=O)R^5$, $NHC(=O)OR^4$, $NO_2$, $SO_2NR^4R^5$, $SO_2R^4$, $C(=O)R^4$, $COOR^4$, $CONR^4R^5$, CN, phenyl, or heteroaryl.

Preferred among the above noted R¹ groups are H and branched alkyl, and more preferably isopropyl.

Preferred among the above noted R³ groups are halogen, $CF_3$, $OCH_3$, and $CH_3$.

Preferred among the above noted X groups are $CH_2O$, $OCH_2$, $C(R^3)=C(R^3)$, and $CH_2NHC(=O)$.

Preferred among the above noted R⁷ groups are $CH_3$, ethyl, isopropyl, $CF_3$, CN, and $OCH_3$.

Preferred among the above noted R⁸ groups are $CH_3$, phenyl, and benzyl.

In one embodiment, X is $CH_2O$, and Z is aryl or heteroaryl, preferably bicyclic.

In one embodiment, X is $OCH_2$, and Z is aryl or heteroaryl, preferably bicyclic.

In one embodiment, X is $C(R^3)=C(R^3)$, and Z is aryl or heteroaryl, preferably bicyclic. More preferably, X is a trans carbon-carbon double bond.

In one embodiment, X is $C(R^3)_2$—$C(R^3)_2$, Z is aryl or heteroaryl, preferably bicyclic.

In one embodiment, X is $CH_2NHCO$, Z is aryl or heteroaryl, preferably bicyclic.

In one embodiment, X is carbamate O—CO—NH, Z is aryl or heteroaryl, preferably bicyclic.

In one embodiment, X is $CO_2$, Z is aryl or heteroaryl, preferably bicyclic.

In one embodiment, X is O, Z is aryl or heteroaryl, preferably bicyclic.

In one embodiment, X is $C(=O)CH_2$, Z is aryl or heteroaryl, preferably bicyclic.

In one embodiment, X is $SO_2CH_2$, Z is aryl or heteroaryl, preferably bicyclic.

In one embodiment, X is $OCH_2$, Z is aryl or heteroaryl, preferably bicyclic. Preferably, if substituted, the substitution is on the second phenyl ring.

In one embodiment, X is $OCH_2$, Z is aryl or heteroaryl, preferably bicyclic. Preferably, if substituted, the substitution is on the first phenyl ring.

In one embodiment, X is $CH_2OCH_2$, Z is aryl or heteroaryl, preferably bicyclic. Preferably, if substituted, the substitution is on the first phenyl ring.

The term "alkyl", as used herein, whether used alone or as part of another group, refers to a substituted or unsubstituted aliphatic hydrocarbon chain and includes, but is not limited to, straight and branched chains containing from 1 to 12 carbon atoms, preferably 1 to 6 carbon atoms, unless explicitly specified otherwise. For example, methyl, ethyl, propyl, isopropyl, butyl, i-butyl and t-butyl are encompassed by the term "alkyl." C1–C6 alkyl includes straight and branched chain aliphatic groups having from 1 to 6 carbons. Specifically included within the definition of "alkyl" are those aliphatic hydrocarbon chains that are optionally substituted.

The carbon number as used in the definitions herein refers to carbon backbone and carbon branching, but does not include carbon atoms of the substituents, such as alkoxy substitutions and the like.

The term "alkenyl", as used herein, whether used alone or as part of another group, refers to a substituted or unsubstituted aliphatic hydrocarbon chain and includes, but is not limited to, straight and branched chains having 2 to 8 carbon atoms and containing at least one double bond. Preferably, the alkenyl moiety has 1 or 2 double bonds. Such alkenyl moieties may exist in the E or Z conformations and the compounds of this invention include both conformations. C2–C6 alkenyl includes a 1 to 6 carbon straight or branched chain having at least one carbon-carbon double bond. Specifically included within the definition of "alkenyl" are those aliphatic hydrocarbon chains that are optionally substituted. Heteroatoms, such as O, S or N—R1, attached to an alkenyl should not be attached to a carbon atom that is bonded to a double bond.

The term "alkynyl" refers to a hydrocarbon moiety containing at least one carbon-carbon triple bond. C2–C6 alkynyl includes a 1 to 6 carbon straight or branched chain having at least one carbon-carbon triple bond.

The term "cycloalkyl" a monocyclic, bicyclic, tricyclic, fused, bridged, or spiro monovalent saturated hydrocarbon moiety, wherein the carbon atoms are located inside or outside of the ring system. Any suitable ring position of the cycloalkyl moiety may be covalently linked to the defined chemical structure. Examples of cycloalkyl moieties include, but are not limited to, chemical groups such as cyclopropyl, cyclopropylmethyl, cyclobutyl, cyclopentyl, cyclohexyl, cyclohexylmethyl, cyclohexylethyl, cycloheptyl, norbornyl, adamantyl, spiro[4.5]decanyl, and homologs, isomers, and the like. C3–C6 cycloalkyl includes monocyclic, saturated rings of 3 to 6 carbons, optionally substituted with $R^3$.

"Aryl" refers to an unsaturated carbon ring, and may be fused with a carbocyclic or heterocyclic ring at any possible position.

"Heteroaryl" refers to a 5 to 6 membered aryl heterocyclic ring which contains from 1 to 3 heteroatoms selected from the group consisting of oxygen, nitrogen, and sulfur atoms in the ring and may be fused with a carbocyclic or heterocyclic ring at any possible position.

"Heterocycloalkyl" refers to a 5 to 7-membered saturated ring containing carbon atoms and from 1 to 2 heteroatoms selected from N, O, and S.

The term "phenyl", as used herein, whether used alone or as part of another group, refers to a substituted or unsubstituted phenyl group.

An optionally substituted moiety may be substituted with one or more substituents. Suitable optionally substituents may be selected independently from H, halogen, C1–C6 alkyl, C2–C6 alkenyl, C2–C6 alkynyl, $NR^4R^5$, $N[(CH_2)_2]_2O$, $N[(CH_2)_2]_2NR^4$, $NHSO_2R^4$, $NR^4C(=O)R^5$, $NHC(=O)OR^4$, $NO_2$, $SO_2NR^4R^5$, $SO_2R^4$, $OR^4$, $C(=O)R^4$, $COOR^4$, $CONR^4R^5$, and CN.

When such moieties are substituted, for example, they may typically be mono-, di-, tri- or persubstituted. Examples for a halogen substituent include 1-bromo vinyl, 1-fluoro vinyl, 1,2-difluoro vinyl, 2,2-difluorovinyl, 1,2,2-trifluorovinyl, 1,2-dibromo ethane, 1,2 difluoro ethane, 1-fluoro-2-bromo ethane, $CF_2CF_3$, $CF_2CF_2CF_3$, and the like.

The term halogen includes bromine, chlorine, fluorine, and iodine.

For the sake of simplicity, connection points ("-") are not depicted. When an atom or compound is described to define a variable, it is understood that it is intended to replace the variable in a manner to satisfy the valency of the atom or compound. For example, when L is $C(R^3)=C(R^3)$, both carbon atoms form a part of the ring in order to satisfy their respective valences.

The term "pharmaceutically acceptable salt", as used herein, refers to salts derived form organic and inorganic acids such as, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable acids when a compound of this invention contains a basic moiety. Salts may also be formed from organic and inorganic bases, preferably alkali metal salts, for example, sodium, lithium, or potassium, when a compound of this invention contains a carboxylate or phenolic moiety, or similar moiety capable of forming base addition salts.

The term "patient", as used herein, refers to a mammal, preferably a human.

The terms "administer", "administering", or "administration", as used herein, refer to either directly administering a compound or composition to a patient, or administering a prodrug derivative or analog of the compound to the patient, which will form an equivalent amount of the active compound or substance within the patient's body.

The term "carrier", as used herein, shall encompass carriers, excipients, and diluents.

The compounds of this invention may contain an asymmetric carbon atom and some of the compounds of this invention may contain one or more asymmetric centers and may thus give rise to optical isomers and diastereomers. While shown without respect to stereochemistry in formula I, the present invention includes such optical isomers and diastereomers; as well as the racemic and resolved, enantiomerically pure R and S stereoisomers; as well as other mixtures of the R and S stereoisomers and pharmaceutically acceptable salts thereof. Where a stereoisomer is preferred, it may in some embodiments be provided substantially free of the corresponding enantiomer. Thus, an enantiomer substantially free of the corresponding enantiomer refers to a compound that is isolated or separated via separation techniques or prepared free of the corresponding enantiomer. "Substantially free", as used herein, means that the compound is made up of a significantly greater proportion of one steriosomer, preferably less than about 50%, more preferably less than about 75%, and even more preferably less than about 90%.

The terms "effective amount", "therapeutically effective amount" and "effective dosage" as used herein, refer to the amount of a compound, that, when administered to a patient, is effective to at least partially ameliorate (and, in preferred embodiments, cure) a condition form which the patient is suspected to suffer.

Biaryl sulfonamide compounds have been found to act as metalloproteinase inhibitors. They are therefore useful in the treatment of cancer, osteoarthritis, rheumatoid arthritis, asthma, COPD, atherosclerosis, age-related macular degeneration, myocardial infarction, corneal ulceration and other ocular surface diseases, hepatitis, aortic aneurysms, tendonitis, central nervous system diseases, abnormal wound healing, angiogenesis, restenosis, cirrhosis, multiple sclerosis, glomerulonephritis, graft versus host disease, diabetes, inflammatory bowel disease, shock, invertebral disc degeneration, stroke, osteopenia, and/or periodontal diseases.

The present invention thus provides pharmaceutical compositions comprising at least one biaryl sulfonamide compound and one or more pharmaceutically acceptable carriers, excipients, or diluents.

Examples of such carriers are well known to those skilled in the art and are prepared in accordance with acceptable pharmaceutical procedures, such as, for example, those described in Remington's Pharmaceutical Sciences, 17th edition, ed. Alfonoso R. Gennaro, Mack Publishing Company, Easton, Pa. (1985), which is incorporated herein by reference in its entirety. Pharmaceutically acceptable carriers are those that are compatible with the other ingredients in the formulation and biologically acceptable.

The compounds of this invention may be administered orally or parenterally, neat or in combination with conventional pharmaceutical carriers. Applicable solid carriers can include one or more substances which may also act as flavoring agents, lubricants, solubilizers, suspending agents, fillers, glidants, compression aids, binders or tablet-disintegrating agents or encapsulating materials. They are formulated in conventional manner, for example, in a manner similar to that used for known antihypertensive agents, diuretics and U-blocking agents. Oral formulations containing the active compounds of this invention may comprise any conventionally used oral forms, including tablets, capsules, buccal forms, troches, lozenges and oral liquids, suspensions or solutions. In powders, the carrier is a finely divided solid, which is an admixture with the finely divided active ingredient. In tablets, the active ingredient is mixed with a carrier having the necessary compression properties in suitable proportions and compacted in the shape and size desired. The powders and tablets preferably contain up to 99% of the active ingredient.

Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc.

Useful tablet formulations may be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, sodium lauryl sulfate, talc, sugars, lactose, dextrin, starch, gelatin, cellulose, methyl cellulose, microcrystalline cellulose, sodium carboxymethyl cellulose, carboxymethylcellulose calcium, polyvinylpyrrolidine, alginic acid, acacia gum, xanthan gum, sodium citrate, complex silicates, calcium carbonate, glycine, sucrose, sorbitol, dicalcium phosphate, calcium sulfate, lactose, kaolin, mannitol, sodium chloride, low melting waxes and ion exchange resins. Preferred surface modifying agents include nonionic and anionic surface modifying agents. Representative examples of surface modifying agents include, but are not limited to, poloxamer 188, benzalkonium chloride, calcium stearate, cetostearl alcohol, cetomacrogol emulsifying wax, sorbitan esters, colliodol silicon dioxide, phosphates, sodium dodecylsulfate, magnesium aluminum silicate, and triethanolamine. Oral formulations herein may utilize standard delay or time release formulations to alter the absorption of the active compound(s). The oral formulation may also consist of administering the active ingredient in water or fruit juice, containing appropriate solubilizers or emulisifiers as needed.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellant.

Liquid pharmaceutical compositions, which are sterile solutions or suspensions, can be utilized by, for example, intramuscular, intraperitoneal or subcutaneous injection. Sterile solutions can also be administered intravenously. Compositions for oral administration may be in either liquid or solid form.

Preferably the pharmaceutical composition is in unit dosage form, e.g. as tablets, capsules, powders, solutions, suspensions, emulsions, granules, or suppositories. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form. Such unit dosage form may contain from about 1 mg/kg to about 250 mg/kg, and may given in a single dose or in two or more divided doses. Such doses may be administered in any manner useful in directing the active compounds herein to the recipient's bloodstream, including orally, via implants, parenterally (including intravenous, intraperitoneal and subcutaneous injections), rectally, vaginally, and transdermally. Such administrations may be carried out using the present compounds, or pharmaceutically acceptable salts thereof, in lotions, creams, foams, patches, suspensions, solutions, and suppositories (rectal and vaginal).

When administered for the treatment or inhibition of a particular disease state or disorder, it is understood that the effective dosage may vary depending upon-the particular compound utilized, the mode of administration, the condition, and severity thereof, of the condition being treated, as well as the various physical factors related to the individual being treated. In therapeutic application, compounds of the present invention are provided to a patient already suffering from a disease in an amount sufficient to cure or at least partially ameliorate the symptoms of the disease and its complications. An amount adequate to accomplish this is defined as a "therapeutically effective amount". The dosage to be used in the treatment of a specific case must be subjectively determined by the attending physician. The variables involved include the specific condition and the size, age and response pattern of the patient.

In some cases it may be desirable to administer the compounds directly to the airways in the form of an aerosol. For administration by intranasal or intrabrochial inhalation, the compounds of this invention may be formulated into an aqueous or partially aqueous solution.

The compounds of this invention may be administered parenterally or intraperitoneally. Solutions or suspensions of these active compounds as a free base or pharmaceutically acceptable salt may be prepared in water suitably mixed with a surfactant such as hydroxyl-propylcellulose. Dispersions may also be prepared in glycerol, liquid polyethylene glycols and mixtures thereof in oils. Under ordinary conditions of storage and use, these preparations contain a preservative to inhibit the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

The compounds of this invention can be administered transdermally through the use of a transdermal patch. For the purposes of this disclosure, thransdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Transdermal administration may be accomplished through the use of a transdermal patch containing the active compound and a carrier that is inert to the active compound, is non-toxic to the skin, and allows delivery of the agent for systemic absorption into the blood stream via the skin. The carrier may take any number of forms such as creams and ointments, pastes, gels and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream, such as a semi-permeable membrane covering a reservoir containing the active ingredient with or without a carrier, or a matrix containing the active ingredient. Other occlusive devices are known in the literature.

The compounds of this invention may be administered rectally or vaginally in the form of a conventional suppository. Suppository formulations may be made from traditional materials, including cocoa butter, with or without the addition of waxes to alter the suppository's melting point, and glycerin. Water soluble suppository bases, such as polyethylene glycols of various molecular weights, may also be used.

In certain embodiments, the present invention is directed to prodrugs of biaryl sulfonamide compounds. Various forms of prodrugs are known in the art, for example, as discussed in, for example, Bundgaard, (ed.), Design of Prodrugs, Elsevier (1985); Widder, et al. (ed.), Methods in Enzymology, vol. 4, Academic Press (1985); Krogsgaard-Larsen, et al. (ed.), "Design and Application of Prodrugs", Textbook of Drug Design and Development, Chapter 5, 113–191 (1991), Bundgaard, et al., Journal of Drug Deliver reviews, 8:1–38 (1992), Bundgaard, J. of Pharmaceutical Sciences, 77:285 et seq. (1988); and Higuchi and Stella (eds.) Prodrugs as Novel Drug Delivery Systems, American Chemical Society (1975), each of which is incorporated by reference in its entirety.

It is understood that the dosage, regimen and mode of administration of these compounds will vary according to the malady and the individual being treated and will be subject to the judgment of the medical practitioner involved. It is preferred that the administration of one or more of the compounds herein begin at a low dose and be increased until the desired effects are achieved.

The compounds of the current invention were prepared according to the following general synthetic scheme from commercially available starting materials, materials prepared as described in literature procedures, or new intermediates described in the schemes and experimental procedures. This general scheme covers most of the examples. For more detailed information, please refer to the schemes in the session of Synthetic Methods and Examples.

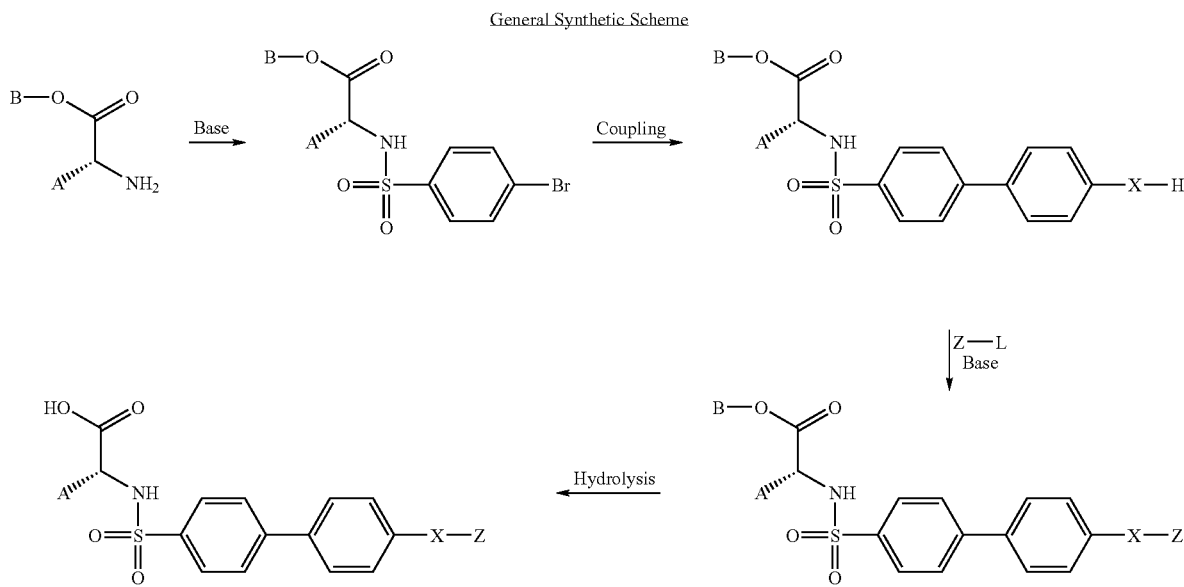

General Synthetic Scheme

Bases used here are Et3N, K2CO3, NaH, Hunig base, etc. Coupling was generally referred to Suzuki coupling or Stille coupling. Hydrolysis was carried out using TFA, NaOH, LiOH, K2CO3, etc.

The compounds of the invention can be prepared using a variety of methods starting from commercially available compounds, known compounds, or compounds prepared by known methods. General synthetic routes to many of the compounds of the invention are included in the following schemes. It is understood by those skilled in the art that protection and deprotection steps not shown in the Schemes may be required for these syntheses, and that the order of steps may be changed to accommodate functionality in the target molecules.

In Scheme 1 the compounds of the invention, 1, are prepared in 4 steps. Sulfonylation of valine methyl ester with 4-Bromo-benzenesulfonyl chloride was carried out under Hunig base condition to give sulfonamide intermediate 1. This 4-Bromo-benzenesulfonamide was furthered coupled with boronate ester using Palladium catalyst under Suzuki coupling condition to provide biphenyl sulfonamide Intermediate 2. Biphenyl sulfonamide intermediate 2 was then alkylated with various alkylating reagents to provide biphenyl sulfonamide ester (Intermediate 3). Hydrolysis of intermediate 3 was carried out using bases such as NaOH, or LiOH to afford the final product 1.

Suzuki condition to provide biphenyl sulfonamide intermediate 5, which was hydrolyzed to final product under basic conditions.

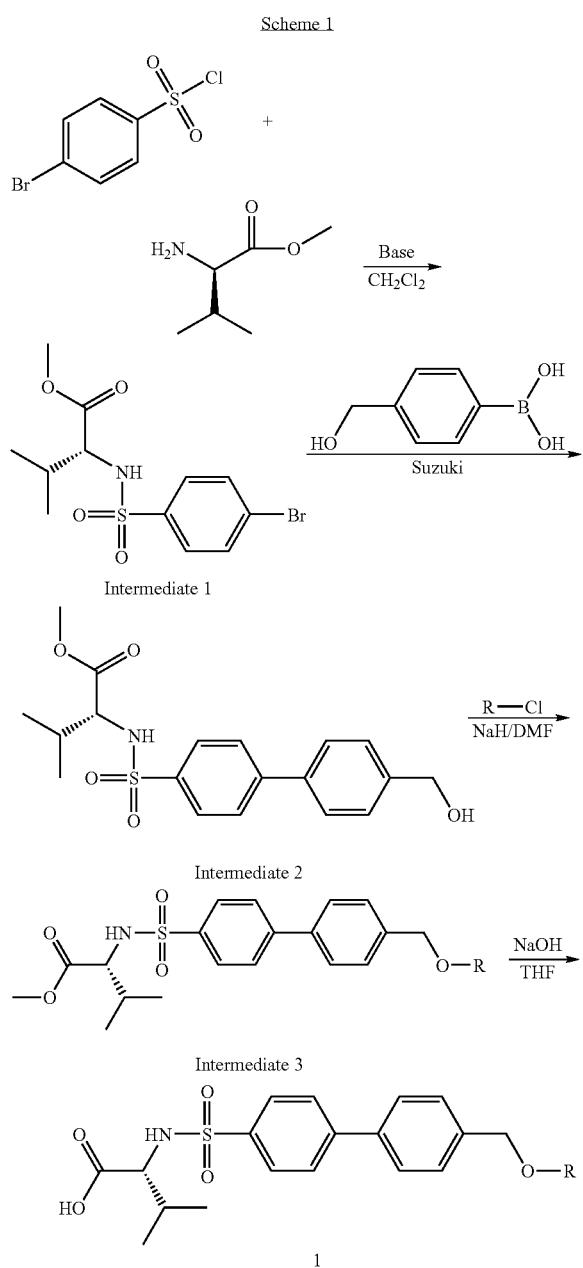

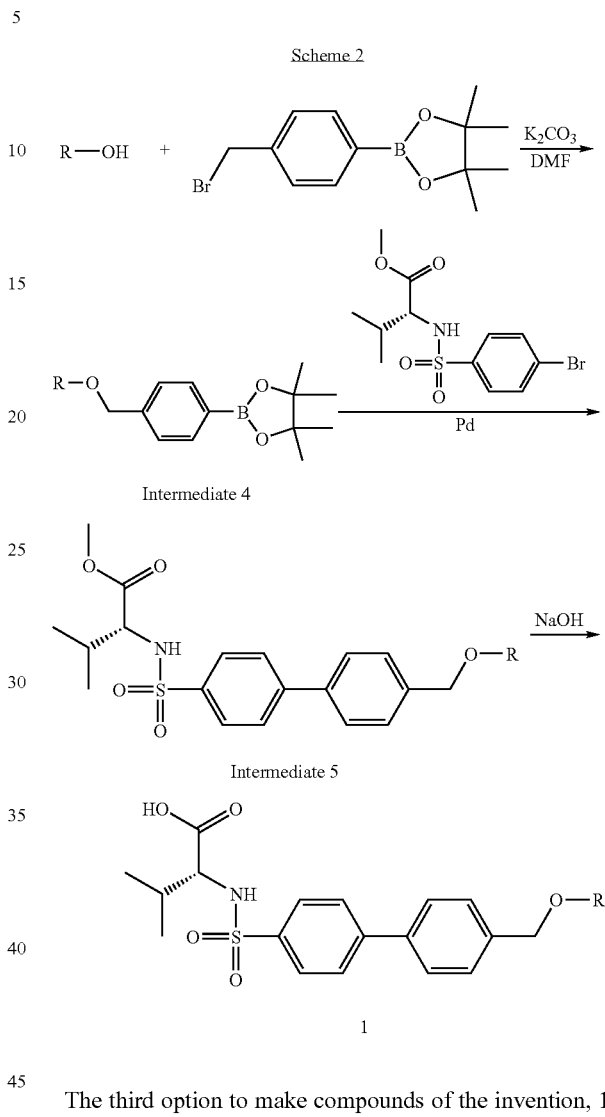

The third option to make compounds of the invention, 1, are carried out based on Scheme 3. The synthetic sequence in Scheme 3 is similar to that in Scheme 1 but using different starting material, valine tert-butyl ester. Therefore, final step to form the product 1 was carried out by using TFA to deprotect the tert-butyl ester group of Intermediate 8.

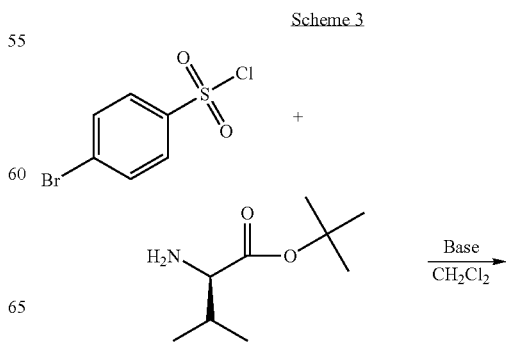

An alternative route to compounds 1 is shown in Scheme 2. Phenol derivative was converted to Pinacolborane (Intermediate 4) under basic condition in DMF. Pinacolborane was then coupled with 4-bromo-benzenesulfonamide under -continued

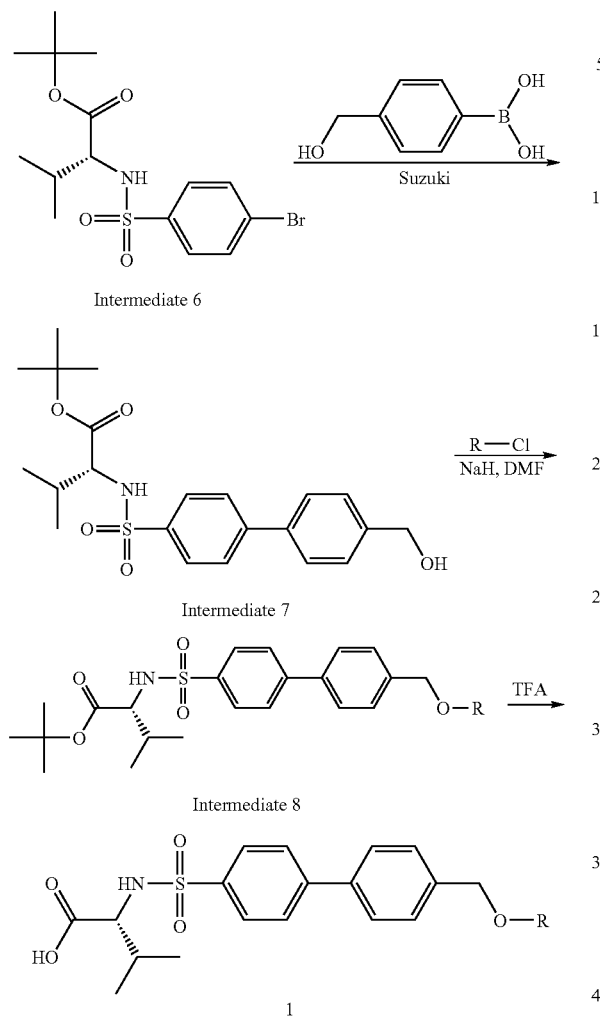

Slight modification of Scheme 3 resulted in another to make the compounds of invention, 1. This is illustrated in Schem 4A. In this case, boronate esters with suitable ether moiety are purchased from commercial source and used for Suzuki coupling to provide intermediate 8. TFA deprotection of tert-butyl ester from intermediate 8 resulted the desired final product 1.

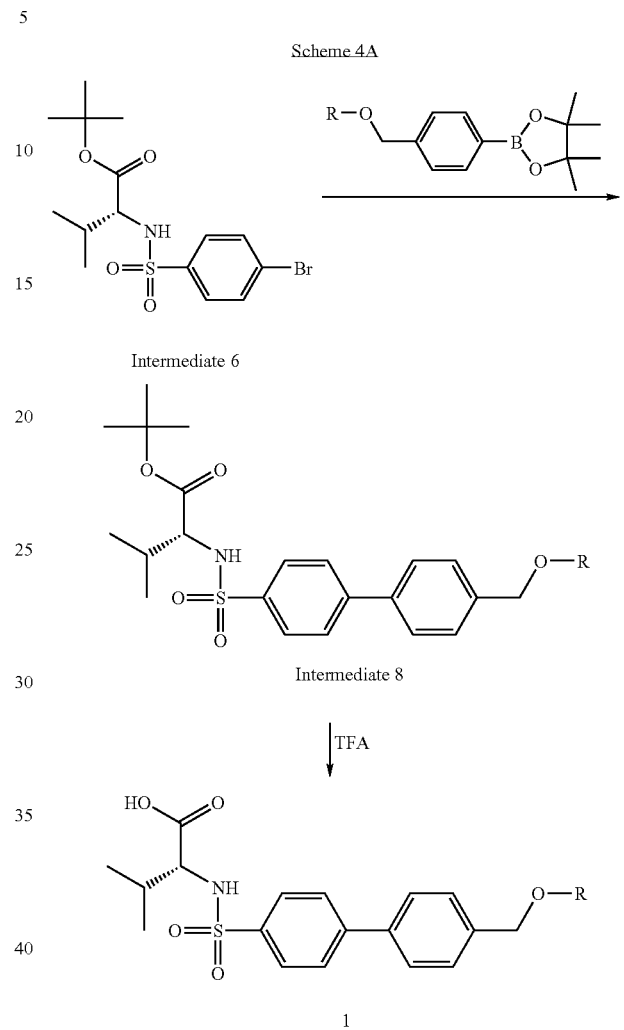

Compounds of the invention, 1, can also be made by hydrolysis of ester such as intermediate 10.

Scheme 4B

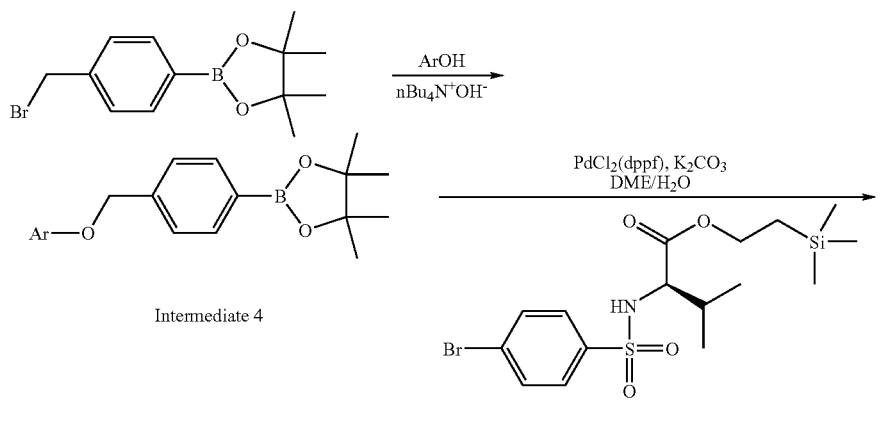

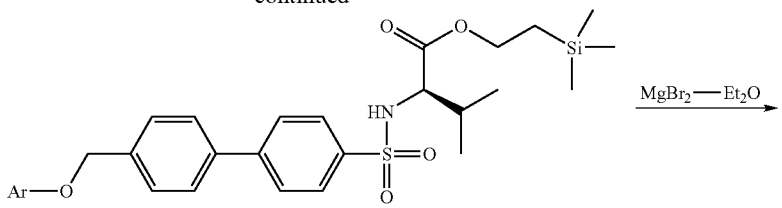

Intermediate 10

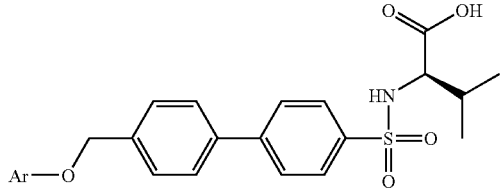

1

Alkylation

The phenol derivative (4.14 mmol) is dissolved in methanol (6 mL) and treated with tetrabutylammonium hydroxide (4.14 mmol.) The mixture is stirred for 10 minutes, and the solvent is removed under reduced pressure. The residue is dissolved in THF (10 mL) and treated with a solution of the benzylic bromide (4.14 mmol) in THF (5 mL.) The reaction is stirred at rt overnight. The solvent is removed under reduced pressure and redissolved in dichloromethane (5 mL) and ether (50 mL.) The organic solution is washed with water (4×50 mL) and saturated sodium chloride solution (50 mL,) and dried over magnesium sulfate. The organic solution is filtered and concentrated under reduced pressure. The crude material is purified by flash silica gel chromatography to yield the purified product in 53% yield.

Suzuki Coupling

The boronate ester (1.07 mmol) and aryl bromide (1.07 mmol) are dissolved in ethylene glycol dimethyl ether (10 mL) and the resulting solution is treated with tetrakis (triphenylphosphine)palladium(0) (0.054 mmol.) A solution of potassium carbonate (2.14 mmol) in water (3.5 mL) is added, and the reaction is heated to reflux for 1 h. The reaction is cooled, filtered to remove solids, diluted with water (10 nL) and concentrated under reduced pressure. The residue is extracted with dichloromethane (3×25 mL) and the organic layers are washed with water (25 mL) and saturated sodium chloride solution (25 nL). The organic solution is dried over magnesium sulfate, filtered and concentrated under reduced pressure. Purification by flash silica gel chromatography furnishes the product in 57% yield. In some cases, PdCl2(dppf) was used as the catalyst instead of tetrakis(triphenylphosphine)palladium(0).

Deprotection with MgBr$_2$.

The 2-(trimethylsilyl)ethyl ester (0.0621 mmol) is dissolved in dichloromethane (58 mL) and treated with magnesium bromide etherate (0.186 mmol). The mixture is stirred vigorously overnight or until reaction is complete and then shaken with 10% HCl (3×25 mL) and saturated sodium chloride solution (25 mL). The organic solution is then dried over magnesium sulfate, filtered and concentrated under reduced pressure to yield the product in 95% yield. The crude product could be purified by HPLC when required.

Suzuki coupling can be carried out on free acid with boronate ester. Therefore, hydrolysis of the esters is avoided. This result in direct preparation of the compounds, 1.

Scheme 4C

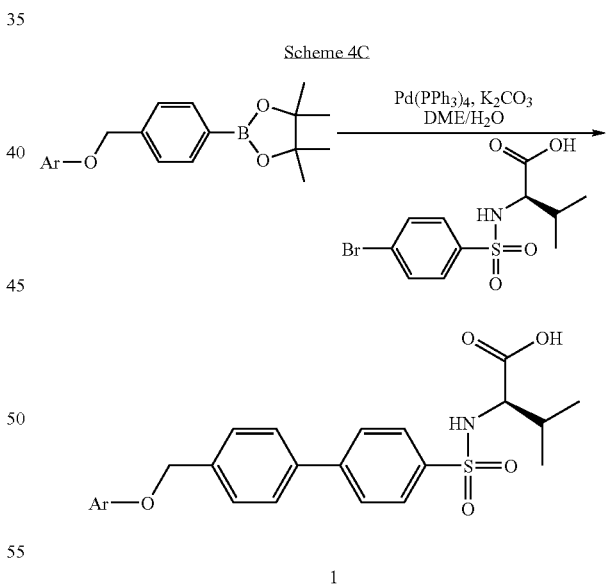

1

Suzuki Coupling with Free Acid

The boronate ester (1.36 mmol) and bromoacid (1.36 mmol) are dissolved in ethylene glycol dimethyl ether (13.8 mL) and the resulting solution is treated with tetrakis (triphenylphosphine)palladium(0) (0.068 mmol). After stirring at rt for 10 minutes, a solution of potassium carbonate (4.08 mmol) in water (4.8 mL) are added. The solution is heated to reflux for 2 h, and then allowed to cool to rt overnight. The mixture is concentrated to an aqueous residue under reduced pressure and ethyl acetate (50 mL) is added. The organic mixture is washed with 10% HCl (2×25 mL) and saturated sodium chloride (25 mL). The organic solution is dried over magnesium sulfate, filtered and concentrated to a crude residue, which is purified using flash silica gel chromatography to obtain the product in 64% yield.

In Scheme 5 the compounds of the invention, 2, are prepared in 3 steps. Boronate ester (intermediate 11) was prepared by alkylation under basic condition. Intermediate 11 thus obtained can be easily coupled with 4-bromobenzenesulfonamide derivative to provide biphenyl sulfonamide analog (intermediate 12).

The ester functional group in intermediate 12 can be hydrolyzed under various condition to yield the desired product biphenyl sulfonamide analog, 2.

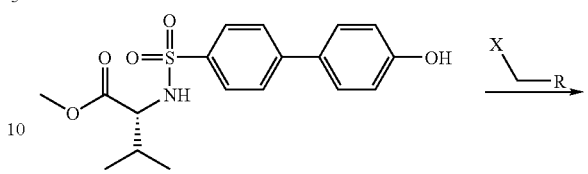

Scheme 6

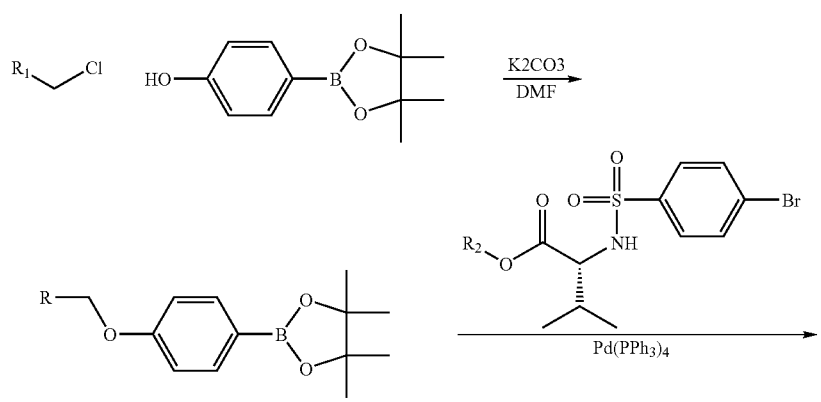

Scheme 5

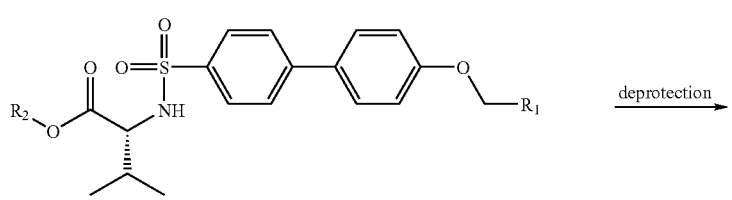

Intermediate 11

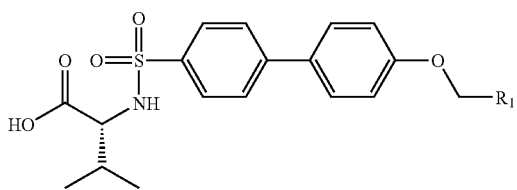

Intermediate 12

2

Alternate route to provide compounds, 2, is shown in Scheme 6. Starting material 4-hydroxybiphenyl sulfonamide derivative was readily available through Suzuki coupling. Alkylation of 4-hydroxybiphenyl sulfonamide under basic condition provides biphenyl sulfonamide intermediate 13 with an ether linker. Hydrolysis of ester (intermediate 13) using aqueous NaOH to afford the desired product of the invention, 2.

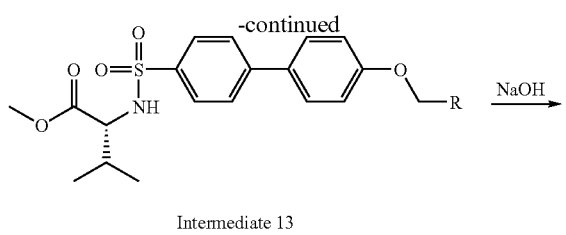

Intermediate 13

-continued

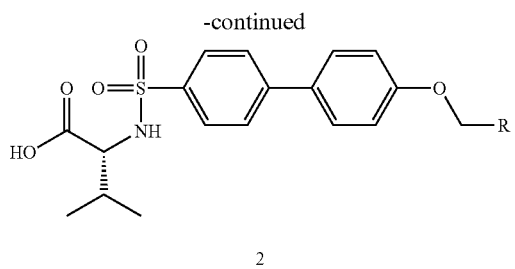

2

Scheme 6B

Deprotection of Methyl esters:

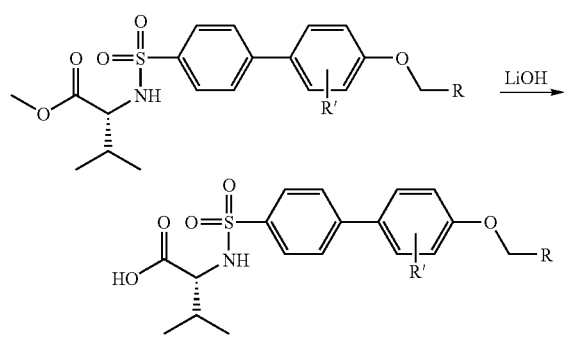

The methyl ester (0.294 mmol) was dissolved in THF: MeOH (2:1)(2 mL) and 1M LiOH (0.881 mmol) was added. Reaction stirred for 3 days. The solvent was removed and the remaining white solid was dissolved in H₂O. The H₂O was extracted with ether. The ether layer was removed and the aqueous layer was acidified to pH 2 with HCl (conc.) forming a cloudy solution. This was extracted with CH₂Cl₂. The aqueous layer was removed and the organic layer was washed with brine. The solvent was removed and the remaining solid was dissolved in minimal CH₂Cl₂ and then hexanes was added precipitating a white solid. The solid was filtered and dried at reduced pressure to provide the desired product.

Compounds of the invention, 3, are prepared based on the Scheme 7. 4-Vinylphenylboronic acid and 4-bromobenzene sulfonamide derivative was undergoing Suzuki coupling catalyzed by Palladium catalyst to provide intermediate 14. Heck reaction of 14 with aryl halide generated intermediate 15. Intermediate 15 is biphenyl sulfonamide derivative with a double as linker connected to aryl ring. Regular TFA deprotection of tert-butyl ester of intermediate 15 provides desired product 3 in high yield.

Scheme 7

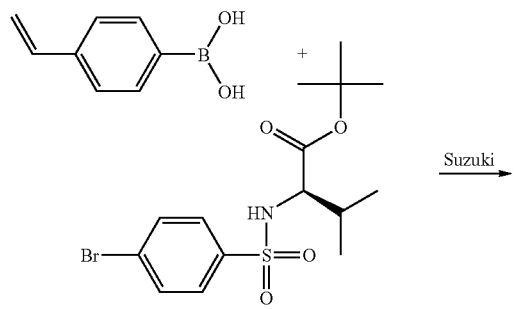

-continued

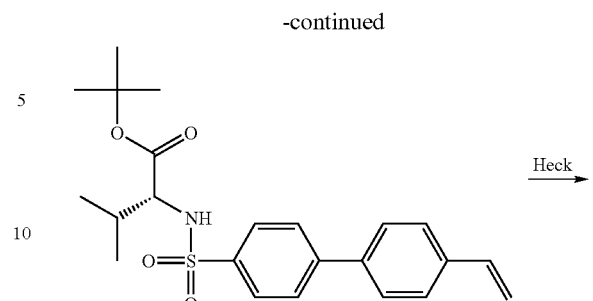

Intermediate 14

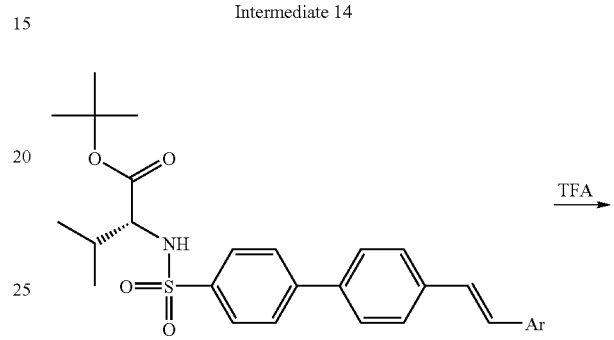

Intermediate 15

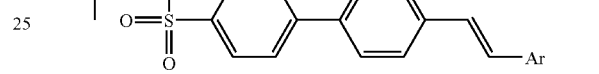

3

Scheme 8 shows the multiple steps synthesis leading to the compounds of invention, 4. Regular Suzuki coupling followed by the alkylation with Triflic anhydride to furnish triflate intermediate 16. Triflate 16 was converted into alkynylation product 17 through Sonagoshira reaction. TBDMS protecting group in 17 was removed by TBAF followed by another Sonagoshira reaction to provide advanced intermediate 18 with triple bond linking biphenyl group with aryl moiety. 18 was then reduced by hydrogenation then TFA deprotection to give the desired product 4.

Scheme 8

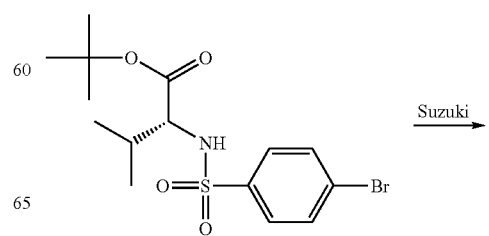

-continued

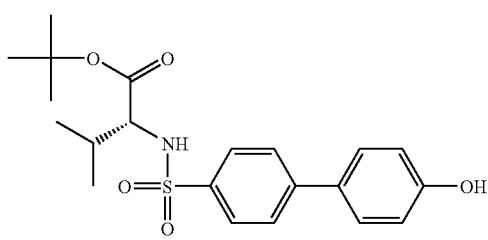

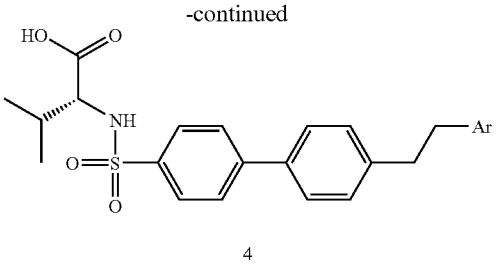

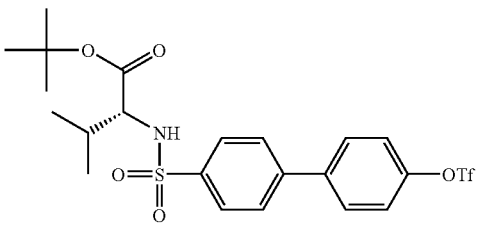

Intermediate 16

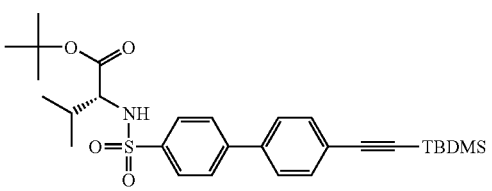

Intermediate 17

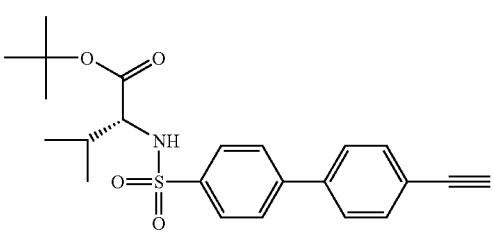

Intermediate 18

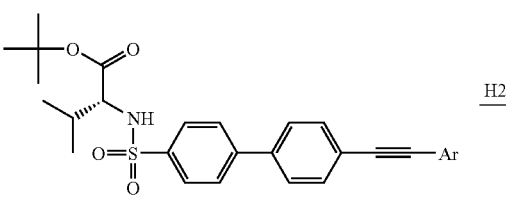

Routes to compounds of structure 5 are shown in Scheme 9. 4-aminomethyl phenyl boronic acid was used for Suzuki coupling to produce the intermediate 19. Acylation of 19 with acetic anhydride, followed by the TFA deprotection to provide compounds with structure 5.

Scheme 9

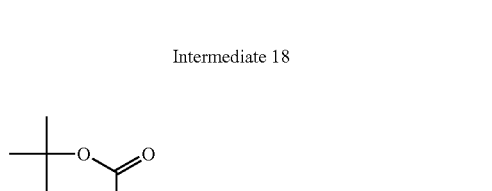

Intermediate 19

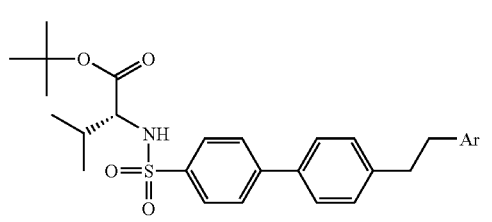

Intermediate 20

5

Alternate route to make structures of 5 is presented in Schem10. Intermediate 21 was formed by EDCI coupling of 4-bromophenylacetic acid with phenylamine in DMF. Stille coupling of 21 with corresponding tin reagent followed by TFA deprotection to provide product 5.

Scheme 10

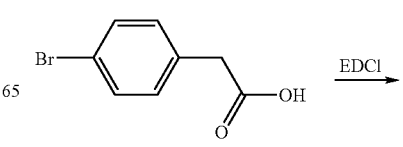

-continued

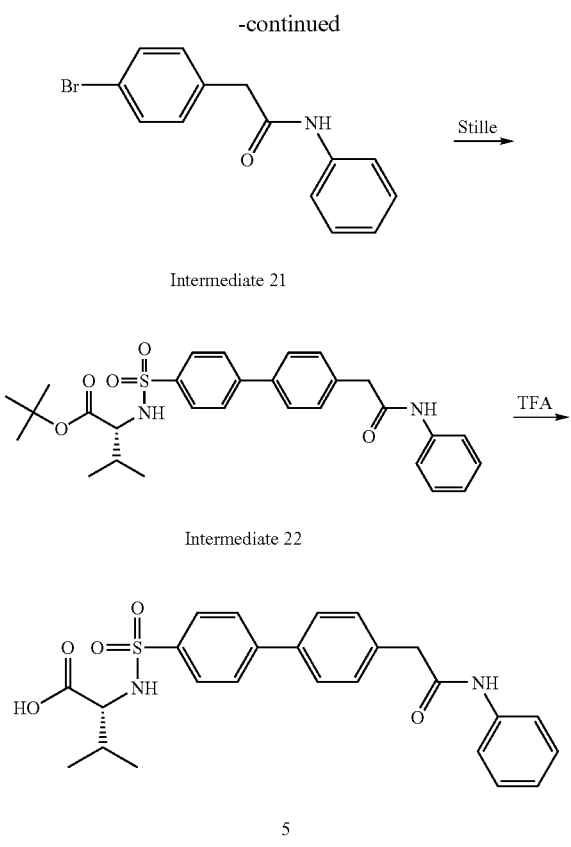

In Scheme 11 the compounds of the invention, 6, are prepared by reacting 4-hydroxybiphenyl sulfonamide derivative with various isocyanate with the presence of triethylamine. Carbamate (Intermediate 24) thus obtained was treated with TFA to remove tert-butyl ester to provide compounds 6.

-continued

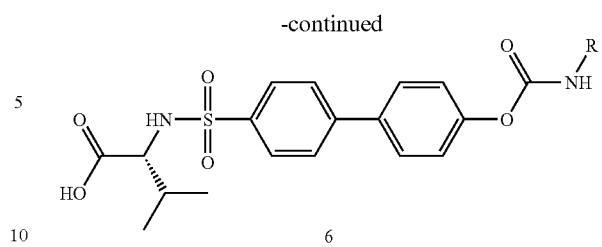

Alternate route to make compounds 6 was shown in Scheme 12 using 4-hydroxybiphenyl sulfonamide free acid to react with isocyanate with the presence of triethyl amine. Compounds 6 are obtained directly without deprotection step.

Scheme 12

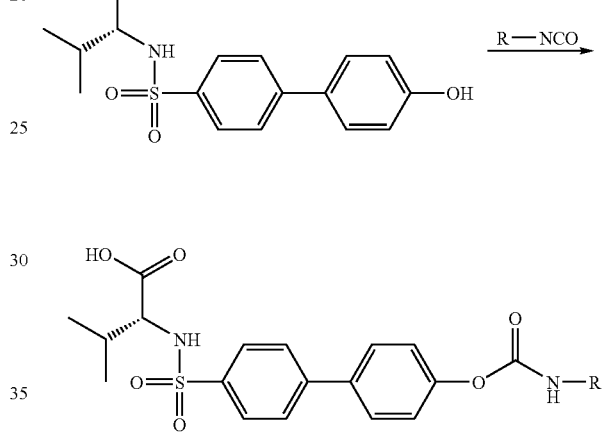

Routes to compounds of structure 7 are shown in Scheme 13. Intermediate 23 was coupled with carboxylic acid using DCC reagent to provide ester 24. Intermediate 24 was treated with TFA to selectively remove tert-butyl group to provide compounds 7.

Scheme 13

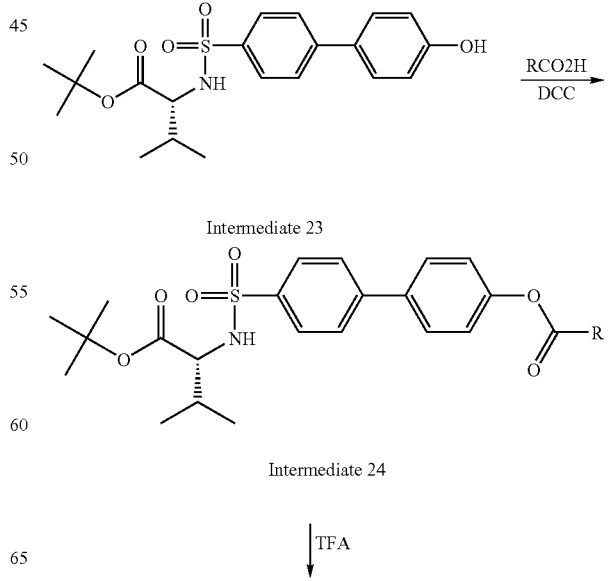

Scheme 11

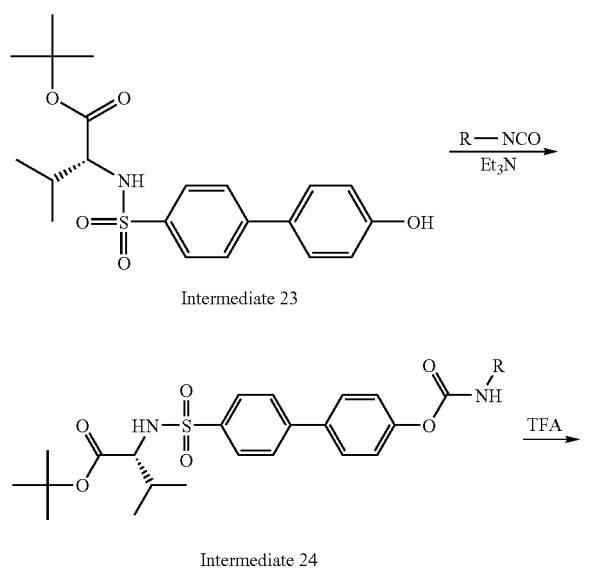

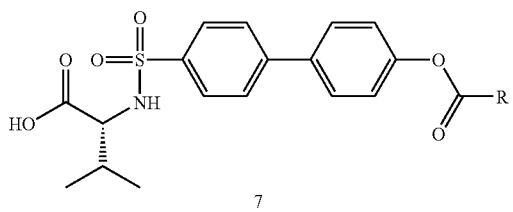

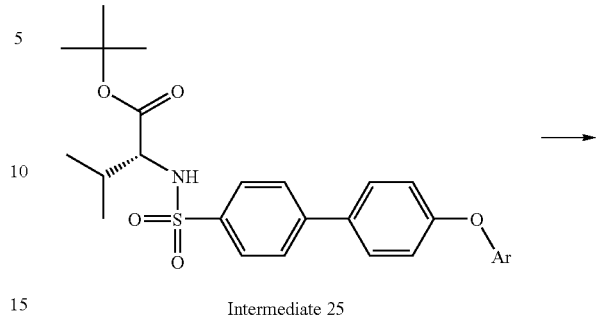

In Scheme 14, the compounds of the invention, 8, are prepared from intermediate 23 by alkylation followed by the deprotection of tert-butyl group with TFA.

Scheme 14

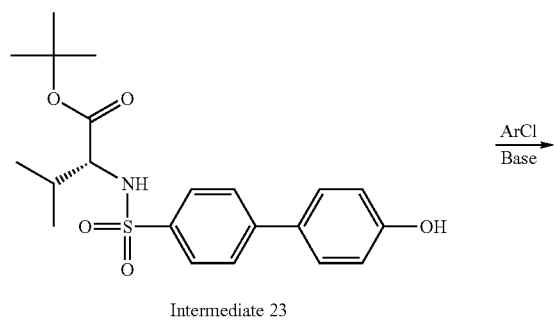

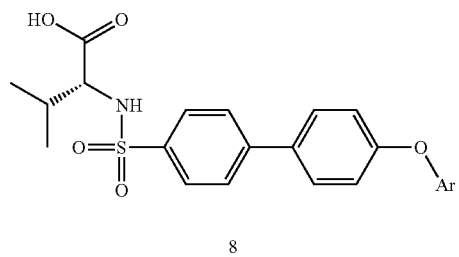

In Scheme 15 the compounds of the invention, 9, are prepared in a multiple step synthesis. Intermediate 26 was prepared based on known literature procedure. Stille coupling followed by TFA deprotection to provide desired product 9.

Scheme 15

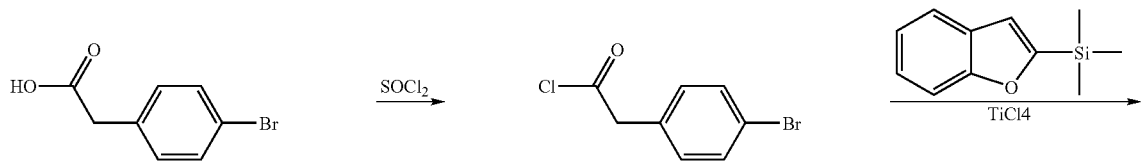

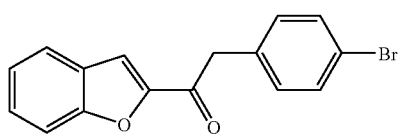

intermediate 26

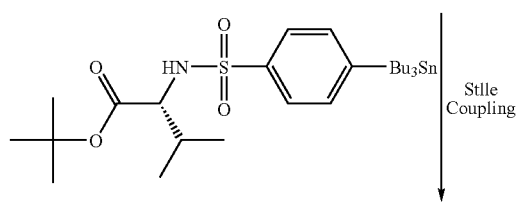

Stlle Coupling

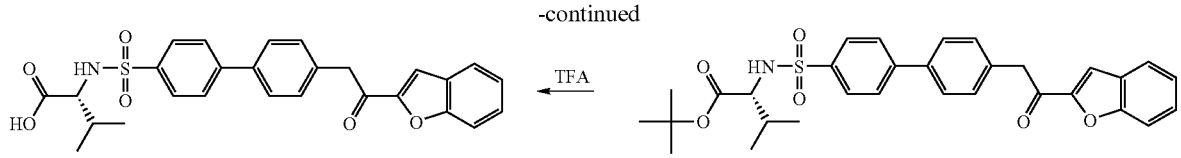

Routes to compounds of structure 10 are shown in Scheme 16. Intermediate 28 (2-[1,2,3]Thiazol-4-yl-phenol) was prepared according to literature procedure. Alkylation with benzyl bromide derivative followed by condensation resulted in thioether intermediate 29. Suzuki coupling of 29 with 4-bromobenzene sulfonamide to generate intermediate 30. Oxidation with MCPBA followed by hydrolysis to provide compound 10.

Scheme 16

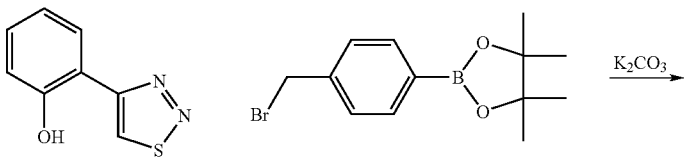

Intermediate 28

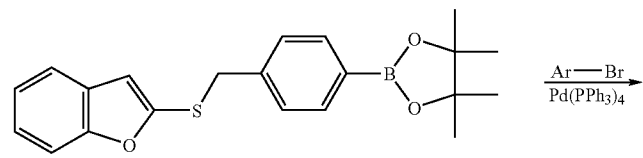

Intermediate 29

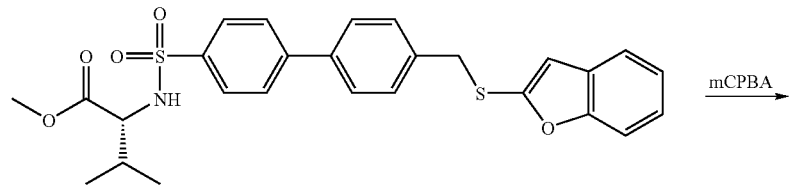

Intermediate 30

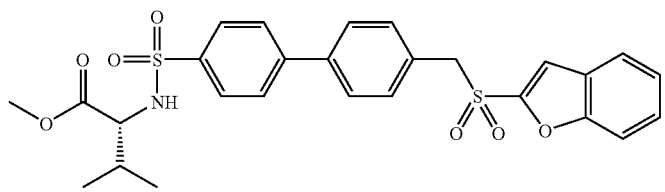

Intermediate 31

-continued

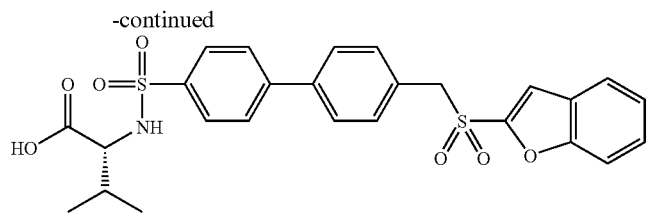

10

TFA Deprotection of t-butyl ester

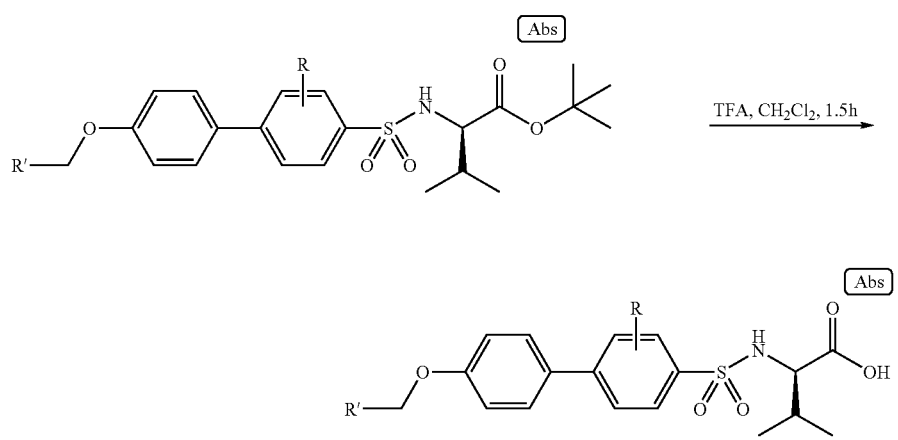

The t-butyl ester (0.505 mmol) was dissolved in CH$_2$Cl$_2$ (2.5 mL). TFA (2.5 mL) was dissolved in CH$_2$Cl$_2$ (2.5 mL), and this was slowly added to the dissolved ester. Stirred for 1.5 h. The solvent was removed at reduced pressure and the remaining oil dissolved in toluene and toluene removed. Finally the oil was dissolved in a minimal amount of CH$_2$Cl$_2$ and hexanes added to precipitate a white solid. Solvent removed at reduced pressure, and the solid dried on vacuum pump to give a 98% yield.

MMPs and aggrecacnases can degrade various components of connective tissue, including collagen and proteoglycan. In the absence of natural checks on this activity, a variety of pathologies and undesirable effects can occur. In fact, MMPs and aggrecanases are known to play a role in many disorders in which extracellular protein degradation/destruction occurs, such as cancer, osteoarthritis, rheumatoid arthritis, asthma, chronic obstructive pulmonary disease ("COPD"), atherosclerosis, age-related macular degeneration, myocardial infarction, corneal ulceration and other ocular surface diseases, hepatitis, aortic aneurysms, tendonitis, central nervous system diseases, abnormal wound healing, angiogenesis, restenosis, cirrhosis, multiple sclerosis, glomerulonephritis, graft versus host disease, diabetes, inflammatory bowel disease, shock, invertebral disc degeneration, stroke, osteopenia, and periodontal diseases.

The preferred metalloproteinase is Aggrecanase-1 (Agg-1). The molecular weight of full length Agg-1 is around 62 KD. The cDNA sequence contains a 2511-base pair encoding 837 amino acids (Tortorella, M D et al., Science, 1999, 284, 1664–1666). The Agg-1 protein may be produced by culturing a cell transformed with the DNA sequence and recovering and purifying protein from the culture medium (Racie, L A et al, PCT Int. Appl. Analysis of Agg-1 protein is conducted using standard techniques such as SDS-PAGE acrylamide (Laemmli, Nature, 1970, 227, 680) stained with silver (Oaklet et al. Anal. Biochem, 1980, 105, 361) and by immunoblot (Towbin, et al. Proc. Natl. Acad. Sci. USA, 1979, 76, 4350). Biological activity of Agg-1 can be further characterized by the ability to demonstrate aggrecan proteolytic activity in an assay which determines the presence of an aggrecan-degrading molecule. These assays or the development thereof is within the knowledge of one skilled in the art. Such assays may involve contacting an aggrecan substrate with the aggrecanase molecule and mornitoring the production of aggrecan fragments (Hughes et al., Biochem J, 1995, 305, 799–804).

The invention includes methods for developing inhibitors of aggrecanase and the inhibitors produced thereby. Compounds are assessed by their ability to inhibit cleavage of a fluorescent peptide substrate (Abz-TEGARGSVI-Dap(Dnp) (Abz:o-aminobenzoyl; Dnp: 2,4 dinitrophenyl) (Anaspec Inc). The peptide sequence TEGARGSVI is based on the amino acid sequence of the Glu373-Ala374 cleavage site of aggrecan in osteoarthritis. Inhibitors are pre-incubated with purified full-length human recombinant aggrecanase-1 for 10 min followed by the addition of substrate, at temperatures ranging from 25° C. to 37° C., typically at 30° C. Cleavage of the Glu-Ala bond releases the fluorophore from internal quenching. This results in an increase in fluorescence monitored at $\lambda_{ex}$ 340 nm and $\lambda_{ex}$ 420 nm over a period of 40 min. The initial rate (v) at each concentration of the substrate is fit to the following equation $V=V\text{max} \cdot S^h/(S^h_{0.5}+S^h)$ where h is the Hill constant and $S_{0.5}$ is the substrate concentration at half the Vmax. The percentage activity remaining in the presence of inhibitor is plotted as a function of inhibitor concentration and the $IC_{50}$ value is determined by fitting the data to the following equation:

% activity=$100 IC_{50}/(I_o+IC_{50})$.

Candidate molecules are further assayed for inhibitory activity in secondary assay such as cell-based assay. Assays for the inhibitors involve contacting a mixture of aggrecan (proteoglycan from the slice of cartilage) and the inhibitor with an aggrecanase molecule followed by measurement of the aggrecanase inhibition, for instance by detection and measurement of aggrecan fragments produced by cleavage at an aggrecanase susceptible site.

Another aspect of the invention therefore provides pharmaceutical compositions containing a therapeutically effective amount of aggrecanase inhibitors, in a pharmaceutically acceptable vehicle. Aggrecanase-mediated degradation of aggrecan in cartilage has been implicated in osteoarthritis and other inflammatory diseases. Therefore, these compositions of the invention may be used in the treatment of diseases characterized by the degradation of aggrecan and/or an upregulation of aggrecanase. The compositions may be used in the treatment of these conditions or in the prevention thereof.

Pharmaceutically acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable aids when a compound of this invention contains a basic moiety. Salts may also be formed from organic and inorganic bases, such as alkali metal salts (for example, sodium, lithium, or potassium) alkaline earth metal salts, ammonium salts, alkylammonium salts containing 1–6 carbon atoms or dialkylammonium salts containing 1–6 carbon atoms in each alkyl group, and trialkylammonium salts containing 1–6 carbon atoms in each alkyl group, when a compound of this invention contains an acidic moiety.

The term "alkyl", as used herein, whether used alone or as part of another group, refers to a substituted or unsubstituted aliphatic hydrocarbon chain and includes, but is not limited to, straight and branched chains containing from 1 to 12 carbon atoms, preferably 1 to 6 carbon atoms, unless explicitly specified otherwise. For example, methyl, ethyl, propyl, isopropyl, butyl, i-butyl and t-butyl are encompassed by the term "alkyl." C1–C6 alkyl includes straight and branched chain aliphatic groups having from 1 to 6 carbons. Specifically included within the definition of "alkyl" are those aliphatic hydrocarbon chains that are optionally substituted.

The carbon number as used in the definitions herein refers to carbon backbone and carbon branching, but does not include carbon atoms of the substituents, such as alkoxy substitutions and the like.

The term "alkenyl", as used herein, whether used alone or as part of another group, refers to a substituted or unsubstituted aliphatic hydrocarbon chain and includes, but is not limited to, straight and branched chains having 2 to 8 carbon atoms and containing at least one double bond. Preferably, the alkenyl moiety has 1 or 2 double bonds. Such alkenyl moieties may exist in the E or Z conformations and the compounds of this invention include both conformations. C2–C6 alkenyl includes a 1 to 6 carbon straight or branched chain having at least one carbon-carbon double bond. Specifically included within the definition of "alkenyl" are those aliphatic hydrocarbon chains that are optionally substituted. Heteroatoms, such as O, S or N—R1, attached to an alkenyl should not be attached to a carbon atom that is bonded to a double bond.

The term "alkynyl" refers to a hydrocarbon moiety containing at least one carbon-carbon triple bond. C2–C6 alkynyl includes a 1 to 6 carbon straight or branched chain having at least one carbon-carbon triple bond.

The term "cycloalkyl" a monocyclic, bicyclic, tricyclic, fused, bridged, or spiro monovalent saturated hydrocarbon moiety, wherein the carbon atoms are located inside or outside of the ring system. Any suitable ring position of the cycloalkyl moiety may be covalently linked to the defined chemical structure. Examples of cycloalkyl moieties include, but are not limited to, chemical groups such as cyclopropyl, cyclopropylmethyl, cyclobutyl, cyclopentyl, cyclohexyl, cyclohexylmethyl, cyclohexylethyl, cycloheptyl, norbornyl, adamantyl, spiro[4.5]decanyl, and homologs, isomers, and the like. C3–C6 cycloalkyl includes monocyclic, saturated rings of 3 to 6 carbons, optionally substituted with $R^3$.

"Heteroaryl" refers to a 5 to 6 membered aromatic heterocyclic ring which contains from 1 to 3 heteroatoms selected from the group consisting of oxygen, nitrogen, and sulfur atoms in the ring and may be fused with a carbocyclic or heterocyclic ring at any possible position.

"Heterocycloalkyl" refers to a 5 to 7-membered saturated ring containing carbon atoms and from 1 to 2 heteroatoms selected from N, O, and S.

The term "phenyl", as used herein, whether used alone or as part of another group, refers to a substituted or unsubstituted phenyl group.

An optionally substituted moiety may be substituted with one or more substituents. Suitable optionally substituents may be selected independently from H, halogen, C1–C6 alkyl, C2–C6 alkenyl, C2–C6 alkynyl, $NR^4R^5$, $N[(CH_2)_2]_2O$, $N[(CH_2)_2]_2NR^4$, $NHSO_2R^4$, $NR^4C(=O)R^5$, $NHC(=O)OR^4$, $NO_2$, $SO_2NR^4R^5$, $SO_2R^4$, $OR^4$, $C(=O)R^4$, $COOR^4$, $CONR^4R^5$, and CN.

When such moieties are substituted, for example, they may typically be mono-, di-, tri- or persubstituted. Examples for a halogen substituent include 1-bromo vinyl, 1-fluoro vinyl, 1,2-difluoro vinyl, 2,2-difluorovinyl, 1,2,2-trifluorovinyl, 1,2-dibromo ethane, 1,2 difluoro ethane, 1-fluoro-2-bromo ethane, $CF_2CF_3$, $CF_2CF_2CF_3$, and the like.

The term halogen includes bromine, chlorine, fluorine, and iodine.

For the sake of simplicity, connection points ("-") are not depicted. When an atom or compound is described to define a variable, it is understood that it is intended to replace the variable in a manner to satisfy the valency of the atom or compound. For example, when L is $C(R^3)=C(R^3)$, both carbon atoms form a part of the ring in order to satisfy their respective valences.

The present invention is further described in the following examples.

EXAMPLES

Examples 1A and 1B were made based on Scheme 1

Example 1A

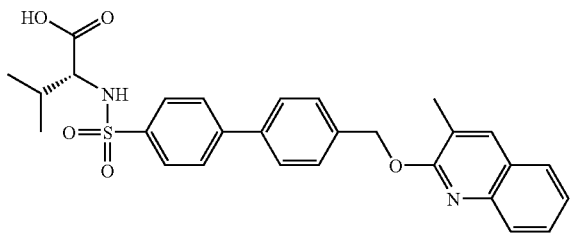

3-Methyl-2-[4'-(3-methyl-quinolin-2-yloxymethyl)-biphenyl-4-sulfonylantinol-butyric acid Step 1A [Intermediate 1] To a dry round-bottom flask was added 4-Bromo-benzenesulfonyl chloride (12.2 g, 47.7 mmol, 1 equiv.), anhydrous methylene chloride (170 mL), and H-D-Val-OMe (8.0 g, 47.7 mmol, 1 equiv.). The mixture was cooled to 0° C. in an ice bath followed by the addition of Hunig base (19.11 mL, 109.7 mmol, 2.3 equiv.). The reaction mixture was allowed to warm to room temperature and was stirred overnight. Reaction was complete as determined by TLC. The reaction mixture was then diluted with dichloromethane (100 mL) and washed with brine. The organic layer was dried over anhydrous $MgSO_4$, solvent evaporated to yield 2-(4-Bromo-benzenesulfonylamino)-3-methyl-butyric acid methyl ester in 96% yield (16.0 g). 1H NMR (400 MHz, CHLOROFORM-D) δ ppm 0.87 (d, J=6.82 Hz, 3 H) 0.96 (d, J=6.82 Hz, 3 H) 2.04 (m, 1 H) 3.49 (s, 3 H) 3.74 (d, J=14.40 Hz, 1 H) 5.10 (d, J=9.85 Hz, 1 H) 7.66 (m, 4 H).

Step 1B [Intermediate 2: 2-(4-Bromo-benzenesulfonylamino)-3-methyl-butyric acid methyl ester (3.4 g, 9.71 mmol), 4-hydroxymethyl phenyl boronic acid (1.48 g, 9.71 mmol, 1 equiv.), $Pd(PPh_3)_4$ (561mg, 0.48 mmol, 0.05 equiv.) were dissolved in ethylene glycol dimethyl ether (90 mL) under $N_2$ atmosphere and stirred at room temperature for 30 min. Then $K_2CO_3$ (2.68 g, 19.4 mmol, 2 equiv.) in $H_2O$ (30 mL) was introduced to the reaction mixture and heat to reflux overnight. After TLC confirmation of reaction completion, solvent was removed by rotovap, residue partitioned between EtOAc and brine, organic layer dried over $MgSO_4$, solvent removed, crude residue was triturated with EtOAc to give 2-(4'-Hydroxymethyl-biphenyl-4-sulfonylamino)-3-methyl-butyric acid methyl ester in 67% yield (2.46 g).

1H NMR (400 MHz, CHLOROFORM-D) δppm 0.90 (d, J=7.07 Hz, 3 H) 0.97 (d, J=6.82 Hz, 3 H) 1.57 (s, 1 H) 2.04 (m, I H) 3.43 (s, 3 H) 3.79 (dd, J=10.11, 5.05 Hz, 1 H) 4.78 (s, 2 H) 5.11 (d, J=10.36 Hz, 1 H) 7.49 (d, J=8.34 Hz, 2 H) 7.60 (d, J=8.34 Hz, 2 H) 7.70 (d, J=8.84 Hz, 2 H) 7.88 (d, J=8.59 Hz, 2 H).

Step 1C [Intermediate 3: 2-(4'-Hydroxymethyl-biphenyl4-sulfonylamino)-3-methyl-butyric acid methyl ester (1.2 g, 3.2 mmol, 1.0 equiv.), 2-chloro-3-methyl quinoline (2.26 g, 12.7 mmol, 4 equiv.) were dissolved in DMF (30 mL) followed by the addition of NaH (382 mg, 60% in oil, 9.54 mmol, 3 equiv.). The mixture was stirred at 100° C. for 5 hrs, then at room temperature overnight. The reaction mixture was then poured into cold water, solid precipitated from the mixture was collected by filtration and washed with water. Regular column chromatography (Silica gel, 1% $MeOH/CH_2Cl_2$) to yield 203 mg of 3-Methyl-2-[4'-(3-methyl-quinolin-2-yloxymethyl)-biphenyl-4-sulfonylamino]-butyric acid methyl ester in 12% yield.

1H NMR (400 MHz, CHLOROFORM-D) δ ppm 0.89 (d, J=6.82 Hz, 3 H) 0.97 (d, J=6.82 Hz, 3 H) 2.04 (m, 1 H) 2.40 (s, 3 H) 3.43 (s, 3 H) 3.78 (dd, J=10.11, 5.31 Hz, 1 H) 5.09 (d, J=10.11 Hz, 1 H) 5.64 (s, 2 H) 7.37 (m, 1 H) 7.64 (m, 8 H) 7.86 (m, 4 H).

Step 1D: 3-Methyl-2-[4'-(3-methyl-quinolin-2-yloxymethyl)-biphenyl-4-sulfonylamino]-butyric acid methyl ester (203 mg, 0.39 mmol, 1 equiv.) was dissolved in THF (8 mL) and MeOH (4 mL) and hydrolyzed with 1N NaOH (5.83 mL, 5.83 mmol, 13 equiv.). After stirring for 3 days, solvent was removed and the residue was dissolved in $H_2O$. The mixture was then acidified to pH 3 using 1N HCl. Solid precipitated from the mixture was collected by filtration and washed with water. After drying in vacuum oven, 101 mg of 3-Methyl-2-[4'-(3-methyl-quinolin-2-yloxymethyl)-biphenyl-4-sulfonylamino]-butyric acid was obtained in 76.3% yield.

1H NMR (400 MHz, DMSO-D6) δ ppm 0.81 (d, J=6.57 Hz, 3 H) 0.84 (d, J=6.82 Hz, 3 H) 1.95 (m, 1 H) 2.36 (s, 3 H) 3.56 (dd, J=9.09, 5.81 Hz, 1 H) 5.61 (s, 2 H) 7.42 (t, J=7.45 Hz, 1 H) 7.61 (t, J=7.71 Hz, 1 H) 7.67 (d, J=7.83 Hz, 2 H) 7.83 (m, 8 H) 8.08 (d, J=8.34 Hz, 2 H) 12.58 (s, 1 H).

Example 1B

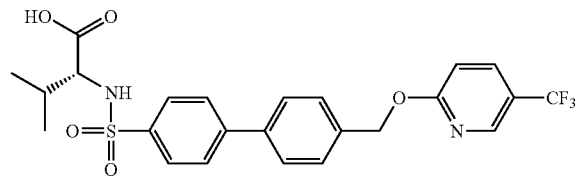

3-Methyl-2-[4'-(5-trifluoromethyl-pyridin-2-yloxymethyl)-biphenyl-4-sulfonylamino]-butyric acid The title compound, 3-Methyl-2-[4'-(5-trifluoromethyl-pyridin-2-yloxymethyl)-biphenyl-4-sulfonylamino]-butyric acid, was prepared according to the procedures similar to that described for Example 1A.

Step 1C: 2-(4'-Hydroxymethyl-biphenyl-4-sulfonylamino)-3-methyl-butyric acid methyl ester (350 mg, 0.93 mmol, 1 equiv), 2-chloro-5-trifluoromethylpyridine (841 mg, 4.64 mmol, 5 equiv.) were dissolved in DMF (7 mL) followed by the addition of NaH (111 mg, 2.78 mmol, 3 equiv.) under $N_2$ atmosphere. The mixture was heat to 100° C. for 2 hrs and cool to room temperature. Reaction mixture poured onto cold water and the resulting solid collected by filtration. Further purification by column chromatography (Silica gel, 20% EtOAc/Hexane) to afford 259 mg of G9058-182-2 in 54% yield.

1H NMR (400 MHz, CHLOROFORM-D) δ ppm 0.82 (d, J=6.82 Hz, 3 H) 0.90 (d, J=6.82 Hz, 3 H) 1.98 (m, 1 H) 3.36 (s, 3 H) 3.72 (dd, J=10.11, 5.05 Hz, 1 H) 5.02 (d, J=10.11 Hz, 1 H) 5.43 (s, 2 H) 6.84 (d, J=8.84 Hz, 1 H) 7.52 (m, 4 H) 7.64 (d, J=6.82 Hz, 2 H) 7.74 (d, J=8.84 Hz, 1 H) 7.82 (m, 2 H) 8.40 (s, 1 H).

Step 1D: 3-Methyl-2-[4'-(5-trifluoromethyl-pyridin-2-yloxymethyl)-biphenyl-4-sulfonylamino]-butyric acid (86.4% yield, 210 mg) was prepared according to procedures in Step 1D for Example 1A, using 3-Methyl-2-[4'-(5-trifluoromethyl-pyridin-2-yloxymethyl)-biphenyl-4-sulfonylamino]-butyric acid methyl ester (250 mg) as the starting material.

1H NMR (400 MHz, DMSO-D6) δ ppm 0.81 (d, J=6.82 Hz, 3 H) 0.84 (d, J=6.57 Hz, 3 H) 1.95 (m, 1 H) 3.56 (m, 1 H) 5.51 (d, 2 H) 7.12 (d, J=8.84 Hz, 1 H) 7.59 (d, J=8.34 Hz, 2 H) 7.77 (d, J=8.34 Hz, 2 H) 7.86 (m, 4 H) 8.11 (m, 2 H) 8.63 (m, 1 H) 12.57 (s, 1 H).

Example 1C and 1D were made based on Scheme 2.

Example 1C

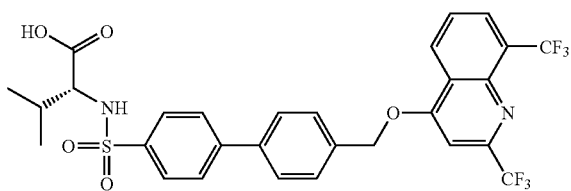

2-[4'-(2,8-Bis-trifluoromethyl-quinolin-4-yloxymethyl)-biphenyl-4-suffonylamino]-3-methyl-butyric acid Step 2A [Intermediate 4, G9591-157-1]: To a solution of 2,8-Bis-trifluoromethyl-quinolin-4-ol (3.85 g, 13.7 mmol, 1.1 equiv.) in DMF (40 mL) was added 2-(4-Bromomethyl-phenyl)-4,4,5,5-tetramethyl-[1,3,2]dioxaborolane (3.7 g, 12.5 mmol, 1.0 equiv.) and $K_2CO_3$ (3.45 g, 24.92 mmol, 2.2 equiv.) under $N_2$ atmosphere. The reaction mixture was stirred at room temperature overnight. The reaction was complete as determined by TLC. The reaction mixture was poured into cold water, the white precipitate formed was collected by filtration, washed with water, dried under vacuum to yield 4-[4-(4,4,5,5-Tetramethyl-[1,3,2]dioxaborolan-2-yl)-benzyloxy]-2,8-bis-trifluoromethyl-quinoline in 73% yield (4.95 g).

1H NMR (400 MHz, CHLOROFORM-D) δ ppm 1.36 (s, 12 H) 5.38 (s, 2 H) 7.21 (s, 1 H) 7.51 (d, J=8.34 Hz, 2 H) 7.65 (t, J=7.83 Hz, 1 H) 7.90 (d, J=8.08 Hz, 2 H) 8.14 (d, J=7.33 Hz, 1 H) 8.50 (d, J=8.59 Hz, 1 H).

Step 2B [Intermediate 5, G9591-162]: To 4-[4-(4,4,5,5-Tetramethyl-[1,3,2]dioxaborolan-2-yl)-benzyloxy]-2,8-bis-trifluoromethyl-quinoline (1.5 g, 3.0 mmol, 1 equiv.) in 45 mL of ethylene glycol dimethyl ether was added 2-(4-Bromo-benzenesulfonylamino)-3-methyl-butyric acid methyl ester (1.06 g, 3.0 mmol, 1.0 equiv.) and $Pd(PPh_3)_4$ (174 mg, 0.15 mmol, 0.05 equiv.) under $N_2$. The reaction mixture was stirred for 0.5 hr, then an aqueous solution of $K_2CO_3$ (834 mg, 6.0 mmol, 2 equiv.) was added. The mixture was heat to reflux overnight. After cooling to room temperature, solvent was removed under vacuum. The residue was diluted with EtOAc (100 mL) and washed with brine solution. The organic layer was dried over anhydrous $MgSO_4$, solvent evaporated under vacuum, and the crude product was purified on silica gel column (30% EtOAc/Hexane) to give 1.026 g of 2-[4'-(2,8-Bis-trifluoromethyl-quinolin-4-yloxymethyl)-biphenyl-4-sulfonylamino]-3-methyl-butyric acid methyl ester in 53% yield.

1H NMR (400 MHz, CHLOROFORM-D) δ ppm 0.90 (d, J=6.82 Hz, 3 H) 0.98 (d, J=6.82 Hz, 3 H) 2.07 (m, 1 H) 3.45 (s, 3 H) 3.81 (dd, J=10.11, 5.05 Hz, 1 H) 5.12 (d, J=10.11 Hz, 1 H) 5.44 (s, 2 H) 7.25 (s, 1 H) 7.70 (m, 7 H) 7.92 (d, J=8.84 Hz, 2 H) 8.16 (d, J=7.33 Hz, 1 H) 8.52 (d, J=8.59 Hz, 1 H).

Step 2C: 2-[4'-(2,8-Bis-trifluoromethyl-quinolin-4-yloxymethyl)-biphenyl-4-sulfonylamino]-3-methyl-butyric acid methyl ester (1.026 g, 1.6 mmol, 1 equiv.) was dissolved in THF (15 mL) and MeOH (6 mL) and 1N NaOH (17.6 mL, 11 equiv.) was added. The reaction was monitored by TLC. It was complete in 3 days. Solvent was removed by rotovap and the residue was dissolved in $H_2O$. The mixture was then acidified to pH 3 with 1N HCl. The resulting precipitate was collected by filtration and washed with cold water and dried overnight. 460 mg of white solid was obtained in 46% yield.

1H NMR (400 MHz, DMSO-D6) δppm 0.82 (d, J=6.82 Hz, 3 H) 0.85 (d, J=6.82 Hz, 3 H) 1.96 (m, 1 H) 3.57 (dd, J=9.35, 6.32 Hz, 1 H) 5.66 (s, 2 H) 7.83 (m, 10 H) 8.11 (d, J=9.35 Hz, 1 H) 8.35 (d, J=7.33 Hz, 1 H) 8.58 (d, J=7.83 Hz, 1 H) 12.57 (s, 1 H).

Example 1D

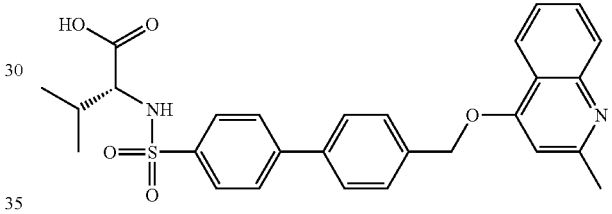

D-3-Methyl-2-[4'-(2-methyl-quinolin-4-yloxymethyl)-biphenyl-4-sulfonylamino]-butyric acid The title compound, D-3-Methyl-2-[4'-(2-methyl-quinolin-4-yloxymethyl)-biphenyl-4-sulfonylamino]-butyric acid, was prepared according to the procedures similar to that described for Example 1C.

Step 2A: Alkylation of 2-Methyl-quinolin-4-ol with 2-(4-Bromomethyl-phenyl)-4,4,5,5-tetramethyl-[1,3,2]dioxaborolane was carried out according to procedures in Step 2A for Example 1C to give 2-Methyl-4-[4-(4,4,5,5-tetramethyl-[1,3,2]dioxaborolan-2-yl)-benzyloxy]-quinoline in 28% yield. 1H NMR (400 MHz, DMSO-D6) δ ppm 1.3 (s, 12 H) 2.6 (s, 3 H) 5.4 (s, 2 H) 7.0 (s, 1 H) 7.5 (m, 1 H) 7.6 (d, J=8.1 Hz, 2 H) 7.7 (m, 1 H) 7.7 (d, J=8.1 Hz, 2 H) 7.9 (d, J=8.1 Hz, 1 H) 8.1 (dd, J=8.3, 0.8 Hz, 1 H).

Step 2B: Suzuki coupling of D-2-(4-Bromo-benzenesulfonylamino)-3-methyl-butyric acid methyl ester with 2-Methyl-4-[4-(4,4,5,5-tetramethyl-[1,3,2]dioxaborolan-2-yl)-benzyloxy]-quinoline was carried out according to procedures in Step 2B for Example 1C in 80% yield. 1H NMR (400 MHz, DMSO-D6) δ ppm 0.8 (dd, J=15.0, 6.7 Hz, 6 H) 1.9 (m, 1 H) 2.6 (s, 3 H) 3.3 (s, 3 H) 3.6 (dd, J=9.3, 7.1 Hz, 1 H) 5.5 (s, 2 H) 7.1 (s, 1 H) 7.5 (t, J=7.6 Hz, 1 H) 7.7 (m, 3 H) 7.8 (d, J=7.6 Hz, 4 H) 7.9 (m, 1 H) 7.9 (m, 2 H) 8.1 (d, J=8.3 Hz, 1 H) 8.3 (d, J=9.3 Hz, 1 H).

Step 2C: Hydrolysis of D-3-Methyl-2-[4'-(2-methyl-quinolin-4-yloxymethyl)-biphenyl-4-sulfonylamino]-butyric acid methyl ester was carried out according to procedures in Step 2C for Example 1C in quantitative yield. 1H NMR (400 MHz, DMSO-D6) δ ppm 0.8 (dd, J=40.2, 6.8 Hz, 6 H) 2.0 (m, 1 H) 2.6 (s, 3 H) 3.0 (s, 1 H) 5.4 (s, 2 H) 7.1 (s, 1 H) 7.5 (t, J=8.1 Hz, 1 H) 7.7 (t, J=7.7 Hz, 3 H) 7.8 (m, 7 H) 8.1 (d, J=9.3 Hz, 1 H).

Example 1E was made based on Scheme 3.

Example 1E

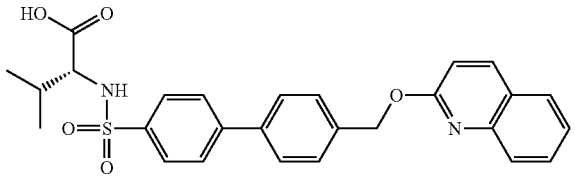

Step 3A. To a round-bottom flask was added 4-Bromo-benzenesulfonyl chloride (24.37 g, 95.4 mmol, 1 equiv), anhydrous methylene chloride (350 mL), and H-D-Val-OtBu (20 g, 95.4 mmol, 1 equiv.). The mixture was cool to 0° C. followed by the addition of Hunig's base (38.2 mL, 219 mmol, 2.3 equiv.). The cooling bath was then removed and the reaction mixture was allowed to warm to room temperature and stirred overnight. Starting material was consumed as determined by TLC. The reaction mixture was then diluted with methylene chloride (200 mL) and washed with $H_2O$ (500 mL), brine (250 mL). The organic layer was dried over anhydrous $MgSO_4$, evaporated under vacuum to yield 2-(4-Bromo-benzenesulfonylamino)-3-methyl-butyric acid tert-butyl ester in quantitative yield (35.0 g).

1H NMR (400 MHz, DMSO-D6) δ ppm 0.82 (d, J=6.82 Hz, 3 H) 0.84 (d, J=6.82 Hz, 3 H) 1.19 (s, 9 H) 1.93 (m, 1 H) 3.46 (dd, J=9.35, 6.06 Hz, 1 H) 7.69 (d, J=8.59 Hz, 2 H) 7.79 (m, 2 H) 8.24 (d, J=9.60 Hz, 1 H).

Step 3B: 2-(4-Bromo-benzenesulfonylamino)-3-methyl-butyric acid tert-butyl ester (11.96 g, 30.47 mmol, 1 equiv.), 4-(Hydroxymethylbenzene) boronic acid (4.63 g, 30.5 mmol, 1 equiv) and $Pd(PPh_3)_4$ (1.76 g, 1.52 mmol, 0.05 equiv.) were charged to a reaction flask and added with ethylene glycol dimethyl ether (300 mL). The mixture was stirred at room temperature for 10 min., then a solution of $K_2CO_3$ (8.43 g, 60.9 mmol, 2 equiv.) dissolved in 100 mL $H_2O$ was introduced. The reaction mixture was heat to reflux overnight. After cooling to room temperature, solvent was removed by rotavap and the residue partitioned between EtOAc and brine. Organic layer was separated and dried over $MgSO_4$. After removing solvent by rotavap, 8.3 g of white solid 2-(4'-Hydroxymethyl-biphenyl-4-sulfonylamino)-3-methyl-butyric acid tert-butyl ester was obtained in 65% yield.

1H NMR (400 MHz, MeOD) δ ppm 1.05 (d, J=6.82 Hz, 3 H) 1.12 (d, J=6.82 Hz, 3 H) 1.33 (s, 9 H) 2.16 (m, 1 H) 3.73 (d, J=5.56 Hz, 1 H) 4.81 (s, 2 H) 7.62 (d, J=8.59 Hz, 2 H) 7.78 (d, J=8.34 Hz, 2 H) 7.92 (d, J=8.84 Hz, 2 H) 8.04 (m, 2 H).

Step 3C 2-(4'-Hydroxymethyl-biphenyl-4-sulfonylamino)-3-methyl-butyric acid tert-butyl ester (700 mg, 1.68 mmol, 1 equiv), 2-chloroquinoline (1.1 g, 6.7 mmol, 4 equiv) were dissolved in DMF (20 mL) and added with and NaH (202 mg,60% in oil, 5.04 mmol, 3 equiv). The mixture was heat to 100° C. for 2 hrs. After cooling to room temperature, the reaction mixture was quenched with sat. $NH_4Cl$ (aq). After stirring for 0.5 h, solid precipitated from the mixture. Solid was collected by filtration and washed with water and dried overnight to produce 793 mg of 2-[4'-(Isoquinolin-3-yloxymethyl)-biphenyl-4-sulfonylamino]-3-methyl-butyric acid tert-butyl ester in 87% yield.

1H NMR (400 MHz, CHLOROFORM-D) δ ppm 0.87 (d, J=6.82 Hz, 3 H) 1.03 (d, J=6.82 Hz, 3 H) 1.19 (s, 9 H) 2.05 (m, 1 H) 3.66 (dd, J=9.85, 4.55 Hz, 1 H) 5.14 (d, J=9.85 Hz, 1 H) 5.62 (s, 2 H) 6.98 (d, J=8.84 Hz, 1 H) 7.40 (m, 1 H) 7.66 (m, 9 H) 7.89 (m, 2 H) 8.03 (d, J=8.59 Hz, 1 H).

Step 3D: 2-[4'-(Isoquinolin-3-yloxymethyl)-biphenyl-4-sulfonylamino]-3-methyl-butyric acid tert-butyl ester (480 mg, 0.88 mmol) was dissolved in 15 mL of dichloromethane. The solution was cool to 0° C. followed by the addition of 5 nL of TFA. The resulting mixture was stirred at room temperature for 4 hrs. Solvent was removed by rotavap and the residue was washed with MeOH. Solid thus obtained was dried overnight under vacuum to afford 60 mg of 2-[4'-(Isoquinolin-3-yloxymethyl)-biphenyl-4-sulfonylamino]-3-methyl-butyric acid in 14% yield.

1H NMR (400 MHz, DMSO-D6) δ ppm 0.81 (d, J=6.82 Hz, 3 H) 0.84 (d, J=6.82 Hz, 3 H) 1.95 (m, 1 H) 3.56 (dd, J=9.35, 6.06 Hz, 1 H) 5.58 (s, 2 H) 7.11 (d, J=8.84 Hz, 1 H) 7.46 (dd, J=7.58, 6.32 Hz, 1 H) 7.79 (m, 11 H) 8.08 (d, J=9.35 Hz, 1 H) 8.29 (d, J=8.59 Hz, 1 H) 12.57 (s, 1 H).

Example 1F was made based on Scheme 4.

Example 1F

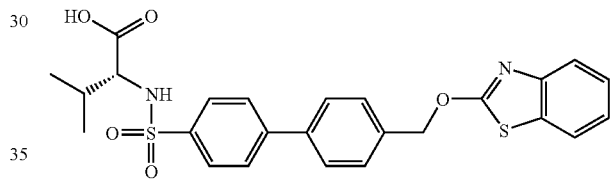

2-[4'-(Benzothiazol-2-yloxymethyl)-biphenyl-4-sulfonylamino]-3-methyl-butyric acid To 2-[4-(4,4,5,5-tetramethyl-[1,3,2]dioxaborolan-2-yl)-benzyloxy]-benzothiazole (300 mg, 0.604 mmol, 1 equiv.) in 9 mL of dimethoxy ethane was added 2-(4-Bromo-benzenesulfonylamino)-3-methyl-butyric acid tert-butyl ester (237 mg, 0.604 mmol, 1 equiv) and Pd(PPh3)4 (35 mg, 0.03 mmol, 0.05 equiv). The mixture was stirred at room temperature for 20 min followed by the addition of K2CO3 (167 mg, 1.208 mmol, 2 equiv.) in H2O (3 mL). The mixture was heat to reflux overnight. After cooling to room temperature, solvent was removed by rotavap. Residue was dissolved in methylene chloride and washed with water, brine. Organic layer dried over $MgSO_4$, solvent removed under vacuum, crude mixture purified by column chromatography (30% EtOAc/Hexane) to give 285 mg of in 85% yield.

1H NMR (400 MHz, CHLOROFORM-D) δ ppm 1.07 (d, J=6.82 Hz, 3 H) 1.23 (d, J=6.82 Hz, 3 H) 1.39 (s, 9 H) 1.47 (t, J=7.20 Hz, 1 H) 3.86 (dd, J=9.85, 4.55 Hz, 1 H) 5.42 (s, 2 H) 6.99 (s, 1 H) 7.22 (d, J=7.07 Hz, 1 H) 7.39 (m, 2 H) 7.61 (d, J=8.59 Hz, 2 H) 7.67 (d, J=6.32 Hz, 1 H) 7.72 (m, 2 H) 7.84 (d, J=8.84 Hz, 2 H) 8.09 (d, J=8.59 Hz, 2 H).

Step 4B 2-[4'-(Benzothiazol-2-yloxymethyl)-biphenyl-4-sulfonylamino]-3-methyl-butyric acid tert-butyl ester (140 mg, 0.25 mml) was dissolved in 6 mL of methylene chloride followed by the addition of TFA (3 mL) The reaction was complete in 6 hrs as determined by TLC. Solvent was removed and the residue was dissolved in EtOAc. n-Hexane was added into the solution and solid precipitated from the mixture. The precipitate was collected and dried to afford 86 mg of in 68% yield.

1H NMR (400 MHz, DMSO-D6) δ ppm 0.80 (d, J=6.82 Hz, 3 H) 0.83 (d, J=6.82 Hz, 3 H) 1.93 (m, 1 H) 3.54 (dd, J=9.35, 6.06 Hz, 1 H) 5.26 (s, 2 H) 7.21 (m, 1 H) 7.33 (m, 2 H) 7.44 (d, J=8.59 Hz, 2 H) 7.71 (t, J=8.46 Hz, 3 H) 7.82 (s, 4 H) 8.07 (d, J=9.35 Hz, 1 H) 12.55 (s, 1 H).

Examples 1G, 1H, 1I, 1J, 1K, 1L, 1M, 1N, 1O, 1P, 1Q, 1R were made based on Scheme 4B.

Example 1G

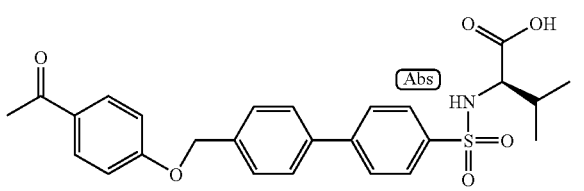

ES− 480.1 (M−H)−HRMS: 482.16311 (M+Na)+; 482.16319 Calc'd

Example 1H

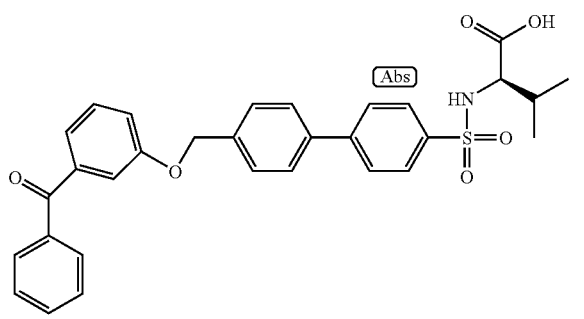

ES+ 544.2 (M+H)+HRMS: 544.17694 (M+H); 544.17884 Calc'd

Example 1I

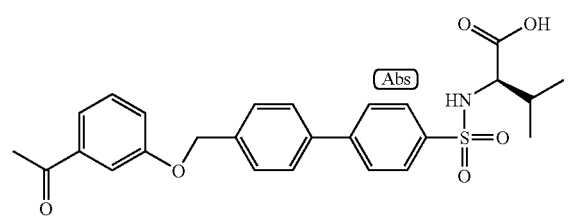

ES− 480.2 (M−H)−HRMS: 482.1635 (M+H)+; 482.16319 Calc'd

Example 1J

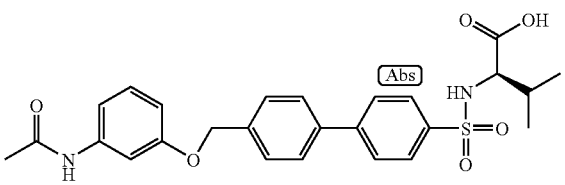

ES− 495.2 (M−H)−HRMS: 497.17284 (M+H)+; 497.17409 Calc'd

Example 1K

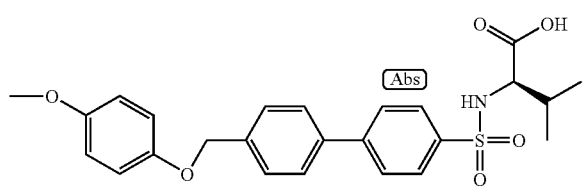

ES− 468.2 (M−H)−HRMS: 470.16231 (M+H)+; 470.16319 Calc'd

Example 1L

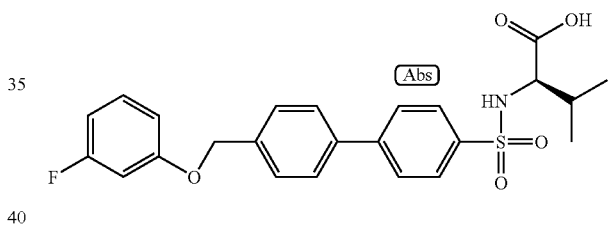

ES− 456.1 (M−H)−HRMS: 458.14323 (M+H)+; 458.1432 Calc'd

Example 1M

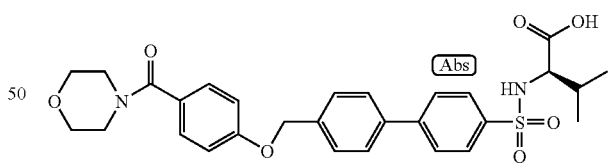

ES− 551.2 (M−H)−HRMS: 553.19849 (M+H)+; 553.2003 Calc'd

Example 1N

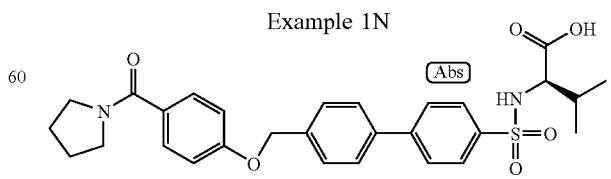

ES− 535.2 (M−H)−HRMS: 537.20469 (M+H)+; 537.20539 Calc'd

Example 1O

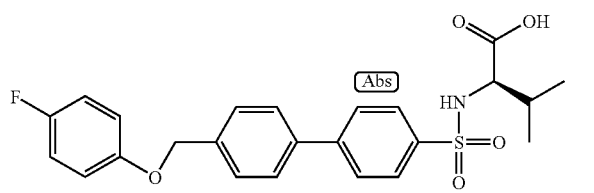

ES– 456.1 (M–H)–HRMS: 458.14389 (M+H)+; 458.1432 Calc'd

Example 1P

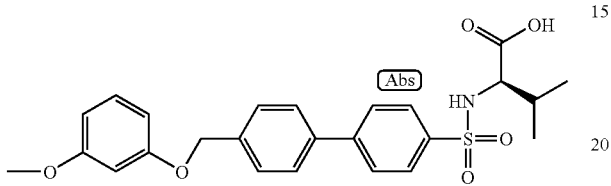

ES– 468.2 (M–H)–HRMS: 470.16151 (M+H)+; 470.16319 Calc'd

Example 1Q

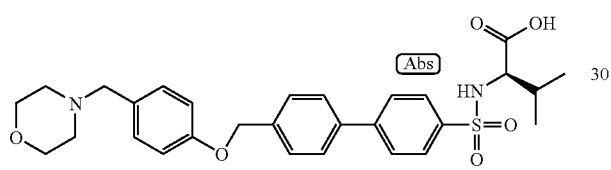

ES+539.1 (M+H)+HRMS: 539.22021 (M+H)+; 539.22104 Calc'd

Example 1R

ES– 514.1 (M–H)–HRMS: 516.18313 (M+H)+; 516.18392 Calc'd

Examples 1S, 1T, 1U, 1V, 1W, 1X, 1Y, 1Z, 1AA, 1AB, 1AC, 1AD, 1AE were made based on Scheme 4C.

Example 1S

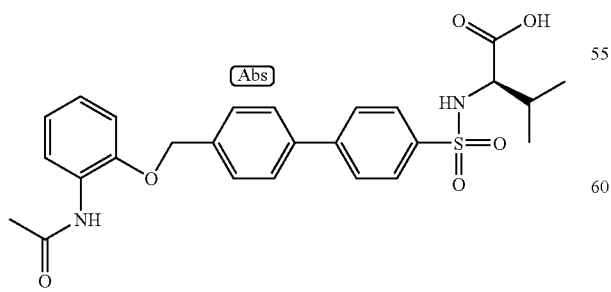

ES– 495.1 (M–H)–HRMS: 497.17429 (M+H)+; 497.17409 Calc'd

Example 1T

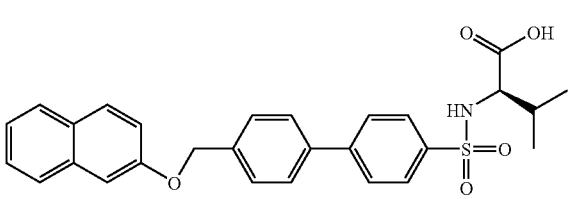

ES– 488.1 (M–H)–HRMS: 490.16864 (M+H)+; 490.16827 Calc'd

Example 1U

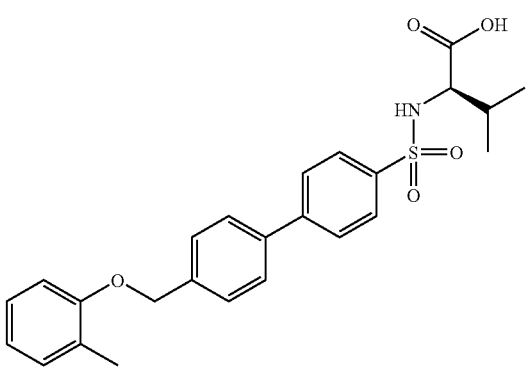

ES+ m/z 452.1 (M–H)–HRMS: 454.16745 (M+H)+; 454.16827 Calc'd $^1$H NMR (400 MHz, CDCl$_3$): δ 0.82 (d, 3H, J=6.8 Hz), 0.94 (d, 3H, J=6.8 Hz), 2.06 (m, 1H), 2.31 (s, 3H), 3.80 (dd, 1H, J=4.4, 10 Hz), 5.13 (m, 3H), 6.90 (m, 2H), 7.17 (m, 2H), 7.55 (d, 2H, J=8 Hz), 7.60 (d, 2H, J=8 Hz), 7.66 (d, 2H, J=8 Hz), 7.86 (d, 2H, J=8 Hz).

Example 1V

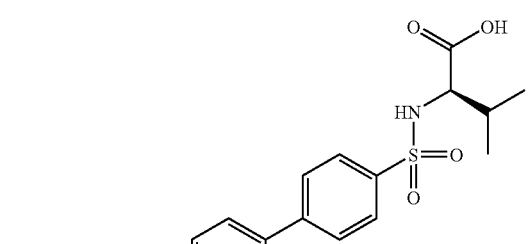

ES+ m/z 481.2 (M+H)+HRMS: 483.19410 (M+H)+; 483.19482 Calc'd $^1$H NMR (400 MHz, CD$_3$OD): δ 0.90 (d, 3H, J=6.8 Hz), 0.99 (d, 3H, J=6.8 Hz), 2.06 (m, 1H), 2.92 (s, 6H), 3.42 (s, 3H), 3.70 (d, 1H, J=5.6, 10 Hz), 5.14 (s, 2H), 6.41 (m, 3H), 7.11 (m, 1H), 7.57 (d, 2H, 8 Hz), 7.71 (d, 2H, J=8 Hz), 7.80 (d, 2H, J=8 Hz), 7.92 (d, 2H, J=8 Hz).

Example 1W

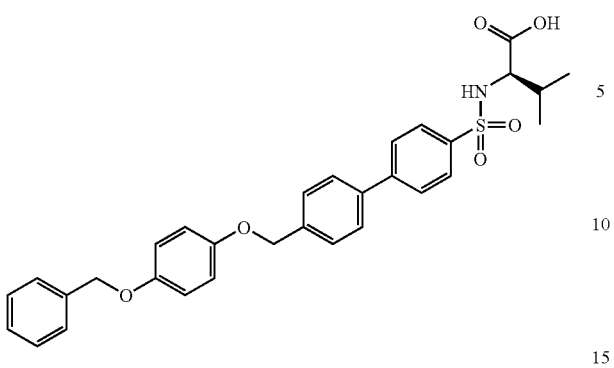

ES+ m/z 544.1 (M+H)+HRMS: 546.19448 (M+H)+; 546.19449 Calc'd $^1$H NMR (400 MHz, CD$_3$OD): δ 0.93 (d, 3H, J=6.8 Hz), 0.99 (d, 3H, J=6.8 Hz), 2.07 (m, 1H), 3.70 (d, 1H, J=5.6), 5.03 (s, 2H), 5.10 (s, 2H), 6.94 (s, 4H), 7.31 (m, 1H), 7.37 (m, 2H), 7.43 (m, 2H), 7.55 (d, 2H, 8 Hz), 7.71 (d, 2H, J=8 Hz), 7.80 (d, 2H, J=8 Hz), 7.92 (d, 2H, J=8 Hz).

Example 1X

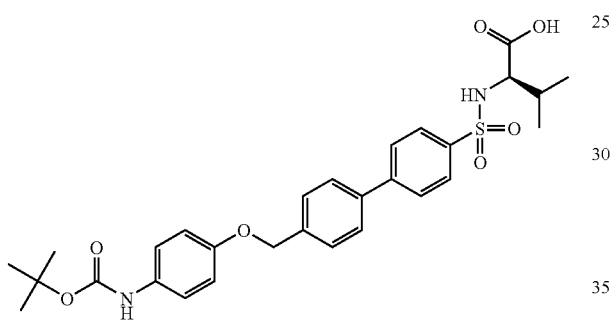

ES+ m/z 553.2 (M−H)−HRMS: 577.19777 (M+Na)+; 577.19789 Calc'd $^1$H NMR (400 MHz, CD$_3$OD): δ 0.91 (d, 3H, J=6.8 Hz), 0.97 (d, 3H, J=6.8 Hz), 1.50 (s, 9H), 2.04 (m, 1H), 3.68 (d, 1H, J=5.6 Hz), 5.10 (s, 2H), 6.92 (s, 2H), 7.28 (d, 2H, J=8 Hz), 7.54 (d, 2H, J=8 Hz), 7.70 (d, 2H, J=8 Hz), 7.79 (d, 2H, J=8 Hz), 7.91 (d, 2H, J=8 Hz).

Example 1Y

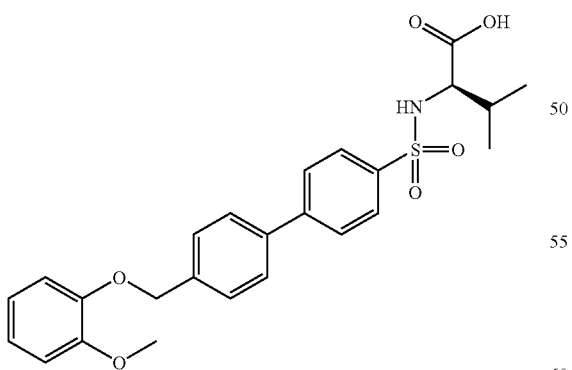

ES+ m/z 470.2 (M+H)+HRMS: 470.16364 (M+H)+; 470.16319 Calc'd $^1$H NMR (400 MHz, CDCl$_3$): δ 0.89 (d, 3H, J=6.8 Hz), 0.96 (d, 3H, J=6.8 Hz), 2.10 (m, 1H), 3.82 (m, 1H), 3.90 (s, 3H), 5.07 (d, 1H, J=9.6 Hz), 5.21 (s, 2H), 6.93 (m, 4H), 7.54 (d, 2H, J=8 Hz), 7.58 (d, 2H, J=8 Hz), 7.65 (d, 2H, J=8 Hz), 7.89 (d, 2H, J=8 Hz).

Example 1Z

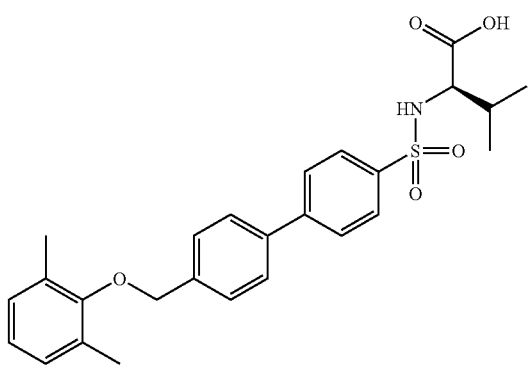

ES+ m/z 466.2 (M−H)−HRMS: 468.18540 (M+H)+; 468.18392 Calc'd $^1$H NMR (400 MHz, CDCl$_3$): δ 0.83 (d, 3H, J=6.8 Hz), 0.95 (d, 3H, J=6.8 Hz), 2.05 (m, 1H), 2.33 (s, 6H), 3.82 (dd, 1H, J=5.2, 10 Hz), 4.88 (s, 2H), 5.07 (d, 1H, J=10 Hz), 6.97 (m, 1H), 7.05 (m, 2H), 7.64 (m, 4H), 7.67 (d, 2H, J=8 Hz), 7.87 (d, 2H, J=8 Hz).

Example 1AA

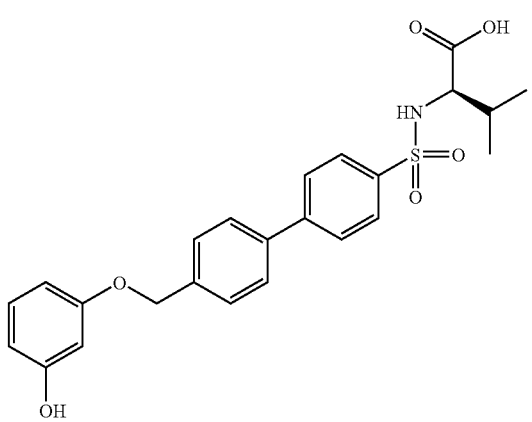

ES+ m/z 454.1 (M−H)−HRMS: 456.14707 (M+H)+; 456.14754 Calc'd $^1$H NMR (400 MHz, acetone(d$_6$)): δ 0.92 (d, 3H, J=6.8 Hz), 0.98 (d, 3H, J=6.8 Hz), 2.10 (m, 1H), 3.16 (m, 1H), 5.16 (s, 2H), 6.45 (d, 1H, J=8 Hz), 6.53 (m, 2H), 7.10 (t, 1H, J=8 Hz), 7.61 (d, 2H, J=8 Hz), 7.76 (d, 2H, J=8 Hz), 7.86 (d, 2H, J=8 Hz), 7.94 (d, 2H, J=8 Hz).

Example 1AB

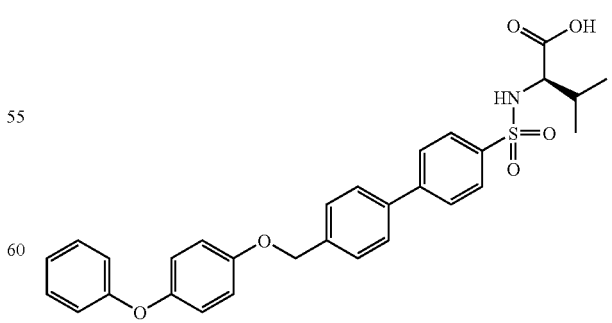

ES+ m/z 530.1 (M−H)−HRMS: 532.17709 (M+H)+; 532.17884 Calc'd $^1$H NMR (400 MHz, CD$_3$OD): δ 0.93 (d, 3H, J=6.8 Hz), 0.99 (d, 3H, J=6.8 Hz), 2.06 (m, 1H), 3.70

(d, 1H, J=5.6, 10 Hz), 5.16 (s, 2H), 6.93 (m, 3H), 7.04 (m, 3H), 7.31 (m, 2H), 7.58 (d, 2H, J=8 Hz), 7.72 (d, 2H, J=8 Hz), 7.81 (d, 2H, J=8 Hz), 7.93 (d, 2H, J=8 Hz).

Example 1AC

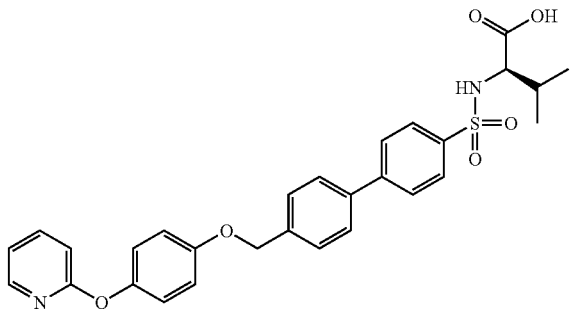

ES$^+$ m/z 531.1 (M−H)−HRMS: 533.17293 (M+H)+; 533.17409 Calc'd $^1$H NMR (400 MHz, CDCl$_3$): δ 0.88 (d, 3H, J=6.8 Hz), 1.00 (d, 3H, J=6.8 Hz), 2.13 (m, 1H), 3.83 (m, 1H), 5.13 (m, 3H), 6.82 (m, 1H), 7.02 (m, 5H), 7.56 (m, 4H), 7.67 (m, 3H), 7.89 (m, 2H), 8.16 (m, 1H).

Example 1AD

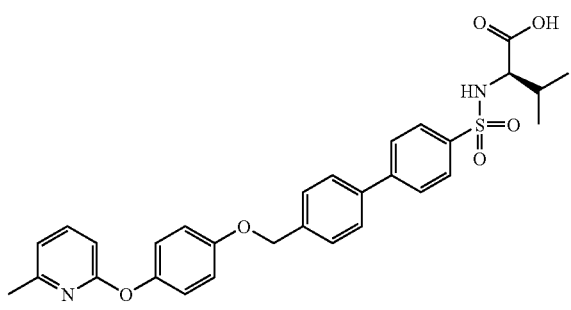

ES$^+$ m/z 545.2 (M−H)−HRMS: 547.19006 (M+H)+; 547.18974 Calc'd $^1$H NMR (400 MHz, CDCl$_3$): δ 0.89 (d, 3H, J=6.8 Hz), 1.01 (d, 3H, J=6.8 Hz), 2.19 (m, 1H), 2.44 (s, 3H), 3.83 (m, 1H), 5.04 (s, 2H), 6.39 (d, 1H, J=8 Hz), 6.83 (m, 1H), 6.90 (m, 2H, J=8 Hz), 6.97 (d, 2H, J=8 Hz), 7.52 (m, 5H), 7.60 (d, 2H, J=8 Hz), 7.90 (d, 2H, J=8 Hz).

Example 1AE

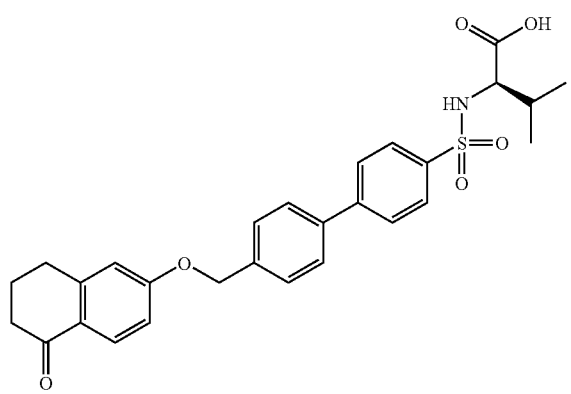

ES$^+$ m/z 506.2 (M−H)−HRMS: 508.17782 (M+H)+; 508.17884 Calc'd $^1$H NMR (400 MHz, DMSO): δ 0.81 (d, 3H, J=6.8 Hz), 0.84 (d, 3H, J=6.8 Hz), 1.98 (m, 3H), 2.64 (d, 2H), 2.91 (t, 2H, J=6 Hz), 3.56 (dd, 1H, J=6, 9.2 Hz), 5.27 (s, 2H), 6.99 (d, 2H, J=8 Hz), 7.59 (d, 2H, J=8 Hz), 7.78 (d, 2H, J=8 Hz), 7.85 (m, 4H), 8.08 (d, 1H, 8 Hz).

Examples 2A, 2B, 2C, 2D, 2E, 2F, 2G, 2H, 2I, 2J were made based on Scheme 5.

Example 2A

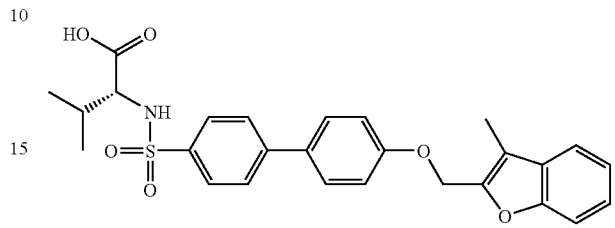

D-3-Methyl-2-[4'-(3-methyl-benzofuran-2-yl-methoxy)-biphenyl-4-sulfonylamino]-butyric acid Step 5A: A mixture of 2-Chloromethyl-3-methyl-benzofuran (675.9 mg, 3.75 mmol), 4-(4,4,5,5-Tetramethyl-[1,3,2]dioxaborolan-2-yl)-phenol (825 mg, 3.75 mmol, 1 eq), K$_2$CO$_3$ (2.1 g, 15.2 mmol, 4 eq) in 20 mL of CH$_3$CN was heat to reflux under nitrogen atmosphere. Reaction was complete after 12 hrs. Regular work-upwork up and column purification (5% EtOAc/hexane) to give 3-Methyl-2-[4-(4,4,5,5-tetramethyl-[1,3,2]dioxaborolan-2-yl)-phenoxymethyl]-benzofuran in 44% yield (601 mg). 1H NMR (400 MHz, CHLOROFORM-D) δ ppm 1.3 (s, 12 H) 2.3 (s, 3 H) 5.2 (s, 2 H) 7.0 (d, J=8.6 Hz, 2 H) 7.3 (m, 2 H) 7.5 (dd, J=21.6, 7.7 Hz, 2 H) 7.8 (d, J=8.8 Hz, 2 H).

Step 5B: A mixture of D-2-(4-Bromo-benzenesulfonylamino)-3-methyl-butyric acid methyl ester (568.07 mg, 1.62 mmol), 3-Methyl-2-[4-(4,4,5,5-tetramethyl-[1,3,2]dioxaborolan-2-yl)-phenoxymethyl]-benzofuran (590.7 mg, 1.62 mmol, 1 eq), Pd(PPh$_3$)$_4$ (93.7 mg, 0.08 mmol, 0.05 eq), and K$_2$CO$_3$ (448.35 mg, 3.24 mmol, 2 eq) in 5 mL of DME mL of H$_2$O was heat to reflux for 12 hrs. After cool to room temperature, the mixture was loaded onto column for purification. 616 mg of product G8475-146 was obtained in 75% yield. 1H NMR (400 MHz, MeOD) δ ppm 0.8 (d, J=6.8 Hz, 6 H) 1.9 (m, 1 H) 2.2 (s, 3 H) 3.2 (s, 3 H) 3.5 (d, J=6.6 Hz, 1 H) 5.1 (s, 2 H) 7.0 (m, J=9.1 Hz, 2 H) 7.1 (m, 1 H) 7.2 (m, 1 H) 7.3 (m, 1 H) 7.4 (m, 1 H) 7.5 (d, J=9.1 Hz, 2 H) 7.6 (d, J=8.8 Hz, 2 H) 7.7 (m, 2 H).

Step 5C: To D-3-Methyl-2-[4'-(3-methyl-benzofuran-2-ylmethoxy)-biphenyl-4-sulfonylamino]-butyric acid methyl ester (364 mg) was dissolved in THF (10 mL) and MeOH (3 mL). 1N LiOH (3 mL) was added and the mixture was stirred overnight. Regular work-up and column purification to give D-3-Methyl-2-[4'-(3-methyl-benzofuran-2-yl-methoxy)-biphenyl-4-sulfonylamino]-butyric acid in quantitative. 1H NMR (400 MHz, MeOD) δ ppm 0.8 (dd, J=30.3, 6.8 Hz, 6 H) 2.0 (m, 1 H) 2.2 (s, 3 H) 3.5 (d, J=5.3 Hz, 1 H) 5.1 (s, 2 H) 7.1 (d, J=9.1 Hz, 2 H) 7.1 (m, 1 H) 7.2 (m, 1 H) 7.3 (d, J=8.3 Hz, 1 H) 7.5 (d, J=8.3 Hz, 1 H) 7.5 (d, J=9.1 Hz, 3 H) 7.6 (d, J=8.6 Hz, 2 H) 7.8 (d, J=8.8 Hz, 2 H).

Example 2B

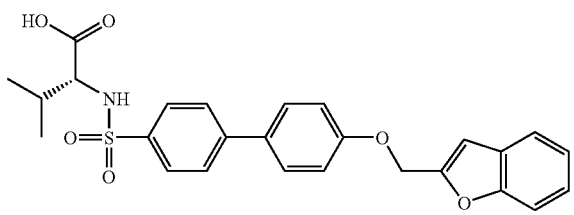

D-2-[4'-(Benzofuran-2-ylmethoxy)-biphenyl-4-sulfonylamino]-3-methyl-butyric acid The title compound, D-2-[4'-(Benzofuran-2-ylmethoxy)-biphenyl-4-sulfonylamino]-3-methyl-butyric acid, was prepared according to procedures similar to that of Example 2A.

Step 5A: To 2-Bromomethyl-benzofuran (1.5 g, 7.1 mmol, 1 eq.), 4-(4,4,5,5-Tetramethyl-[1,3,2]dioxaborolan-2-yl)-phenol (1.56 g, 7.1 mmol, 1 eq.), potassium carbonate (1.96 g, 14.2 mmol, 2 eq.) was dissolved in acetonitrile (50 mL) under argon and heated at 70° C. for 16 hours. After work-up and flash column chromatography, 2-[4-(4,4,5,5-Tetramethyl-[1,3,2]dioxaborolan-2-yl)-phenoxymethyl]-benzofuran is obtained. Yield: 63%. 1H NMR (400 MHz, DMSO-D6) δ ppm 1.3 (s, 12 H) 5.3 (s, 2 H) 7.1 (m, 3 H) 7.3 (m, 1 H) 7.3 (m, 1 H) 7.6 (m, 4H).

Step 5B: Coupling of 2-[4-(4,4,5,5-Tetramethyl-[1,3,2]dioxaborolan-2-yl)-phenoxymethyl]-benzofuran with D-2-(4-Bromo-benzenesulfonylamino)-3-methyl-butyric acid tert-butyl ester to obtain D-2-[4'-(Benzofuran-2-ylmethoxy)-biphenyl-4-sulfonylamino]-3-methyl-butyric acid tert-butyl ester was done according to procedures in Step 5B for Example 2A. Yield: 33%. 1H NMR (400 MHz, DMSO-D6) δ ppm 0.8 (dd, J=8.3, 7.1 Hz, 6 H) 1.2 (s, 9 H) 1.9 (m, 1 H) 3.5 (dd, J=9.7, 6.2 Hz, 1 H) 5.3 (s, 2 H) 7.1 (s, 1 H) 7.2 (d, J=8.6 Hz, 2 H) 7.3 (m, 1 H) 7.3 (m, 1 H) 7.6 (dd, J=8.2, 0.6 Hz, 1 H) 7.7 (m, 3 H) 7.8 (d, J=3.3 Hz, 4 H) 8.1 (d, J=9.9 Hz, 1 H).

Step 5C: D-2-[4'-(Benzofuran-2-ylmethoxy)-biphenyl-4-sulfonylamino]-3-methyl-butyric acid tert-butyl ester (126 mg, 0.23 mmol, 1 eq.), cerium chloride heptahydrate (175 mg, 0.47 mmol, 2 eq.), potassium iodide (51 mg, 0.30 mmol, 1.3 eq.) in acetonitrile (10 mL) were heated at 70C for 16 hours. After work-up and flash column chromatography, D-2-[4'-(Benzofuran-2-ylmethoxy)-biphenyl-4-sulfonylamino]-3-methyl-butyric acid was obtained. Yield: 25%. NMR: 1H NMR (400 MHz, DMSO-D6) δ ppm 0.8 (dd, J=12.5, 6.7 Hz, 6 H) 2.0 (m, 1 H) 3.5 (dd, J=9.2, 5.9 Hz, 1 H) 5.3 (s, 2 H) 7.1 (s, 1 H) 7.2 (d, J=8.8 Hz, 2 H) 7.3 (dd, J=8.1, 0.8 Hz, 1 H) 7.3 (m, 1 H) 7.6 (d, J=8.1 Hz, 1 H) 7.7 (m, 1 H) 7.7 (d, J=8.8 Hz, 2 H) 7.8 (d, 4 H) 8.0 (d, J=9.3 Hz, 1 H).

Example 2C

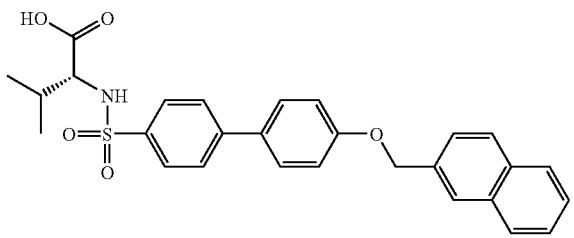

D-3-Methyl-2-[4'-(naphthalen-2-ylmethoxy)-biphenyl-4-sulfonylamino]-butyric acid The title compound, D-3-Methyl-2-[4'-(naphthalen-2-ylmethoxy)-biphenyl-4-sulfonylamino]-butyric acid, was prepared according to procedures similar to that of Example 2A.

Step 5A: Alkylation of 2-Bromomethyl-naphthalene with 4-(4,4,5,5-Tetramethyl-[1,3,2]dioxaborolan-2-yl)-phenol was carried out according to procedures in Step 5A in Example 2A to give 4,4,5,5-Tetramethyl-2-[4-(naphthalen-2-ylmethoxy)-phenyl]-[1,3,2]dioxaborolane in 85% yield. 1H NMR (400 MHz, CHLOROFORM-D) δ ppm 1.3 (s, 12 H) 5.3 (s, 2 H) 7.0 (d, J=8.6 Hz, 2 H) 7.5 (m, 2 H) 7.5 (dd, J=8.3, 1.8 Hz, 1 H) 7.8 (d, J=8.6 Hz, 2 H) 7.9 (m, 4 H).

Step 5B: Suzuki coupling of 4,4,5,5-Tetramethyl-2-[4-(naphthalen-2-ylmethoxy)-phenyl]-[1,3,2]dioxaborolane with D-2-(4-Bromo-benzenesulfonylamino)-3-methyl-butyric acid methyl ester was carried out according to procedures in Step 5B for Example 2A to give D-3-Methyl-2-[4'-(naphthalen-2-ylmethoxy)-biphenyl-4-sulfonylamino]-butyric acid methyl ester in 44% yield. 1H NMR (400 MHz, CHLOROFORM-D) δ ppm 0.9 (dd, J=32.1, 6.8 Hz, 6 H) 2.0 (m, 1 H) 3.4 (s, 3 H) 3.8 (dd, J=10.2, 5.2 Hz, 1 H) 5.1 (d, J=10.1 Hz, 1 H) 5.3 (s, 2 H) 7.1 (d, J=9.1 Hz, 2 H) 7.5 (m, 2 H) 7.6 (m, 3 H) 7.7 (d, J=8.6 Hz, 2 H) 7.9 (m, 6 H).

Step 5C: Hydrolysis of D-3-Methyl-2-[4'-(naphthalen-2-ylmethoxy)-biphenyl-4-sulfonylamino]-butyric acid methyl ester was carried out according to procedures in Step 5C for Example 2A in quantitative yield. 1H NMR (400 MHz, MeOD) δ ppm 0.8 (dd, J=32.6, 6.8 Hz, 6 H) 1.9 (m, 1 H) 3.5 (d, J=5.3 Hz, 1 H) 5.2 (s, 2 H) 7.1 (d, J=8.8 Hz, 2 H) 7.4 (m, 2 H) 7.5 (dd, J=8.6, 1.8 Hz, 1 H) 7.5 (d, J=8.8 Hz, 2 H) 7.6 (d, J=8.8 Hz, 2 H) 7.8 (m, 5 H) 7.8 (s, 1 H).

Example 2D

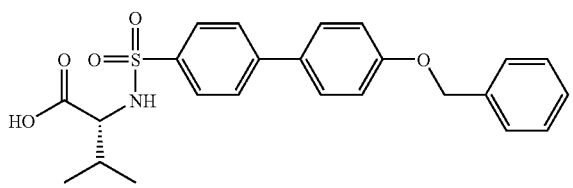

D-2-(4'-Benzyloxy-biphenyl-4-sulfonylamino)-3-methyl-butyric acid

The title compound, D-2-(4'-Benzyloxy-biphenyl-4-sulfonylamino)-3-methyl-butyric acid, was prepared according to procedures similar to that of Example 2A.

Step 5B: Suzuki coupling of 4-benzyloxyphenylboronic acid with D-2-(4-Bromo-benzenesulfonylamino)-3-methyl-butyric acid tert-butyl ester was carried out according to procedures in Step 5B for Example 2A to give D-2-(4'-Benzyloxy-biphenyl-4-sulfonylamino)-3-methyl-butyric acid tert-butyl ester in 73% yield. 1H NMR (400 MHz, MeOD) δ ppm 0.8 (dd, J=29.7, 6.7Hz, 6 H) 1.1 (s, 9 H) 1.9 (m, 1 H) 3.5 (d, J=5.8 Hz, 1 H) 5.0 (s, 2 H) 7.0 (d, J=8.8 Hz, 2 H) 7.2 (t, J=7.3 Hz, 1 H) 7.3 (m, 2 H) 7.4 (d, J=6.8 Hz, 2 H) 7.5 (d, J=9.1 Hz, 2 H) 7.6 (d, J=8.6 Hz, 2 H) 7.8 (d, J=8.8 Hz, 2 H).

Step 5C: D-2-(4'-Benzyloxy-biphenyl-4-sulfonylamino)-3-methyl-butyric acid was prepared according to procedures in Step 5C for example 2A in quantitative yield. 1H NMR (400 MHz, DMSO-D6) δ ppm 0.8 (dd, J=12.3, 6.7 Hz, 6 H) 1.9 (m, 1 H) 3.5 (dd, J=9.3, 6.1 Hz, 1 H) 5.2 (s, 2 H) 7.1 (d, J=9.1 Hz, 2 H) 7.4 (m, 3 H) 7.5 (d, J=8.8 Hz, 2 H) 7.7 (d, J=8.8 Hz, 2 H) 7.8 (s, 4 H) 8.0 (d, J=9.3 Hz, 1 H).

Example 2E

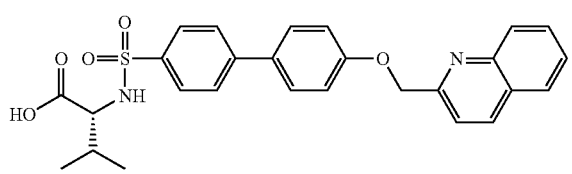

D-3-Methyl-2-[4'-(quinolin-2-ylmethoxy)-biphenyl-4-sulfonylamino]-butyric acid The title compound, D-3-Methyl-2-[4'-(quinolin-2-ylmethoxy)-biphenyl-4-sulfonylamino]-butyric acid, was prepared according to procedures similar to that of Example 2A.

Step 5A: Alkylation of 2-Chloromethyl-quinoline with 4-(4,4,5,5-Tetramethyl-[1,3,2]dioxaborolan-2-yl)-phenol was carried out according to procedures in Step 5A for Example 2A to give 2-[4-(4,4,5,5-Tetramethyl-[1,3,2]dioxaborolan-2-yl)-phenoxymethyl]-quinoline in 90% yield. 1H NMR (400 MHz, MeOD) δ ppm 1.2 (s, 12 H) 5.3 (s, 2 H) 7.0 (d, J=8.6 Hz, 2 H) 7.5 (m, 1 H) 7.6 (dd, J=11.4, 8.6Hz, 3 H) 7.7 (m, 1 H) 7.8 (dd, J=8.1, 1.5 Hz, 1 H) 7.9 (d, J=8.6 Hz, 1 H) 8.3 (d, J=8.6 Hz, 1 H).

Step 5B: Suzuki coupling of 2-[4-(4,4,5,5-Tetramethyl-[1,3,2]dioxaborolan-2-yl)-phenoxymethyl]-quinoline with D-2-(4-Bromo-benzenesulfonylamino)-3-methyl-butyric acid tert-butyl ester was carried out according to procedures in Step 5B for Example 2A to give D-3-Methyl-2-[4'-(quinolin-2-ylmethoxy)-biphenyl-4-sulfonylamino]-butyric acid tert-butyl ester in 70% yield. 1H NMR (400 MHz, MeOD) δ ppm 0.8 (dd, J=29.8, 6.8 Hz, 6 H) 1.1 (s, 9 H) 1.9 (m, 1 H) 3.5 (d, J=5.6 Hz, 1 H) 5.3 (s, 2 H) 7.1 (d, J=8.8 Hz, 2 H) 7.5 (m, 3 H) 7.6 (t, J=8.6 Hz, 3 H) 7.7 (m, 1 H) 7.8 (d, J=8.8 Hz, 2 H) 7.9 (dd, J=8.2, 0.9 Hz, 1 H) 8.0 (m, 1 H) 8.3 (d, J=8.8 Hz, 1 H).

Step 5C: Removal of t-butyl ester was done according to procedures in Step 5C for Example 2A in quantitative yield. 1H NMR (400 MHz, DMSO-D6) δ ppm 0.8 (dd, J=12.5, 6.7 Hz, 6 H) 1.9 (m, 1 H) 3.5 (dd, J=9.3, 6.1 Hz, 1 H) 5.5 (s, 2 H) 7.2 (d, J=8.8 Hz, 2 H) 7.7 (m, 1 H) 7.7 (dd, J=8.7, 1.9 Hz, 3 H) 7.8 (s, 5 H) 8.0 (m, 3 H) 8.5 (d, J=8.6 Hz, 1 H).

Example 2F

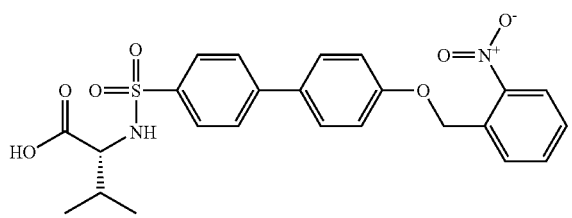

D-3-Methyl-2-[4'-(2-nitro-benzyloxy)-biphenyl-4-sulfonylamino]-butyric acid

The title compound, D-3-Methyl-2-[4'-(2-nitro-benzyloxy)-biphenyl-4-sulfonylamino]-butyric acid, was prepared according to procedures similar to that of Example 2A.

Step 5A: Alkylation of 1-Bromomethyl-2-nitro-benzene with 4-(4,4,5,5-Tetramethyl-[1,3,2]dioxaborolan-2-yl)-phenol was carried out according to procedures in Step 5A for Example 2A to give 4,4,5,5-Tetramethyl-2-[4-(2-nitro-benzyloxy)-phenyl]-[1,3,2]dioxaborolane in 62% yield. 1H NMR (400 MHz, CHLOROFORM-D) δ ppm 1.3 (s, 12 H) 5.5 (s, 2 H) 7.0 (d, J=8.6 Hz, 2 H) 7.5 (m, 1 H) 7.7 (m, 1 H) 7.8 (d, J=8.6 Hz, 2 H) 7.9 (dd, J=7.8, 1.0 Hz, 1 H) 8.2 (dd, J=8.1, 1.3 Hz, 1 H).

Step 5B: Suzuki coupling of 4,4,5,5-Tetramethyl-2-[4-(2-nitro-benzyloxy)-phenyl]-[1,3,2]dioxaborolane with D-2-(4-Bromo-benzenesulfonylamino)-3-methyl-butyric acid tert-butyl ester was carried out according to procedures in Step 5B for 2A to give D-3-Methyl-2-[4'-(2-nitro-benzyloxy)-biphenyl-4-sulfonylamino]-butyric acid tert-butyl ester in 20% yield. 1H NMR (400 MHz, MeOD) δ ppm 0.8 (dd, J=30.1, 6.8 Hz, 6 H) 1.1 (s, 9 H) 1.9 (m, 1 H) 3.5 (d, J=5.6 Hz, 1 H) 5.4 (s, 2 H) 7.0 (d, J=8.8 Hz, 2 H) 7.5 (m, 1 H) 7.5 (d, J=8.8 Hz, 2 H) 7.6 (m, 3 H) 7.8 (d, J=8.6 Hz, 3 H) 8.1 (dd, J=8.1, 1.3 Hz, 1 H).

Step 5C: Removal of t-butyl ester was done according to procedures in Step 5C for Example 2A in quantitative yield. 1H NMR (400 MHz, MeOD) δppm 0.8 (dd, J=24.3, 6.8 Hz, 6 H) 2.0 (m, 1 H) 3.6 (d, J=5.8 Hz, 1 H) 5.4 (s, 2 H) 7.0 (d, J=8.6 Hz, 2 H) 7.5 (t, J=7.7 Hz, 1 H) 7.6 (d, J=8.8 Hz, 2 H) 7.7 (m, 3 H) 7.8 (m, 3 H) 8.1 (d, J=9.6 Hz, 1 H).

Example 2G

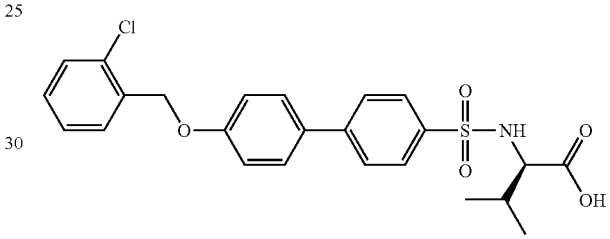

D-2-[4'-(2-Chloro-benzyloxy)-biphenyl-4-sulfonylamino]-3-methyl-butyric acid The title compound, D-2-[4'-(2-Chloro-benzyloxy)-biphenyl-4-sulfonylamino]-3-methyl-butyric acid, was prepared according to procedures similar to that of Example 2A.

Step 5A: Coupling of 2-chlorobenzyl bromide with 4-hydroxyphenyl boronic ester to obtain 2-[4-(2-Chloro-benzyloxy)-phenyl]-4,4,5,5-tetramethyl-[1,3,2]dioxaborolane was done according to procedures in Step 5A for Example 2A. Yield: 85%. 1H NMR (400 MHz, DMSO-D6) δ ppm 1.3 (s, 12 H) 5.2 (s, 2 H) 7.0 (d, J=8.8 Hz, 2 H) 7.4 (m, 2 H) 7.5 (m, 1 H) 7.6 (m, 1 H) 7.6 (d, J=8.8 Hz, 2 H).

Step 5B: Coupling 2-[4-(2-Chloro-benzyloxy)-phenyl]-4,4,5,5-tetramethyl-[1,3,2]dioxaborolane with D-2-(4-Bromo-benzenesulfonylamino)-3-methyl-butyric acid methyl ester to obtain D-2-[4'-(2-Chloro-benzyloxy)-biphenyl-4-sulfonylamino]-3-methyl-butyric acid methyl ester was done according to procedures in Step 5B for Example 2A. Yield: 73%. 1H NMR (400 MHz, DMSO-D6) δ ppm 0.8 (dd, J=15.4, 6.6 Hz, 6 H) 1.9 (m, 1 H) 3.3 (s, 3 H) 3.6 (dd, J=9.3, 7.1 Hz, 1 H) 5.2 (s, 2 H) 7.2 (d, J=8.8 Hz, 2 H) 7.4 (m, 2 H) 7.5 (m, 1 H) 7.6 (m, 1 H) 7.7 (d, J=8.8 Hz, 2 H) 7.8 (d, J=8.6 Hz, 2 H) 7.8 (m, 2 H) 8.3 (d, J=9.3 Hz, 1 H).

Step 5C: Hydrolysis of D-2-[4'-(2-Chloro-benzyloxy)-biphenyl-4-sulfonylamino]-3-methyl-butyric acid methyl ester to D-2-[4'-(2-Chloro-benzyloxy)-biphenyl-4-sulfonylamino]-3-methyl-butyric acid was done according to procedures in Step 5C for Example 2A. Yield: 55%. 1H NMR (400 MHz, DMSO-D6) δ ppm 0.8 (dd, J=12.6, 6.8 Hz, 6 H)

1.9 (m, 1 H) 3.5 (dd, J=9.2, 5.9 Hz, 1 H) 5.2 (s, 2 H) 7.2 (d, J=8.8 Hz, 2 H) 7.4 (m, 2 H) 7.5 (m, 1 H), 7.6 (m, 1 H) 7.7 (d, J=8.8 Hz, 2 H) 7.8 (s, 4 H) 8.0 (d, J=9.3 Hz, 1 H) 12.6 (s, 1 H).

Example 2H

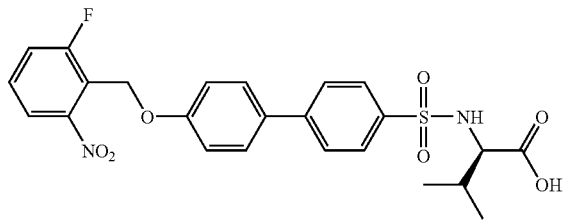

D-2-[4'-(2-Fluoro-6-nitro-benzyloxy)-biphenyl-4-sulfonylamino]-3-methyl-butyric acid The title compound, D-2-[4'-(2-Fluoro-6-nitro-benzyloxy)-biphenyl-4-sulfonylamino]-3-methyl-butyric acid, was prepared according to procedures similar to that of Example 2A.

Step 5A: Coupling of 2-fluoro-6-nitrobenzyl bromide with 4-hydroxyphenyl boronic ester to obtain 2-[4-(2-Fluoro-6-nitro-benzyloxy)-phenyl]-4,4,5,5-tetramethyl-[1,3,2]dioxaborolane was done according procedures in Step 5A for Example 2A. Yield: 95%. 1H NMR (400 MHz, DMSO-D6) δ ppm 1.3 (s, 12 H) 5.3 (d, J=1.3 Hz, 2 H) 7.0 (d, J=8.8 Hz, 2 H) 7.6 (d, J=8.8 Hz, 2 H) 7.7 (m, 2 H) 7.9 (m, 1 H).

Step 5B: Coupling 2-[4-(2-Fluoro-6-nitro-benzyloxy)-phenyl]-4,4,5,5-tetramethyl-[1,3,2]dioxaborolane with D-2-(4-Bromo-benzenesulfonylamino)-3-methyl-butyric acid methyl ester to obtain D-2-[4'-(2-Fluoro-6-nitro-benzyloxy)-biphenyl-4-sulfonylamino]-3-methyl-butyric acid methyl ester was done according to procedures in Step 5B for Example 2A. Yield: 49%. 1H NMR (400 MHz, DMSO-D6) δ ppm 0.8 (dd, J=15.2, 6.8 Hz, 6 H) 1.9 (m, 1 H) 3.3 (s, 3 H) 3.6 (dd, J=9.5, 7.2 Hz, 1 H) 5.4 (d, J=1.3 Hz, 2 H) 7.1 (d, J=8.8 Hz, 2 H) 7.8 (m, 6 H) 7.8 (m, 2 H) 7.9 (m, 1 H) 8.3 (m, J=9.3 Hz, 1 H).

Step 5C: Hydrolysis of D-2-[4'-(2-Fluoro-6-nitro-benzyloxy)-biphenyl-4-sulfonylamino]-3-methyl-butyric acid methyl ester to D-2-[4'-(2-Fluoro-6-nitro-benzyloxy)-biphenyl-4-sulfonylamino]-3-methyl-butyric acid was done according to procedures in Step 5C for Example 2A, except purification through prep-HPLC. Yield: 30%. 1H NMR (400 MHz, DMSO-D6) δ ppm 0.8 (dd, J=12.9, 6.8 Hz, 6 H) 1.9 (m, 1 H) 3.5 (dd, J=9.2, 5.9 Hz, 1 H) 5.4 (d, J=1.3 Hz, 2 H) 7.1 (d, J=8.8 Hz, 2 H) 7.7 (m, 4 H) 7.8 (d, J=0.8 Hz, 4 H) 7.9 (m, 2 H) 8.0 (d, J=9.1 Hz, 1 H).

Example 2I

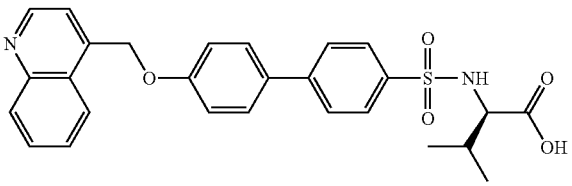

D-3-Methyl-2-[4'-(quinolin-4-ylmethoxy)-biphenyl-4-sulfonylamino]-butyric acid

The title compound, D-3-Methyl-2-[4'-(quinolin-4-ylmethoxy)-biphenyl-4-sulfonylamino]-butyric acid, was prepared according to procedures similar to that of Example 2A.

Step 5A: Coupling of 4-Chloromethyl-quinoline with 4-hydroxyphenyl boronic ester to obtain 4-[4-(4,4,5,5-Tetramethyl-[1,3,2]dioxaborolan-2-yl)-phenoxymethyl]-quinoline was done according to procedures in Step 5A for Example 2A. Yield: 62%. 1H NMR (400 MHz, DMSO-D6) δ ppm 1.3 (s, 12 H) 5.7 (d, J=0.5 Hz, 2 H) 7.1 (d, J=8.8 Hz, 2 H) 7.7 (m, 4 H) 7.8 (m, 1 H) 8.1 (dd, J=8.5, 0.9 Hz, 1 H) 8.2 (d, J=8.3 Hz, 1 H) 8.9 (d, J=4.5 Hz, 1 H).

Step 5B: Coupling of 4-[4-(4,4,5,5-Tetramethyl-[1,3,2]dioxaborolan-2-yl)-phenoxymethyl]-quinoline with D-2-(4-Bromo-benzenesulfonylamino)-3-methyl-butyric acid methyl ester to obtain D-3-Methyl-2-[4'-(quinolin-4-ylmethoxy)-biphenyl-4-sulfonylamino]-butyric acid methyl ester was done according to procedures in Step 5B for example 2A. Yield: 47%. 1H NMR (400 MHz, DMSO-D6) δ ppm 0.8 (dd, J=15.2, 6.8 Hz, 6 H) 1.9 (m, 1 H) 3.3 (s, 3 H) 3.6 (dd, J=9.3, 7.1 Hz, 1 H) 5.8 (s, 2 H) 7.3 (d, J=8.8 Hz, 2 H) 7.8 (m, 9 H) 8.1 (d, J=8.6 Hz, 1 H) 8.2 (d, J=8.6 Hz, 1 H) 8.3 (d, J=9.3 Hz, 1 H) 8.9 (d, J=4.3 Hz, 1 H).

Step 5C: Hydrolysis of D-3-Methyl-2-[4'-(quinolin-4-ylmethoxy)-biphenyl-4-sulfonylamino]-butyric acid methyl ester to D-3-Methyl-2-[4'-(quinolin-4-ylmethoxy)-biphenyl-4-sulfonylamino]-butyric acid was done according to procedures in Step 5C for Example 2A. Yield: 54%. 1H NMR (400 MHz, DMSO-D6) δ ppm 0.8 (dd, J=43.6, 6.9 Hz, 6 H) 2.0 (m, 1 H) 3.0 (d, J=3.0 Hz, 1 H) 5.8 (d, 2 H) 7.3 (d, J=8.8 Hz, 2 H) 7.7 (m, 4 H) 7.8 (m, 5 H) 8.1 (m, 1 H) 8.2 (dd, J=8.3, 0.8 Hz, 1 H) 8.9 (d, J=4.5 Hz, 1 H).

Example 2J

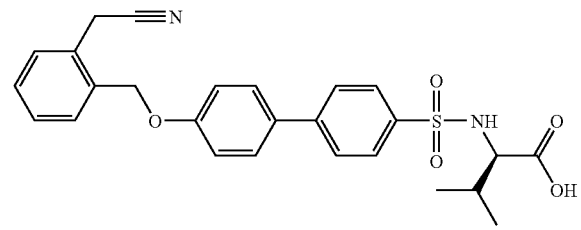

D-2-[4'-(2-Cyanomethyl-benzyloxy)-biphenyl-4-sulfonylamino]-3-methyl-butyric acid The title compound, D-3-Methyl-2-[4'-(quinolin-4-ylmethoxy)-biphenyl-4-sulfonylamino]-butyric acid, was prepared according to procedures similar to that of Example 2A.

Step 5C: Hydrolysis of D-2-[4'-(2-Cyanomethyl-benzyloxy)-biphenyl-4-sulfonylamino]-3-methyl-butyric acid methyl ester (prepared according to step 3) to D-2-[4'-(2-Cyanomethyl-benzyloxy)-biphenyl-4-sulfonylamino]-3-methyl-butyric acid was done according to procedures in Step 5C for Example 2A. Prep-HPLC was used for purification. Yield: 75%. 1H NMR (400 MHz, DMSO-D6) δ ppm 0.8 (dd, J=23.7, 6.8 Hz, 6 H) 2.0 (m, 1 H) 2.8 (d, J=6.6 Hz, 1 H) 4.1 (s, 2 H) 5.2 (s, 2 H) 7.2 (d, J=9.1 Hz, 2 H) 7.4 (m, 2 H) 7.5 (m, 2 H) 7.6 (m, 1 H) 7.7 (d, J=8.8 Hz, 2 H) 7.8 (d, J=2.0 Hz, 4 H).

Examples 2K, 2L, 2M, 2N, 2O, 2P, 2Q, 2R were made based on Scheme 6.

Example 2K

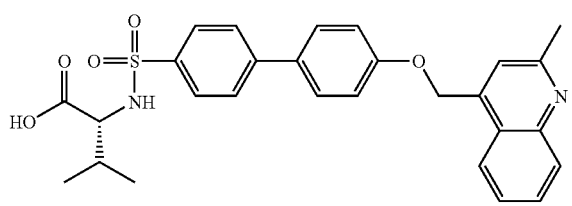

D-3-Methyl-2-[4'-(2-methyl-quinolin-4-ylmethoxy)-biphenyl-4-sulfonylamino]-butyric acid Step: A mixture of 4-Chloromethyl-2-methyl-quinoline (165 mg, 0.86 mmol, 1 eq), D-2-(4'-Hydroxy-biphenyl-4-sulfonylamino)-3-methyl-butyric acid methyl ester (314 mg, 0.86 mmol, 1 eq), and $K_2CO_3$ (270 mg, 1.13 mmol, 1.3 eq) in 8 mL of DMF under nitrogen was heat to 90° C. for 12 hrs. After work up and column chromatography (30–60% EtOAc in hexane), D-3-Methyl-2-[4'-(2-methyl-quinolin-4-ylmethoxy)-biphenyl-4-sulfonylamino]-butyric acid methyl ester was obtained in 34% yield (150 mg). 1H NMR (400 MHz, DMSO-D6) δ ppm 0.8 (dd, J=15.0, 6.7 Hz, 6 H) 1.9 (m, 1 H) 2.7 (s, 3 H) 3.3 (s, 3 H) 3.6 (dd, J=9.2, 7.2 Hz, 1 H) 5.7 (s, 2 H) 7.3 (d, J=8.8 Hz, 2 H) 7.6 (m, 2 H) 7.8 (m, 4 H) 7.8 (m, 2 H) 8.0 (d, J=9.3 Hz, 1 H) 8.1 (d, J=8.3 Hz, 1 H) 8.1 (none, 1 H) 8.3 (d, J=9.6 Hz, 1 H).

Step 6B: D-3-Methyl-2-[4'-(2-methyl-quinolin-4-ylmethoxy)-biphenyl-4-sulfonylamino]-butyric acid methyl ester (150 mg) was dissolved in THF (8 mL) and MeOH (4 mL) and added with 1N LiOH (3 mL,3 mmol). The resulting solution was stirred at room temperature overnight. Reaction was complete as determined by TLC. Solvents removed and regular work-up and column chromatography to afford 148 mg of in quantitative yield. 1H NMR (400 MHz, DMSO-D6) δ ppm 0.8 (dd, J=31.8, 6.8 Hz, 6 H) 2.0 (m, 1 H) 2.7 (s, 3 H) 3.2 (s, 1 H) 5.7 (s, 2 H) 7.3 (d, J=8.8 Hz, 2 H) 7.6 (m, 2 H) 7.8 (m, 7 H) 8.0 (d, J=7.6 Hz, 1 H) 8.1 (d, J=6.8 Hz, 1 H).

Example 2L

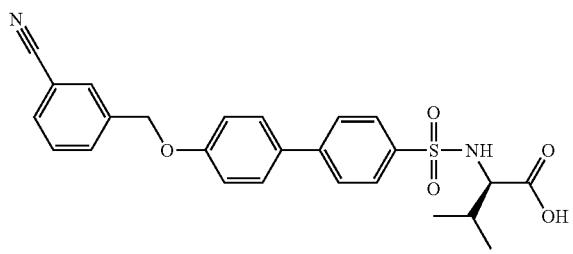

D-2-[4'-(3-Cyano-benzyloxy)-biphenyl-4-sulfonylamino]-3-methyl-butyric acid

The title compound, D-2-[4'-(3-Cyano-benzyloxy)-biphenyl-4-sulfonylamino]-3-methyl-butyric acid, was prepared according to procedures similar to that of Example 2K.

Step 6A: Coupling of α-Bromo-m-tolunitrile with D-2-(4'-Hydroxy-biphenyl-4-sulfonylamino)-3-methyl-butyric acid methyl ester to obtain D-2-[4'-(3-Cyano-benzyloxy)-biphenyl-4-sulfonylamino]-3-methyl-butyric acid methyl ester was done according to procedures in Step 6A for Example 2K. Yield: 25%. 1H NMR (400 MHz, DMSO-D6) δ ppm 0.8 (dd, J=14.9, 6.8 Hz, 6 H) 1.9 (m, 1 H) 3.3 (s, 3 H) 3.6 (dd, J=9.5, 7.2 Hz, 1 H) 5.3 (s, 2 H) 7.2 (d, J=9.1 Hz, 2 H) 7.6 (t, J=8.0 Hz, 1 H) 7.7 (m, 4 H) 7.8 (m, 4 H) 8.0 (s, 1 H) 8.3 (d, J=9.3 Hz, 1 H).

Step 6B: Hydrolysis of D-2-[4'-(3-Cyano-benzyloxy)-biphenyl-4-sulfonylamino]-3-methyl-butyric acid methyl ester to D-2-[4'-(3-Cyano-benzyloxy)-biphenyl-4-sulfonylamino]-3-methyl-butyric acid was done according to procedures in Step 6B for Example 2K. Yield: 24%. 1H NMR (400 MHz, DMSO-D6) δ ppm 0.8 (dd, J=26.0, 6.8 Hz, 6 H) 2.0 (m, 1 H) 2.7 (s, 1 H) 5.2 (s, 2 H) 7.2 (d, J=8.8 Hz, 2 H) 7.6 (d, J=7.6 Hz, 2 H) 7.7 (d, J=8.8 Hz, 2 H) 7.8 (m, 6 H) 8.0 (s, 1 H).

Example 2M

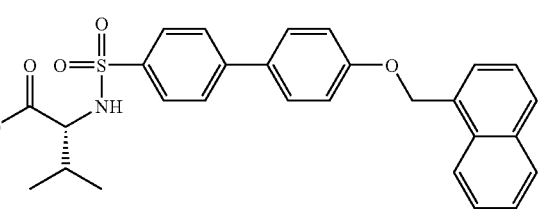

D-3-Methyl-2-[4'-(naphthalen-1-ylmethoxy)-biphenyl-4-sulfonylamino]-butyric acid The title compound, D-3-Methyl-2-[4'-(naphthalen-1-ylmethoxy)-biphenyl-4-sulfonylamino]-butyric acid, was prepared according to procedures similar to that of Example 2K.

Step 6A: Alkylation of 1-Chloromethyl-naphthalene with D-2-(4'-Hydroxy-biphenyl-4-sulfonylamino)-3-methyl-butyric acid methyl ester was carried out according to procedures in Step 6A for Example 2K to give D-3-Methyl-2-[4'-(naphthalen-1-ylmethoxy)-biphenyl-4-sulfonylamino]-butyric acid methyl ester in 34% yield. 1H NMR (400 MHz, CHLOROFORM-D) δ ppm 0.9 (dd, J=32.3, 6.8 Hz, 6 H) 2.0 (m, 1 H) 3.4 (s, 3 H) 3.8 (dd, J=10.1, 5.1 Hz, 1 H) 5.1 (d, J=10.1 Hz, 1 H) 5.6 (s, 2 H) 7.2 (d, J=8.8 Hz, 2 H) 7.5 (dd, J=8.2, 6.9 Hz, 1 H) 7.6 (m, 4 H) 7.6 (d, J=6.6 Hz, 1 H) 7.7 (d, J=8.6 Hz, 2 H) 7.9 (m, 4 H) 8.1 (dd, J=8.5, 1.4 Hz, 1 H).

Step 6B: Hydrolysis of D-3-Methyl-2-[4'-(naphthalen-1-ylmethoxy)-biphenyl-4-sulfonylamino]-butyric acid methyl ester was carried out according to procedures in Step 6B for Example 2K in quantitative yield. 1H NMR (400 MHz, DMSO-D6) δ ppm 0.8 (dd, J=15.4, 6.8 Hz, 6 H) 2.0 (m, 1 H) 3.5 (s, 1 H) 5.6 (s, 2 H) 7.2 (d, J=8.8 Hz, 2 H) 7.6 (m, 3 H) 7.7 (m, 3 H) 7.8 (d, J=2.8 Hz, 4 H) 8.0 (m, 3 H) 8.1 (m, 1 H).

Example 2N

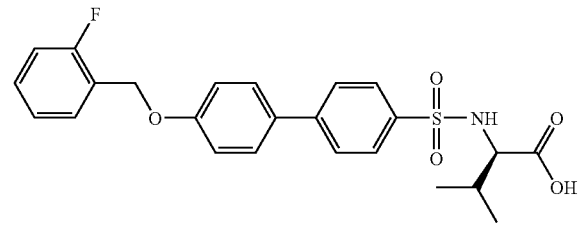

D-2-[4'-(2-Fluoro-benzyloxy)-biphenyl-4-sulfonylamino]-3-methyl-butyric acid

The title compound, D-2-[4'-(2-Fluoro-benzyloxy)-biphenyl-4-sulfonylamino]-3-methyl-butyric acid, was prepared according to procedures similar to that of Example 2K.

Step 6A: Coupling of 2-fluorobenzyl bromide with D-2-(4'-Hydroxy-biphenyl-4-sulfonylamino)-3-methyl-butyric acid methyl ester to obtain D-2-[4'-(2-Fluoro-benzyloxy)-biphenyl-4-sulfonylamino]-3-methyl-butyric acid methyl ester was done according to procedures in Step 6A for Example 2K. Yield: 47%. 1H NMR (400 MHz, DMSO-D6) δ ppm 0.8 (dd, J=15.2, 6.8 Hz, 6 H) 1.9 (dd, 1 H) 3.3 (s, 3 H) 3.6 (dd, J=9.3, 7.1 Hz, 1 H) 5.2 (s, 2 H) 7.2 (d, J=8.8 Hz, 2 H) 7.3 (m, 2 H) 7.4 (m, 1 H) 7.6 (m, 1 H) 7.7 (m, 4 H) 7.8 (m, 2 H) 8.3 (d, J=9.3 Hz, 1 H).

Step 6B: Hydrolysis D-2-[4'-(2-Fluoro-benzyloxy)-biphenyl-4-sulfonylamino]-3-methyl-butyric acid methyl ester to D-2-[4'-(2-Fluoro-benzyloxy)-biphenyl-4-sulfonylamino]-3-methyl-butyric acid was done according to procedures in Step 6B for Example 2K. Yield: 67%. 1H NMR (400 MHz, DMSO-D6) δ ppm 0.8 (dd, J=43.7, 6.8 Hz, 6 H) 2.0 (m, 1 H) 2.9 (d, J=2.8 Hz, 1 H) 5.2 (s, 2 H) 6.8 (s, 1 H) 7.2 (d, J=8.8 Hz, 2 H) 7.3 (m, 2 H) 7.4 (m, 1 H) 7.6 (m, 1 H) 7.7 (d, J=8.8 Hz, 2 H) 7.8 (s, 4 H).

Example 2O

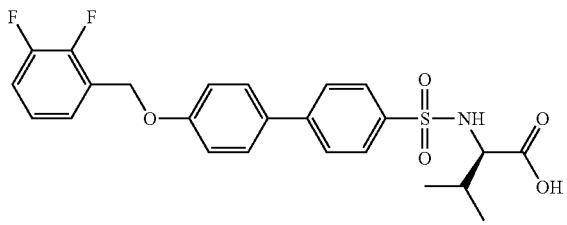

D-2-[4'-(2,3-Difluoro-benzyloxy)-biphenyl-4-sulfonylamino]-3-methyl-butyric acid The title compound, D-2-[4'-(2,3-Difluoro-benzyloxy)-biphenyl-4-sulfonylamino]-3-methyl-butyric acid, was prepared according to procedures similar to that of Example 2K.

Step 6A: Coupling of 2,3-difluorobenzyl bromide with D-2-(4'-Hydroxy-biphenyl-4-sulfonylamino)-3-methyl-butyric acid methyl ester to obtain D-2-[4'-(2,3-Difluoro-benzyloxy)-biphenyl-4-sulfonylamino]-3-methyl-butyric acid methyl ester was done according to procedures in Step 6A for Example 2K but at room temperature for 16 hours. Yield: 42%. 1H NMR (400 MHz, DMSO-D6) δ ppm (s, 2 H) 7.2 (d, J=8.8 Hz, 2 H) 7.3 (m, 1 H) 7.5 (m, 2 H) 7.7 (m, 4 H) 7.8 (m, 2 H) 8.3 (d, J=9.3 Hz, 1 H).

Step 6B: Hydrolysis D-2-[4'-(2,3-Difluoro-benzyloxy)-biphenyl-4-sulfonylamino]-3-methyl-butyric acid methyl ester to D-2-[4'-(2,3-Difluoro-benzyloxy)-biphenyl-4-sulfonylamino]-3-methyl-butyric acid was done according to procedures in Step 6B for example 2K. Yield: 63%. 1H NMR (400 MHz, DMSO-D6) δ ppm 0.8 (dd, J=12.4, 6.8 Hz, 6 H) 1.9 (m, 1 H) 3.5 (dd, J=9.3, 6.1 Hz, 1 H) 5.3 (s, 2 H) 7.2 (d, J=9.1 Hz, 2 H) 7.3 (m, 1 H) 7.5 (m, 2 H) 7.7 (d, J=9.1 Hz, 2 H) 7.8 (d, J=1.8 Hz, 4 H) 8.0 (d, J=9.3 Hz, 1 H) 12.6 (s, 1 H).

Example 2P

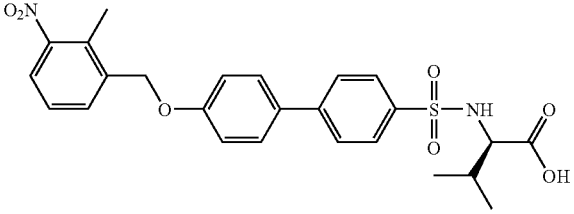

D-3-Methyl-2-[4'-(2-methyl-3-nitro-benzyloxy)-biphenyl-4-sulfonylamino]-butyric acid The title compound, D-3-Methyl-2-[4'-(2-methyl-3-nitro-benzyloxy)-biphenyl-4-sulfonylamino]-butyric acid, was prepared according to procedures similar to that of Example 2K.

Step 6A: Coupling of 2-methyl-3-nitrobenzyl bromide with D-2-(4'-Hydroxy-biphenyl-4-sulfonylamino)-3-methyl-butyric acid methyl ester to obtain D-3-Methyl-2-[4'-(2-methyl-3-nitro-benzyloxy)-biphenyl-4-sulfonylamino]-butyric acid methyl ester was done according to procedures in Step 6A for Example 2K but at room temperature for 16 hours. Product further purified by recrystalization (EtOAc/hexane). Yield: 26%. 1H NMR (400 MHz, DMSO-D6) δ ppm 0.8 (dd, J=15.2, 6.8 Hz, 6 H) 1.9 (m, 1 H) 2.4 (s, 3 H) 3.3 (s, 3 H) 3.6 (m, 1 H) 5.3 (s, 2 H) 7.2 (d, J=8.8 Hz, 2 H) 7.5 (t, J=7.8 Hz, 1 H) 7.8 (m, 8 H) 8.3 (d, J=9.3 Hz, 1 H).

Step 6B: Hydrolysis D-3-Methyl-2-[4'-(2-methyl-3-nitro-benzyloxy)-biphenyl-4-sulfonylamino]-butyric acid methyl ester to D-3-Methyl-2-[4'-(2-methyl-3-nitro-benzyloxy)-biphenyl-4-sulfonylamino]-butyric acid was done according to procedures in Step 6B for Example 2K. Yield: 33%. 1H NMR (400 MHz, DMSO-D6) δ ppm 0.8 (dd, J=12.4, 6.8 Hz, 6 H) 1.9 (dd, 1 H) 3.5 (dd, J=9.3, 6.1 Hz, 1 H) 5.3 (s, 2 H) 7.2 (d, J=9.1 Hz, 2 H) 7.3 (m, 1 H) 7.5 (m, 2 H) 7.7 (d, J=9.1 Hz, 2 H) 7.8 (d, J=1.8 Hz, 4 H) 8.0 (d, J=9.3 Hz, 1 H).

Example 2Q

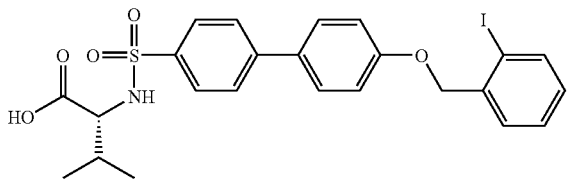

D-2-[4'-(2-Iodo-benzyloxy)-biphenyl-4-sulfonylamino]-3-methyl-butyric acid

The title compound, D-2-[4'-(2-Iodo-benzyloxy)-biphenyl-4-sulfonylamino]-3-methyl-butyric acid, was prepared according to procedures similar to that of Example 2K.

Step 6A: Alkylation of 1-Chloromethyl-2-iodo-benzene with D-2-(4'-Hydroxy-biphenyl-4-sulfonylamino)-3-methyl-butyric acid methyl ester was carried out according to procedures in Step 6A for Example 2K to give D-2-[4'-(2-Iodo-benzyloxy)-biphenyl-4-sulfonylamino]-3-methyl-butyric acid methyl ester in 55% yield. 1H NMR (400 MHz, DMSO-D6) δ ppm 0.8 (dd, J=15.3, 6.7 Hz, 6 H) 1.9 (m, 1 H) 3.3 (s, 3 H) 3.6 (dd, J=9.5, 7.2 Hz, 1 H) 7.1 (m, 3 H) 7.5 (m, 1 H) 7.6 (m, 1 H) 7.7 (m, 4 H) 7.8 (m, 2 H) 7.9 (dd, J=8.0, 1.1 Hz, 1 H) 8.3 (d, J=9.3 Hz, 1 H).

Step 6B: Hydrolysis of D-2-[4'-(2-Iodo-benzyloxy)-biphenyl-4-sulfonylamino]-3-methyl-butyric acid methyl ester was carried out according to procedures in Step 6A for Example 2K in quantitative yield. 1H NMR (400 MHz, DMSO-D6) δ ppm 0.8 (dd, J=12.1, 6.8 Hz, 6 H) 1.9 (m, 1 H) 3.5 (dd, J=9.3, 6.1 Hz, 1 H) 5.1 (s, 2 H) 7.1 (d, J=8.8 Hz, 2 H) 7.5 (m, 1 H) 7.6 (d, J=7.6 Hz, 1 H) 7.7 (d, J=8.8 Hz, 2 H) 7.8 (s, 4 H) 7.9 (dd, J=7.8, 1.3 Hz, 1 H) 8.0 (d, J=9.3 Hz, 1 H).

Example 2R

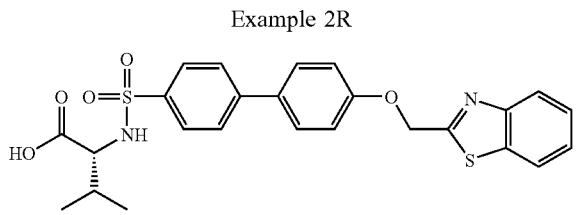

D-2-[4'-(Benzothiazol-2-ylmethoxy)-biphenyl-4-sulfonylamino]-3-methyl-butyric acid The title compound, D-2-[4'-(Benzothiazol-2-yl-methoxy)-biphenyl-4-sulfonylamino]-3-methyl-butyric acid, was prepared according to procedures similar to that of Example 2K.

Step 6A: Alkylation of 2-Bromomethyl-benzothiazole with D-2-(4'-Hydroxy-biphenyl-4-sulfonylamino)-3-methyl-butyric acid methyl ester was carried out according to procedures in Step 6A for Example 2K to give D-2-[4'-(Benzothiazol-2-ylmethoxy)-biphenyl-4-sulfonylamino]-3-methyl-butyric acid methyl ester in 20% yield. 1H NMR (400 MHz, DMSO-D6) δ ppm 0.8 (dd, J=15.0, 6.7 Hz, 6 H) 1.9 (m, 1 H) 3.6 (dd, J=9.5, 7.2 Hz, 1 H) 5.7 (s, 2 H) 7.2 (m, J=8.8 Hz, 2 H) 7.5 (m, 1 H) 7.6 (m, 1 H) 7.7 (m, 4 H) 7.8 (m, 2 H) 8.0 (d, J=7.3 Hz, 1 H) 8.1 (d, J=7.8 Hz, 1 H) 8.3 (d, J=9.6 Hz, 1 H).

Step 6B: Hydrolysis of D-2-[4'-(Benzothiazol-2-yl-methoxy)-biphenyl-4-sulfonylamino]-3-methyl-butyric acid methyl ester was carried out according to procedures in Step 6B for Example 2K in quantitative yield. 1H NMR (400 MHz, DMSO-D6) δ ppm 0.8 (dd, J=12.4, 6.8 Hz, 6 H) 1.9 (m, 1 H) 3.5 (dd, J=9.3, 5.8 Hz, 1 H) 5.7 (s, 2 H) 7.2 (d, J=8.8 Hz, 2 H) 7.5 (m, 1 H) 7.6 (m, 1 H) 7.7 (d, J=8.8 Hz, 2 H) 7.8 (d, J=2.3 Hz, 4 H) 8.0 (dd, J=9.1, 4.5 Hz, 2 H) 8.1 (d, J=8.6 Hz, 1 H). 97%.

Examples 2S, 2T, 2U, 2V, 2W, 2X, 2Y were made based on Scheme 6B.

Example 2S

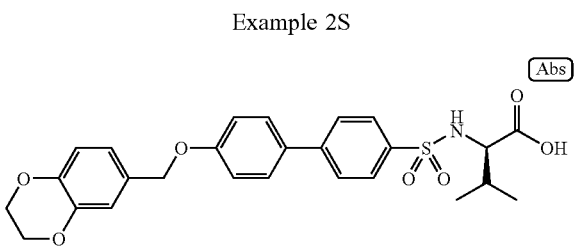

2-[4'-(2,3-Dihydro-benzo[1,4]dioxin-6-ylmemethoxy)-biphenyl-4-sulfonylamino]-3-methyl-butyric acid 1H NMR (400 MHz, DMSO): δ 0.778(d, 3H), 0.845(d, 3H), 1.99(dd, 1H), 3.17(bs, 1H), 4.24(s, 4H), 5.04(s, 2H), 6.91(m, 3H), 7.10(d, 2H), 7.68(d, 2H); ES+ m/z 496.0 (M−H); HRMS (C26H27NO7S): calcd; 520.14004. found; 520.13995 (M+Na).

Example 2T

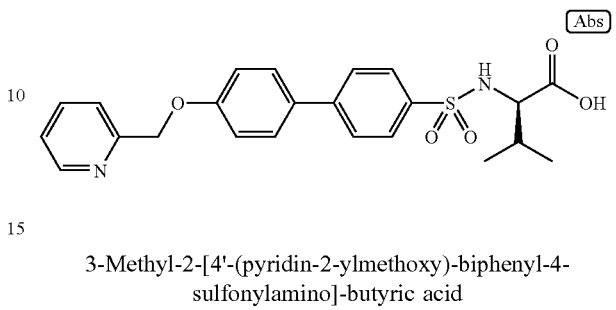

3-Methyl-2-[4'-(pyridin-2-ylmethoxy)-biphenyl-4-sulfonylamino]-butyric acid

1H NMR (400 MHz, DMSO): δ 0.800(d, 3H), 0.803(d, 3H), 1.94(m, 1H), 3.51(bs, 1H), 5.25(s, 2H), 7.15(d, 2H), 7.36(m, 1H), 7.54(d, 2H), 7.71(d, 2H), 7.83(m, 3H), 8.59(d, 2H); ES+ m/z 441.2 (M+H); HRMS (C23H24N2O5S): calcd; 440.14004. found; 440.14037 (M+H).

Example 2U

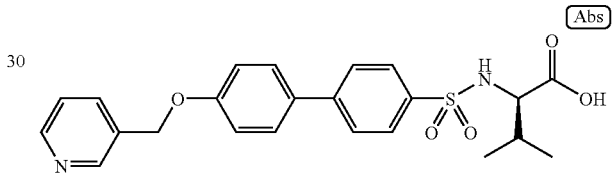

3-Methyl-2-[4'-(pyridin-3-ylmethoxy)-biphenyl-4-sulfonylamino]-butyric acid

1H NMR (400 MHz, DMSO): δ 0.800(d, 3H), 0.803(d, 3H), 1.95(m, 1H), 3.49(bs, 1H), 5.23(s, 2H), 7.16(d, 2H), 7.45(m, 1H), 7.71(d, 2H), 7.80(m, 3H), 7.90(d, 2H), 8.56(d, 1H), 8.70(bs, 1H); ES+ m/z 441.1 (M+H); HRMS (C23H24N2O5S): calcd; 441.14787. found; 441.14617 (M+H).

Example 2V

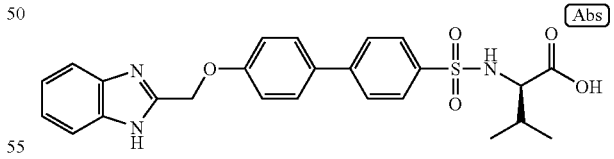

2-[4'-(1H-Benzoimidazol-2-ylmethoxy)-biphenyl-4-sulfonylamino]-3-methyl-butyric acid 1H NMR (400 MHz, DMSO): δ 0.802(d, 3H), 0.833(d, 3H), 1.94(m, 1H), 3.54(m, 1H), 5.51(s, 2H), 6.88(d, 2H), 7.24(d, 1H), 7.34(m, 1H), 7.58(d, 2H), 7.66(m, 1H), 7.78(m, 4H), 8.03(d, 1H); ES+ m/z 480.1 (M+H); HRMS (C25H25N3O5S): calcd; 480.15877. found; 480.15787 (M+H).

Example 2W

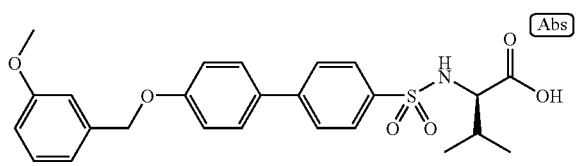

2-[4'-(3-Methoxy-benzyloxy)-biphenyl-4-sulfonylamino]-3-methyl-butyric acid $^1$H NMR (400 MHz, DMSO): δ 0.804(d, 3H), 0.835(d, 3H), 1.95(m, 1H), 3.54(m, 1H), 3.77(s, 3H), 5.15(s, 2H), 6.89(m, 2H), 7.04(m, 2H), 7.13(m, 2H), 7.32(m, 1H), 7.58 (d, 1H), 7.69(d, 2H), 7.80(m, 1H), 8.01(d, 1H); ES$^+$ m/z 470.1 (M+H); HRMS (C25H27NO6S): calcd; 470.16319. found; 470.16183 (M+H).

Example 2X

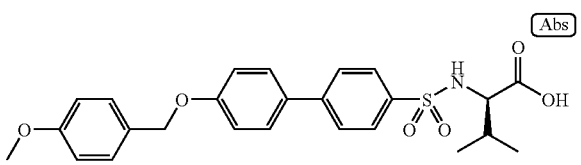

2-[4'-(4-Methoxy-benzyloxy)-biphenyl-4-sulfonylamino]-3-methyl-butyric acid $^1$H NMR (400 MHz, DMSO): δ 0.805(d, 3H), 0.836(d, 3H), 1.94(m, 1H), 3.54(m, 1H), 3.76(s, 3H), 5.09(s, 2H), 6.96(d, 2H), 7.12(d, 2H), 7.40(d, 2H), 7.69(d, 2H), 7.80(s, 3H), 8.01(d, 1H); ES$^+$ m/z 468.2 (M–H); HRMS (C25H27NO6S): calcd; 470.16319. found; 470.16248 (M+H).

Example 2Y

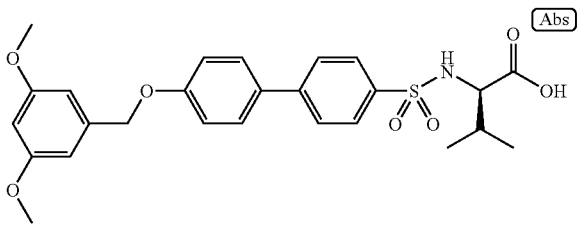

2-[4'-(3,5-Dimethoxy-benzyloxy)-biphenyl-4-sulfonylamino]-3-methyl-butyric acid $^1$H NMR (400 MHz, DMSO): δ 0.804(d, 3H), 0.835(d, 3H), 1.95(m, 1H), 3.55(m, 1H), 3.75(s, 6H), 5.11(s, 2H), 6.45(bs, 1H), 6.62(bs, 2H), 7.12(d, 2H), 7.80(s, 3H), 8.01(d, 1H); ES$^+$ m/z 498.2 (M–H); HRMS (C26H29NO7S): calcd; 500.17375. found; 500.17223 (M+H).

Example 3A was made based on Scheme 7.

Example 3A

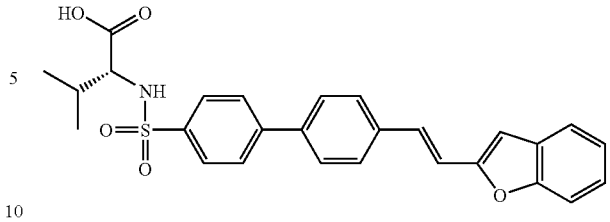

3-Methyl-2-(4'-vinyl-biphenyl-4-sulfonylamino)-butyric acid tert-butyl ester

Step 7A: 4-Vinylphenylboronic acid (1.89 g, 12.7 mmol, 1 equiv.) and 2-(4-Bromo-benzenesulfonylamino)-3-methyl-butyric acid tert-butyl ester (5 g, 12.7 mmol, 1 equiv.) were dissolved in ethylene glycol dimethyl ether (180 mL) and added with Pd(Ph$_3$)$_4$ (736.0 mg, 0.64 mmol) and stirred at room temperature for 20 min. Then to the reaction mixture was introduced an aqueous solution of K$_2$CO$_3$ (3.52 g, 25.5 mmol, 2 equiv.) and heat to reflux overnight. After cool to room temperature, solvent was evaporated and the residue partitioned between EtOAC and H$_2$O. Organic layer washed with brine, dried over MgSO$_4$, and purified by column chromatography (Silica gel, 10% EtOAc/Hexane) to yield 808 mg of G9058-169 in 15.2% yield.

1H NMR (400 MHz, CHLOROFORM-D) δ ppm 0.80 (d, J=6.82 Hz, 3 H) 0.95 (d, J=6.82 Hz, 3 H) 1.12 (s, 9 H) 1.99 (m, 1 H) 3.59 (dd, J=9.85, 4.55 Hz, 1 H) 5.06 (d, J=10.11 Hz, 1 H) 5.25 (d, J=10.86 Hz, 1 H) 5.75 (d, J=16.93 Hz, 1 H) 6.70 (m, 1 H) 7.45 (m, 4 H) 7.61 (d, J=8.84 Hz, 2 H) 7.82 (d, J=8.84 Hz, 2 H)

Step 7B: 3-Methyl-2-(4'-vinyl-biphenyl-4-sulfonylamino)-butyric acid tert-butyl ester (300 mg, 0.72 mmol, 1.2 equiv.), Pd$_2$(dba)$_3$ (11 mg, 0.012 mmol, 0.02 equiv.), Tri-t-butylphosphonium tetrafluoroborate (14 mg, 0.048 mmol, 0.08 equiv.) and dioxane (1.5 mL) were placed in a microwave tube under N$_2$. 2-Bromo-1-Benzofuran (118 mg, 0.6 mmol, 1 equiv) and dicyclohexyl methyl amine (0.15 mL, 0.72 mmol, 1.2 equiv.) were injected. The mixture was then irradiated in microwave reactor at 180° C. for 30 min. The mixture was partitioned between EtOAc and H$_2$O, organic layer dried over MgSO$_4$. Crude residue purified by column chromatography (silica gel, 20% EtOAc/Hexane) to afford 80 mg of 2-[4'-(2-Benzofuran-2-yl-vinyl)-biphenyl-4-sulfonylamino]-3-methyl-butyric acid tert-butyl ester (G9058-171) in 25% yield.

1H NMR (400 MHz, CHLOROFORM-D) δ ppm 0.80 (d, J=6.82 Hz, 3 H) 0.96 (d, J=6.82 Hz, 3 H) 1.14 (s, 9 H) 2.01 (m, 1 H) 3.60 (dd, J=9.98, 4.42 Hz, 1 H) 5.07 (d, J=9.85 Hz, 1 H) 6.66 (s, 1 H) 7.01 (d, J=15.92 Hz, 1 H) 7.14 (m, 1 H) 7.25 (m, 2 H) 7.42 (d, J=8.08 Hz, 1 H) 7.52 (m, 5 H) 7.64 (d, J=8.59 Hz, 2 H) 7.84 (d, J=8.59 Hz, 2 H).

Step 7C: 2-[4'-(2-Benzofuran-2-yl-vinyl)-biphenyl-4-sulfonylamino]-3-methyl-butyric acid tert-butyl ester (80 mg) in dichloroethane (4.5 mL) was added with to TFA (1.5 mL) and stirred at room temperature. The reaction was complete after 3 hrs as determined by TLC. After removing solvent, the crude residue was then purified by column chromatography (5–10% MeOH/CH$_2$Cl$_2$) to give 22 mg of 2-[4'-(2-Benzofuran-2-yl-vinyl)-biphenyl-4-sulfonylamino]-3-methyl-butyric acid G9058-172 in 30.7% yield.

1H NMR (400 MHz, DMSO-D6) δ ppm 0.79 (d, J=6.82 Hz, 3 H) 0.86 (d, J=6.82 Hz, 3 H) 1.23 (s, 2 H) 2.02 (m, 1 H) 3.18 (m, 1 H) 7.01 (s, 1 H) 7.25 (t, J=7.07 Hz, 1 H) 7.33 (m, 1 H) 7.38 (d, J=14.65 Hz, 1 H)7.59 (d, J=8.08 Hz, 1 H) 7.64 (d, J=8.08 Hz, 1 H) 7.79 (d, J=6.57 Hz, 4 H) 7.83 (d, J=8.59 Hz, 2 H) 7.90 (m, 2 H).

Example 4A was made based on Scheme 8.

Example 4A

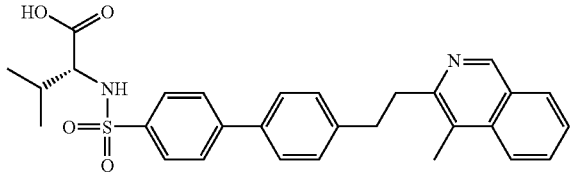

N-({4'-[2-4-methylisoquinolin-3-yl)ethyl]-1,1'-biphenyl-4-yl}sulfonyl)-D-valine

Step 8A2-(4-Bromo-benzenesulfonylamino)-3-methylbutyric acid tert-butyl ester (10.65 g, 27.1 mmol, 1 equiv.), 4-(4,4,5,5-Tetramethyl-1,3,2-dioxaborolan-2-yl)phenol (5.97 g, 27.1 mmol, 1 equiv), Pd(PPh$_3$)$_4$ (1.57 g, 1.4 mmol, 0.05 equiv.) were dissolved in ethylene glycol dimethyl ether (210 mL) under N$_2$ atmosphere and stirred at room temperature for 30 min. Then K$_2$CO$_3$ (7.5 g, 54.3 mmol, 2 equiv.) in H$_2$O (70 mL) was introduced to the reaction mixture and heat to reflux overnight. Reaction was complete as determined by TLC. Solvent was removed by rotovap and the residue partitioned between dichloromethane and brine. Organic layere dried over MgSO$_4$, solvent removed, crude purified by column chromatography (silica gel, 30% EtOAc/n-Hexane) to give 7.1 g of 2-(4'-Hydroxy-biphenyl-4-sulfonylamino)-3-methyl-butyric acid tert-butyl ester in 65% yield.

1H NMR (400 MHz, CHLOROFORM-D) δppm 0.79 (d, J=6.82 Hz, 3 H) 0.95 (d, J=6.57 Hz, 3 H) 1.13 (s, 9 H) 1.51 (s, 1 H) 1.99 (m, 1 H) 3.59 (dd, J=10.11, 4.55 Hz, 1 H) 5.06 (d, J=9.85 Hz, 1 H) 6.86 (d, J=8.84 Hz, 2 H) 7.38 (d, J=8.84 Hz, 2 H) 7.55 (d, J=8.59 Hz, 2 H) 7.79 (d, J=8.59 Hz, 2 H).

Step 8B: 2-(4'-Hydroxy-biphenyl-4-sulfonylamino)-3-methyl-butyric acid tert-butyl ester (330 mg, 0.81 mmol) was dissolved in 20 mL of dry methylene chloride and cool to 0° C. NaH (83 mg, 60% in oil, 2.0 mmol, 2.5 equiv.) was added under N2 and the mixture was stirred for 15 min. Triflic anhydride (251 mg, 0.89 mmol, 1.1 equiv.) was injected and the mixture was warm to room temperature for 1 h. TLC indicated the reaction was complete. The reaction mixture was diluted with methylene chloride and neutralized with 1N HCl. Mixture was washed with water, brine, and dried over MgSO4. Regular column chloromatography (40% EtOAc/hexane) to afford 314 mg of desired product in 72% yield.

1H NMR (400 MHz, CHLOROFORM-D) δ ppm 0.87 (d, J=6.82 Hz, 3 H) 1.03 (d, J=6.82 Hz, 3 H) 1.21 (s, 9 H) 2.01–2.20 (m, 1 H) 3.68 (dd, J=9.85, 4.55 Hz, 1 H) 5.18 (d, J=10.11 Hz, 1 H) 7.39 (d, J=8.84 Hz, 2 H) 7.64 (dd, J=13.52, 8.72 Hz, 4 H) 7.93 (d, J=8.59 Hz, 2 H).

Step: The reaction tube was filled with triflate (300 mg, 0.56 mmol) from Step 8B, lithium chloride (24 mg, 0.56 mmol, 1 eq.), CuI (11 mg, 0.05 mmol, 10%), and PdCl$_2$(PPh$_3$)$_2$ (19.6 mg, 0.028 mmol, 5%) under nitrogen followed by the addition of DMF (5 mL). t-butyldimethylacetylene (235 mg, 1.68 mmol, 3 eq.) and diethylamine (409 mg, 5.6 mmol, 10 eq.) were injected. The tube was irradiated in microwave reactor at 125° C. for 10 min. Starting materials were consumed as determined by TLC. Mixture was partitioned between ethyl acetate and water. Organic phase collected and regular work-up and column chromatography to give 270 mg of desired acetylenic product tert-butyl N-[(4'-{[tert-butyl(dimethyl)silyl]ethynyl}-1,1'-biphenyl-4-yl)sulfonyl]-D-valinate in 92% yield. 1H NMR (400 MHz, CHLOROFORM-D) δ ppm 0.00 (s, 6 H) 0.66 (d, J=6.82 Hz, 3 H) 0.81 (s, 9 H) 0.82 (d, J=6.82 Hz, 3 H) 0.98 (s, 9 H) 1.75–1.98 (m, 1 H) 3.46 (dd, J=9.85, 4.55 Hz, 1 H) 4.93 (d, J=9.85 Hz, 1 H) 7.27–7.32 (m, 2 H) 7.33–7.39 (m, 2 H) 7.47 (d, J=8.84 Hz, 2 H) 7.70 (d, J=8.84 Hz, 2 H).

Step 8D: tert-butyl N-[(4'-{[tert-butyl(dimethyl)silyl]ethynyl}-1,1'-biphenyl-4-yl)sulfonyl]-D-valinate (600 mg, 1.14 mmol) was dissolved in THF (8 mL) and added with TBAF (1.7 mL, 1M, 1.7 mmol, 1.5 eq). The solution was stirred at room temperature for half hour and the reaction was complete. Solvent removed and the residue was purified with column choromatography (silical gel, 20% EtOAc/hexane). 469 mg of product tert-butyl N-[(4'-ethyny-1,1'-biphenyl-4-yl)sulfonyl]-D-valinate was isolated in quantitative yield. 1H NMR (400 MHz, CHLOROFORM-D) δ ppm 0.86 (d, J=6.82 Hz, 2 H) 1.02 (d, J=6.82 Hz, 2 H) 1.20 (s, 9 H) 1.88–2.29 (m, 1 H) 3.17 (s, 1 H) 3.67 (dd, J=9.85, 4.55 Hz, 1 H) 5.14 (d, J=10.11 Hz, 1 H) 7.52 (d, J=8.59 Hz, 2 H) 7.56–7.62 (m, 2 H) 7.67 (d, J=8.84 Hz, 2 H) 7.91 (d, J=8.59 Hz, 2 H).

Step 8E tert-butyl N-[(4'-ethyny-1,1'-biphenyl-4-yl)sulfonyl]-D-valinate (117 mg, 0.28 mmol), 2-chloro-3-methyl-isoquinoline (60 mg, 0.34 mmol, 1.2 eq), CuI (5.3 mg, 0.028 mmol, 10%), and PdCl2(PPh3)2 (9.8 mg, 0.014 mmol, 5%) were placed in a reaction tube under N, and added with DMF (4 mL) and 10 eq. of diethyl amine. The mixture was irradiated at 125° C. for 10 min. Reaction was complete as determined by LCMS. Dilute the mixture with EtOAc and washed with water 3 times, brine once then dried over MgSO4. Column chromatography (silica gel, 30% EtOAc/hexane) to provide 120 mg of desired product tert-butyl N-({4'-[(4-methylisoquinolin-3-yl)ethynyl]-1,1'-biphenyl-4-yl}sulfonyl)-D-valinate in 76% yield. 1H NMR (400 MHz, DMSO-D6) δ ppm 0.86 (dd, J=8.59, 6.82 Hz, 6 H) 1.17 (s, 9 H) 1.94 (m, 1 H) 2.67 (s, 3 H) 3.50 (dd, J=10.61, 7.33 Hz, 1 H) 7.62 (t, J=7.45 Hz, 1 H) 7.69–7.78 (m, 1 H) 7.80–7.85 (m, 4 H) 7.87 (d, J=8.59 Hz, 2 H) 7.90–7.97 (m, 2 H) 8.00 (d, J=8.59 Hz, 1 H) 8.20 (d, J=9.60 Hz, 1 H) 8.30 (s, 1 H).

Step 8F: tert-butyl N-({4'-[(4-methylisoquinolin-3-yl)ethynyl]-1,1'-biphenyl-4-yl}sulfonyl)-D-valinate (46 mg, 0.08 mmol) was dissolved in 25 mL of methanol and added with catalytic amount of Pd/C (8.5 mg, 10% weight on Carbon, 0.008 mmol). The hydrogenation was carried out in a Parr shaker bottle under H$_2$ (50 PSI). Reaction was terminated after 5 hours and LCMS indicated the reaction was complete. The mixture was filtered through Celite and concentrated to the desired product G8594-178 in quantitative yield (46 mg). 1H NMR (400 MHz, DMSO-D6) δ ppm 0.77–0.93 (m, 6 H) 1.15 (s, 9 H) 1.85–2.06 (m, 1 H) 2.51 (s, 3 H) 3.13–3.28 (m, 2 H) 3.25–3.39 (m, 2 H) 3.47 (d, J=8.84 Hz, 1 H) 7.47 (d, J=8.08 Hz, 2 H) 7.52 (t, J=7.45 Hz, 1 H) 7.59–7.71 (m, 3 H) 7.76–7.90 (m, 4 H) 7.97 (d, J=8.34 Hz, 1 H) 8.06 (s, 1 H) 8.15 (s, 1 H).

Step 8G: tert-butyl N-({4'-[2-(4-methylisoquinolin-3-yl)ethyl]-1,1'-biphenyl-4-yl}sulfonyl)-D-valinate (46 mg, 0.08 mmol) was dissolved in 5 mL of dry methylene chloride followed by the addition of 2.5 mL of TFA. The mixture was stirred at room temperature for 3 hrs and TLC indicated the reaction was complete. Solvent was removed by rotavap and the product dried in vacuum oven overnight. 44 mg of product N-({4'-[2-(4-methylisoquinolin-3-yl)ethyl]-1,1'-biphenyl-4-yl}sulfonyl-D-valine was obtained in 95% yield.

1H NMR (400 MHz, MeOD) δ ppm 0.83 (d, J=6.82 Hz, 3 H) 0.88 (d, J=6.82 Hz, 3 H) 1.80–2.13 (m, 1 H) 2.57 (s, 3 H) 3.15 (t, J=7.83 Hz, 2 H) 3.45–3.55 (m, 2 H) 3.60 (d, J=5.56 Hz, 1 H) 7.25 (d, J=8.08 Hz, 2 H) 7.53 (d, J=8.08 Hz, 2 H) 7.65 (d, J=8.34 Hz, 2 H) 7.81 (d, J=8.59 Hz, 3 H) 7.98 (t, J=7.58 Hz, 1 H) 8.02–8.09 (m, 1 H) 8.13 (d, J=8.08 Hz, 1 H) 8.83 (s, 1 H).

Example 5A was made based on Scheme 9.

Example 5A

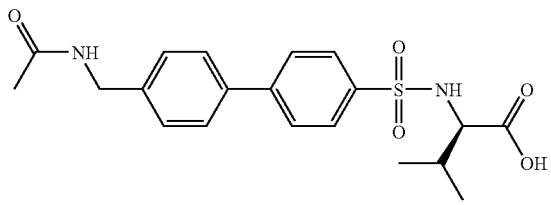

D-2-[4'-(Acetylamino-methyl)-biphenyl-4-sulfonylamino]-3-methyl-butyric acid

Step 9A: Combined 4-aminomethyl phenyl boronic acid (143 mg, 0.77 mmol, 1 eq), D-2-(4-Bromo-benzenesulfonylamino)-3-methyl-butyric acid tert-butyl ester (300 mg, 0.77 mmol, 1 eq), palladium tetrakis (44 mg, 0.038 mmol, 0.05 eq) in dimethoxy ethane (10 mL) and stirred at room temperature for 10 min. Potassium carbonate (212 mg, 1.53 mmol, 2 eq) in 4 mL of water was added to the reaction mixture and heated at 88° C. for 4 hrs. The reaction is then cool to room temperature and diluted with ethyl acetate, washed with brine, dried over magnesium sulfate and stripped to dryness. Residue is purified via flash chromatography on silica gel eluting with 4–10% MeOH in methylene chloride with 2% Et₃N to obtain 200 mg of D-2-(4'-Aminomethyl-biphenyl-4-sulfonylamino)-3-methyl-butyric acid tert-butyl ester. Yield: 63%. 1H NMR (400 MHz, DMSO-D6) δ ppm 0.9 (dd, J=8.1, 7.1 Hz, 6 H) 1.1 (s, 9 H) 1.9 (m, 1 H) 3.5 (d, J=6.3 Hz, 2 H) 3.8 (s, 2 H) 7.5 (d, J=8.3 Hz, 2 H) 7.6 (d, J=8.3 Hz, 2 H) 7.8 (d, J=2.0 Hz, 4 H).

Step 9B: To acetic anhydride (71 uL, 0.75 mmol, 1.05 eq.) in CH₂Cl₂ (5 mL) was added with pyridine (70 uL, 0.86 mmol, 1.2 eq.), under argon and stirred for 5 min, then D-2-(4'-Aminomethyl-biphenyl-4-sulfonylamino)-3-methyl-butyric acid tert-butyl ester (300 mg, 0.72 mmol, 1 eq.) was added and stirred for 16 hours. After work-up and flash column chromatography, D-2-[4'-(Acetylamino-methyl)-biphenyl-4-sulfonylamino]-3-methyl-butyric acid tert-butyl ester was obtained. Yield: 32%. 1H NMR (400 MHz, DMSO-D6) δ ppm 0.8 (dd, J=9.1,6.8Hz, 6 H) 0.9 (t, J=7.3 Hz, 3 H) 1.2 (s, 9 H) 1.3 (m, 2 H) 1.5 (m, 2 H) 1.9 (m, 1 H) 2.5 (m, 2 H) 3.4 (dd, J=9.6, 6.3 Hz, 1 H) 7.0 (dd, 4 H) 7.1 (m, 2 H) 7.5 (d, J=8.8 Hz, 2 H) 7.7 (d, J=9.6 Hz, 1 H) 8.6 (s, 1 H).

Step 9C: To a solution of D-2-[4'-(Acetylamino-methyl)-biphenyl-4-sulfonylamino]-3-methyl-butyric acid tert-butyl ester (300 mg, 0.65 mmol) in 6 mL of dichloroethane was added 3 mL of trifluoroacetic acid. The reaction mixture was stirred at room temperature for 4 hrs and reaction was complete as determined by TLC. Solvent removed and residue dried over vacuum oven to obtain 250 mg of D-2-[4'-(Acetylamino-methyl)-biphenyl-4-sulfonylamino]-3-methyl-butyric acid. Yield: 94%. 1H NMR (400 MHz, DMSO-D6) δ ppm 0.8 (dd, J=12.5, 6.7 Hz, 6 H) 1.9 (s, 3 H) 2.0 (m, 1 H) 3.6 (dd, J=9.3, 5.8 Hz, 1 H) 4.3 (d, J=5.8 Hz, 2 H) 7.4 (d, J=8.1 Hz, 2 H) 7.7 (d, J=8.3 Hz, 2 H) 7.8 (s, 4 H) 8.1 (d, J=9.3 Hz, 1 H) 8.4 (t, J=5.8 Hz, 1 H) 12.6 (s, 1 H).

Examples 5B and 5C were made based on Scheme 10.

Example 5B

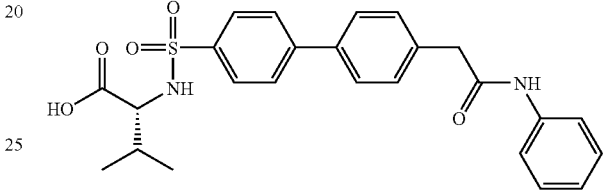

D-3-Methyl-2-(4'-phenylcarbamoylmethyl-biphenyl-4-sulfonylamino)-butyric acid

Step 10A: A mixture of 4-Bromophenylacetic acid (1.5 g, 7.0 mmol, 1 eq.), EDC (2.67 g, 14.0 mmol, 2 eq.), DMAP (846 mg, 7.0 mmol, 1 eq.), and phenylamine (0.765 mL, 8.4 mmol, 1.2 eq.) in 15 mL of DMF was stirred under nitrogen at room temperature for 3.5 hrs. After aqueous workup and recrystallization, 2-(4-Bromophenyl)-N-phenyl-acetamide was obtained in 69% yield (1.4 g). 1H NMR (400 MHz, DMSO-D6) δ ppm 3.6 (s, 2 H) 7.0 (m, 1 H) 7.3 (m, 4 H) 7.5 (m, 2 H) 7.6 (dd, J=8.7, 1.1 Hz, 2 H) 10.2 (s, 1 H).

Step 10B: A mixture of 2-(4-Bromophenyl)-N-phenyl-acetamide (107 mg, 0.37 mmol, 1.1 eq.), D-3-Methyl-2-(4-tributylstannanyl-benzenesulfonylamino)-butyric acid tert-butyl ester (202 mg, 0.34 mmol, 1 eq.), and Pd(PPh₃)₄ (38.5 mg, 0.033 mmol, 0.1 eq.) in 5 mL of toluene was heated to reflux under nitrogen. Reaction was complete after 5 hrs. Regular work-up and column purification, D-3-Methyl-2-(4'-phenylcarbamoylmethyl-biphenyl-4-sulfonylamino)-butyric acid tert-butyl ester was obtained in 34% yield (60 mg). 1H NMR (400 MHz, DMSO-D6) δ ppm 0.9 (dd, J=8.3, 6.8 Hz, 6 H) 1.1 (s, 9 H) 1.9 (m, 1 H) 3.5 (dd, J=9.6, 6.3 Hz, 1 H) 3.7 (s, 2 H) 7.0 (t, J=7.3 Hz, 1 H) 7.3 (m, 2 H) 7.5 (d, J=8.3 Hz, 2 H) 7.6 (dd, J=8.6, 1.0 Hz, 2 H) 7.7 (d, J=8.3 Hz, 2 H) 7.8 (d, J=2.5 Hz, 4 H) 8.1 (d, J=9.6 Hz, 1 H) 10.2 (s, 1 H).

Step 10C: Removal of t-butyl ester of D-3-Methyl-2-(4'-phenylcarbamoylmethyl-biphenyl-4-sulfonylamino)-butyric acid tert-butyl ester was done using TFA in dichloroethane (1:1). After evaporation of solvent, D-3-Methyl-2-(4'-phenylcarbamoylmethyl-biphenyl-4-sulfonylamino)-butyric acid was obtained in quantitative yield. 1H NMR (400 MHz, MeOD) δ ppm 0.8 (dd, J=27.0, 6.8 Hz, 6 H) 2.0 (m, 1 H) 3.6 (d, J=5.6 Hz, 1 H) 3.6 (s, 2 H) 7.0 (m, 1 H) 7.2 (m, 2 H) 7.4 (d, J=8.3 Hz, 2 H) 7.5 (dd, J=8.7, 1.1 Hz, 2 H) 7.6 (d, J=8.3 Hz, 2 H) 7.7 (dd, J=48.0, 8.6 Hz, 4 H).

Example 5C

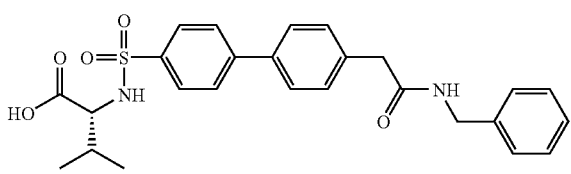

D-2-[4'-(Benzylcarbamoyl-methyl)-biphenyl-4-sulfonylanino]-3-methyl-butyric acid Step 10A: Amide coupling of 4-Bromophenylacetic acid with benzylamine was done according to procedures in Step 10A for Example 5B to give N-Benzyl-2-(4-bromo-phenyl)-acetamide in 82% yield. 1H NMR (400 MHz, DMSO-D6) δ ppm 3.5 (s, 2 H) 4.3 (d, J=5.8 Hz, 2 H) 7.2 (dd, J=7.8, 5.6 Hz, 5 H) 7.3 (m, 2 H) 7.5 (d, J=8.3 Hz, 2 H) 8.6 (t, J=5.9 Hz, 1 H).

Step 10B: Stille coupling of N-Benzyl-2-(4-bromo-phenyl)-acetamide with D-3-Methyl-2-(4-tributylstannanyl-benzenesulfonylamino)-butyric acid tert-butyl ester was carried out according to procedures in Step 10B for Example 5B to give D-2-[4'-(Benzylcarbamoyl-methyl)-biphenyl-4-sulfonylamino]-3-methyl-butyric acid tert-butyl ester in 31% yield. 1H NMR (400 MHz, CHLOROFORM-D) δ ppm 0.9 (d, J=6.8 Hz, 3 H) 1.0 (d, J=6.6 Hz, 3 H) 1.2 (s, 9 H) 2.1 (m, 1 H) 3.7 (m, 3 H) 4.5 (d, J=5.8 Hz, 2 H) 5.1 (d, J=9.9 Hz, 1 H) 5.7 (s, 1 H), 7.3 (m, 5 H) 7.4 (d, J=8.1 Hz, 2 H) 7.5 (d, J=8.3 Hz, 2 H) 7.7 (d, J=8.3 Hz, 2 H) 7.9 (d, J=8.3 Hz, 2 H).

Step 10C: Removal of t-butyl ester was done according to procedures in Step 10C for Example 5B in quantitative yield. 1H NMR (400 MHz, MeOD) δ ppm 0.8 (dd, J=26.3, 6.8 Hz, 6 H) 2.0 (m, 1 H) 3.5 (s, 2 H) 3.6 (d, J=5.6 Hz, 1 H) 4.3 (d, J=5.6 Hz, 2 H) 7.2 (m, 5 ) 7.3 (d, J=8.3 Hz, 2 H) 7.5 (d, J=8.3 Hz, 2 H) 7.7 (d, J=8.8 Hz, 2 H) 7.8 (d, J=8.8 Hz, 2 H) 8.5 (s, 1 H).

Examples 6A, 6B, 6C, 6D, 6E, 6F, 6G, 6H, 6I, 6J, 6K, 6L, 6R, 6S were made based on Scheme 11.

Example 6A

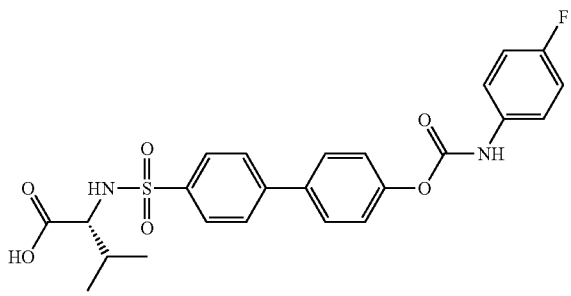

2-[4'-(4-Fluoro-phenylcarbamoyloxy)-biphenyl-4-sulfonylamino]-3-methyl-butyric acid Step 11A: 2-(4'-Hydroxy-biphenyl-4-sulfonylamino)-3-methyl-butyric acid tert-butyl ester (300 mg, 0.74 mmol, 1 eqiv.) was dissolved in diethyl ether (7.5 mL), followed by the addition of 4-fluorophenylisocyanate (101 mg, 0.74 mmol, 1 equiv.) and Et₃N (1 mL). The reaction mixture was stirred at room temperature for 50 min. Solid precipitated from the reaction mixture. Solid was collected by filtration and washed with ether to yield 2-[4'-(4-Fluoro-phenylcarbamoyloxy)-biphenyl-4-sulfonylamino]-3-methyl-butyric acid tert-butyl ester in 57% yield (228 mg).
1H NMR (400 MHz, CHLOROFORM-D) δ ppm 0.87 (d, J=6.82 Hz, 3 H) 1.03 (d, J=6.82 Hz, 3 H) 1.20 (s, 9 H) 2.05 (m, 1 H) 3.67 (dd, J=9.98, 4.42 Hz, 1 H) 5.13 (d, J=9.85 Hz, 1 H) 6.95 (s, 1 H) 7.05 (d, J=9.09 Hz, 2 H) 7.30 (d, J=8.59 Hz, 2 H) 7.43 (m, 2 H) 7.57 (d, J=8.59 Hz, 2 H) 7.67 (s, 2 H) 7.90 (d, J=8.34 Hz, 2 H).

Step 11B: 2-[4'-(4-Fluoro-phenylcarbamoyloxy)-biphenyl-4-sulfonylamino]-3-methyl-butyric acid tert-butyl ester (223 mg) was dissolved in dichloroethane (7.5 mL) and added with TFA (2.5 mL). The mixture was stirred at room temperature for 5 hrs and TLC indicated the reaction was complete. Regular work-up and column chromatography to give 2-[4'-(4-Fluoro-phenylcarbamoyloxy)-biphenyl-4-sulfonylamino]-3-methyl-butyric acid in 89% yield (178 mg).
1H NMR (400 MHz, DMSO-D6) δ ppm 0.81 (d, J=6.57 Hz, 3 H) 0.84 (d, J=6.82 Hz, 3 H) 1.96 (m, 1 H) 3.56 (dd, J=9.35, 6.06 Hz, 1 H) 7.19 (t, J=8.84 Hz, 2 H) 7.37 (d, J=8.59 Hz, 2 H) 7.54 (dd, J=9.09, 4.80 Hz, 2 H) 7.79 (d, J=8.84 Hz, 2 H) 7.86 (d, J=4.29 Hz, 4 H) 8.08 (d, J=9.35 Hz, 1 H) 10.34 (s, 1 H).

Example 6B

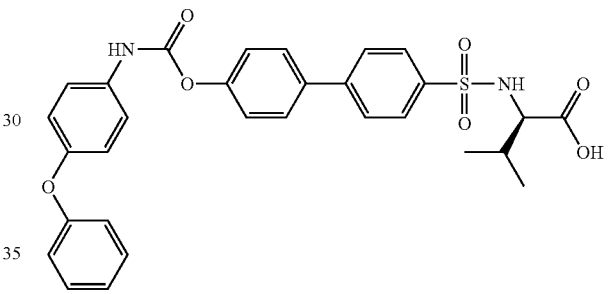

D-3-Methyl-2-[4'-(4-phenoxy-phenylcarbamoyloxy)-biphenyl-4-sulfonylamino]-butyric acid The title compound, D-3-Methyl-2-[4'-(4-phenoxy-phenylcarbamoyloxy)-biphenyl-4-sulfonylamino]-butyric acid, was prepared according to procedures similar to that of Example 6A.

Step 11A: Reaction of 4-phenoxyphenyl isocyanate with D-2-(4'-Hydroxy-biphenyl-4-sulfonylamino)-3-methyl-butyric acid-tert -butyl ester to obtain D-3-Methyl-2-[4'-(4-phenoxy-phenylcarbamoyloxy)-biphenyl-4-sulfonylamino]-butyric acid tert-butyl ester was done according to procedures in Step 11A for Example 6A. Yield: 36%. 1H NMR (400 MHz, DMSO-D6) ☐ ppm 0.9 (dd, J=8.2, 6.9 Hz, 6 H) 1.2 (s, 9 H) 1.9 (m, 1 H) 3.5 (dd, J=9.6, 6.3 Hz, 1 H) 7.0 (dd, J=8.6, 1.0 Hz, 2 H) 7.0 (d, J=9.1 Hz, 2 H) 7.1 (m, 1 H) 7.4 (m, 4 H) 7.5 (d, J=8.8 Hz, 2 H) 7.7 (d, J=8.8 Hz, 2 H) 7.9 (m, 4 H) 8.2 (d, J=9.6 Hz, 1 H) 10.3 (s, 1 H).

Step 11B: Conversion of D-3-Methyl-2-[4'-(4-phenoxy-phenylcarbamoyloxy)-biphenyl-4-sulfonylamino]-butyric acid tert-butyl ester to D-3-Methyl-2-[4'-(4-phenoxy-phenylcarbamoyloxy)-biphenyl-4-sulfonylamino]-butyric acid was done according to procedures in Step 11B for Example 6A. Yield: 87%. 1H NMR (400 MHz, DMSO-D6) δ ppm 0.8 (dd, J=12.1, 6.8 Hz, 6 H) 1.9 (m, 1 H) 3.6 (dd, J=9.3, 6.1 Hz, 1 H) 7.0 (m, 2 H) 7.0 (d, J=9.1 Hz, 2 H) 7.1 (t, J=7.3 Hz, 1 H) 7.4 (m, 4 H) 7.5 (d, J=8.8 Hz, 2 H) 7.8 (d, J=8.8 Hz, 2 H) 7.9 (d, J=4.8 Hz, 4 H) 8.1 (d, J=9.3 Hz, 1 H) 10.3 (s, 1 H).

Example 6C

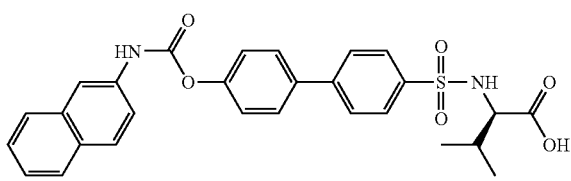

D-3-Methyl-2-[4'-(naphthalen-2-ylcarbamoyloxy)-biphenyl-4-sulfonylamino]-butyric acid The title compound, D-3-Methyl-2-[4'-(naphthalen-2-yl-carbamoyloxy)-biphenyl-4-sulfonylamino]-butyric acid, was prepared according to procedures similar to that of Example 6A.

Step 11A: Reaction of 2-naphthyl isocyanate with D-2-(4'-Hydroxy-biphenyl-4-sulfonylamino)-3-methyl-butyric acid-tert -butyl ester to obtain D-3-Methyl-2-[4'-(naphthalen-2-ylcarbamoyloxy)-biphenyl-4-sulfonylamino]-butyric acid tert-butyl ester was done according to procedures in Step 11A for Example 6A. Yield: 16%. 1H NMR (400 MHz, DMSO-D6) □ ppm 0.9 (dd, J=8.2, 6.9 Hz, 6 H) 1.2 (s, 9 H) 1.9 (m, 1 H) 3.5 (dd, J=9.9, 6.3 Hz, 1 H) 7.4 (m, 3 H) 7.5 (m, 1 H) 7.6 (dd, J=8.8, 2.3 Hz, 1 H) 7.8 (d, J=8.8 Hz, 2 H) 7.9 (m, 7 H) 8.1 (s, 1 H) 8.2 (d, J=9.9 Hz, 1 H) 10.5 (s, 1 H).

Step 11B: Conversion of D-3-Methyl-2-[4'-(naphthalen-2-ylcarbamoyloxy)-biphenyl-4-sulfonylamino]-butyric acid tert-butyl ester to D-3-Methyl-2-[4'-(naphthalen-2-ylcarbamoyloxy)-biphenyl-4-sulfonylamino]-butyric acid was done according to procedures in Step 11B for Example 6A. Yield: 40%. 1H NMR (400 MHz, DMSO-D6) δ ppm 0.8 (dd, J=12.5, 6.7 Hz, 6 H) 2.0 (m, 1 H) 3.6 (dd, J=9.1, 5.8 Hz, 1 H) 7.4 (m, 3 H) 7.5 (m, 1 H) 7.6 (dd, J=8.8, 2.3 Hz, 1 H) 7.9 (m, 9 H) 8.1 (m, 2 H) 10.5 (s, 1 H) 12.6 (s, 1 H).

Example 6D

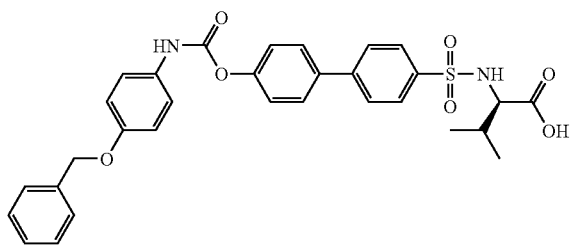

D-2-[41-(4-Benzyloxy-phenylcarbamoyloxy)-biphenyl-4-sulfonylamino]-3-methyl-butyric acid The title compound, D-2-[4'-(4-Benzyloxy-phenylcarbamoyloxy)-biphenyl-4-sulfonylamino]-3-methyl-butyric acid, was prepared according to procedures similar to that of Example 6A.

Step 11A: Reaction of 4-benzyloxyphenyl isocyanate with D-2-(4'-Hydroxy-biphenyl-4-sulfonylamino)-3-methyl-butyric acid-tert -butyl ester to obtain D-2-[4'-(4-Benzyloxy-phenylcarbamoyloxy)-biphenyl-4-sulfonylamino]-3-methyl-butyric acid tert-butyl ester was done according to procedures in Step 11A for Example 6A. Yield: 37%. NMR: G8701-142. 1H NMR (400 MHz, DMSO-D6) δ ppm 0.9 (dd, J=8.1, 6.8 Hz, 6 H) 1.2 (s, 9 H) 1.9 (m, 1 H) 3.5 (dd, J=9.9, 6.3 Hz, 1 H) 5.1 (s, 2 H) 7.0 (d, J=9.1 Hz, 2 H) 7.4 (m, 9 H) 7.7 (d, J=8.8 Hz, 2 H) 7.9 (m, 4 H) 8.2 (d, J=9.6 Hz, 1 H) 10.1 (s, 1 H).

Step 11B: Conversion of D-2-[4'-(4-Benzyloxy-phenylcarbamoyloxy)-biphenyl-4-sulfonylamino]-3-methyl-butyric acid tert-butyl ester to D-2-[4'-(4-Benzyloxy-phenylcarbamoyloxy)-biphenyl-4-sulfonylamino]-3-methyl-butyric acid was done according to procedures in Step 11B for Example 6A. Yield: 60%. NMR: G8701-151. 1H NR (400 MHz, DMSO-D6) δ ppm 0.8 (dd, J=12.1, 6.8 Hz, 6 H) 1.9 (m, 1 H) 3.6 (dd, J=9.3, 6.1 Hz, 1 H) 5.1 (s, 2 H) 7.0 (d, J=9.1 Hz, 2 H) 7.4 (m, 9 H) 7.8 (d, J=8.8 Hz, 2 H) 7.9 (m, 4 H) 8.1 (d, J=9.3 Hz, 1 H) 10.1 (s, 1 H).

Example 6E

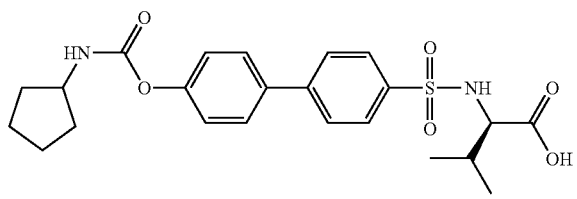

D-2-(4'-Cyclopentylcarbamoyloxy-biphenyl-4-sulfonylamino)-3-methyl-butyric acid

The title compound, D-2-(4'-Cyclopentylcarbamoyloxy-biphenyl-4-sulfonylamino)-3-methyl-butyric acid, was prepared according to procedures similar to that of Example 6A.

Step 11A: Reaction of cyclopentyl isocyanate with D-2-(4'-Hydroxy-biphenyl-4-sulfonylamino)-3-methyl-butyric acid-tert -butyl ester to obtain D-2-(4'-Cyclopentylcarbamoyloxy-biphenyl-4-sulfonylamino)-3-methyl-butyric acid tert-butyl ester was done according to procedures in Step 11A for Example 6A. Yield: 70%. 1H NMR (400 MHz, DMSO-D6) δ ppm 0.9 (dd, J=8.1, 7.1 Hz, 6 H) 1.2 (s, 9 H) 1.5 (m, 4 H) 1.7 (m, 2 H) 1.8 (m, 2 H) 1.9 (m, 1 H) 3.5 (dd, J=9.6, 6.3 Hz, 1 H) 3.9 (m, 1 H) 7.2 (d, J=8.6 Hz, 2 H) 7.7 (d, J=8.6 Hz, 2 H) 7.8 (m, 5 H) 8.2 (d, J=9.6 Hz, 1 H).

Step 11B: Conversion of D-2-(4'-Cyclopentylcarbamoyloxy-biphenyl-4-sulfonylamino)-3-methyl-butyric acid tert-butyl ester to D-2-(4'-Cyclopentylcarbamoyloxy-biphenyl-4-sulfonylamino)-3-methyl-butyric acid was done according to procedures in Step 11B for Example 6A. Yield: 91%. 1H NMR (400 MHz, DMSO-D6) δ ppm 0.8 (m, 6 H) 1.5 (m, 4 H) 1.7 (d, J=4.5 Hz, 2 H) 1.8 (m, 2 H) 1.9 (m, 1 H) 3.6 (dd, J=9.3, 6.1 Hz, 1 H) 3.9 (m, 1 H) 7.2 (d, J=8.6 Hz, 2 H) 7.7 (d, J=8.8 Hz, 2 H) 7.8 (s, 5 H) 8.1 (d, J=9.3 Hz, 1 H) 12.6 (s, 1 H).

Example 6F

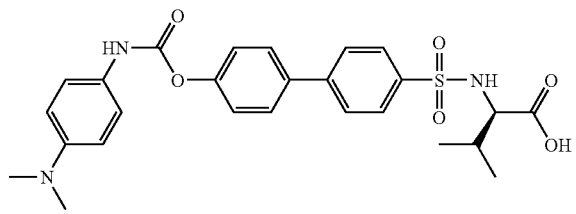

D-2-[4'-(4-Dimethylamino-phenylcarbamoyloxy)-biphenyl-4-sulfonylamino]-3-methyl-butyric acid The title compound, D-2-[4'-(4-Dimethylamino-phenylcarbamoyloxy)-biphenyl-4-sulfonylamino]-3-methyl-butyric acid, was prepared according to procedures similar to that of Example 6A.

Step 11A: Coupling of 4-(dimethylamino)phenyl isocyanate with D-2-(4'-Hydroxy-biphenyl-4-sulfonylamino)-3-methyl-butyric acid-tert -butyl ester to obtain D-2-[4'-(4-Dimethylamino-phenylcarbamoyloxy)-biphenyl-4-sulfonylamino]-3-methyl-butyric acid tert-butyl ester was done according to procedures in Step 11A for Example 6A. Yield: 28%. 1H NMR (400 MHz, DMSO-D6) δ ppm 0.9 (dd, J=8.1, 6.8 Hz, 6 H) 1.2 (s, 9 H) 1.9 (m, 1 H) 2.8 (s, 6 H) 3.5 (dd, J=9.6, 6.3 Hz, 1 H) 6.7 (d, J=9.1 Hz, 2 H) 7.3 (d, J=8.6 Hz, 4 H) 7.7 (d, J=8.6 Hz, 2 H) 7.8 (m, 4 H) 8.2 (d, J=9.9 Hz, 1 H) 9.9 (s, 1 H).

Step 11B: Conversion of D-2-[4'-(4-Dimethylamino-phenylcarbamoyloxy)-biphenyl-4-sulfonylamino]-3-methyl-butyric acid tert-butyl ester to D-2-[4'-(4-Dimethylamino-phenylcarbamoyloxy)-biphenyl-4-sulfonylamino]-3-methyl-butyric acid was done according to procedures in Step 11B for Example 6A. Yield: 99%. NMR: G8701-161. 1H NMR (400 MHz, MeOD) δ ppm 0.8 (dd, J=23.7, 6.8 Hz, 6 H) 2.0 (m, 1 H) 3.1 (s, 6 H) 3.6 (d, J=5.6 Hz, 1 H) 7.2 (d, J=8.8 Hz, 2 H) 7.4 (d, J=9.1 Hz, 3 H) 7.6 (m, 6 H) 7.8 (d, J=8.8 Hz, 2 H).

Example 6G

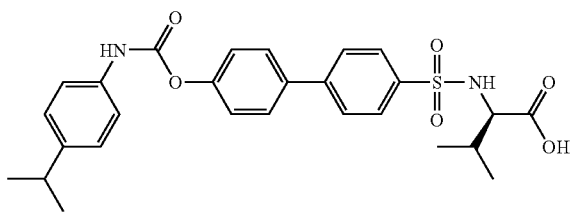

D-2-[4'-(4-Isopropyl-phenylcarbamoyloxy)-biphenyl-4-sulfonylamino]-3-methyl-butyric acid The title compound, D-2-[4'-(4-Isopropyl-phenylcarbamoyloxy)-biphenyl-4-sulfonylamino]-3-methyl-butyric acid, was prepared according to procedures similar to that of Example 6A.

Step 11A: Reaction of 4-isopropylphenyl isocyanate with D-2-(4'-Hydroxy-biphenyl-4-sulfonylamino)-3-methyl-butyric acid-tert -butyl ester to obtain D-2-[4'-(4-Isopropyl-phenylcarbamoyloxy)-biphenyl-4-sulfonylamino]-3-methyl-butyric acid tert-butyl ester was done according to procedures in Step 11A for Example 6A. Yield: 38%. NMR: G8701-158. 1H NMR (400 MHz, DMSO-D6) δ ppm 0.9 (dd, J=8.3, 6.8 Hz, 6 H) 1.2 (m, 15 H) 1.9 (m, 1 H) 2.8 (m, 1 H) 3.5 (dd, J=9.9, 6.3 Hz, 1 H) 7.2 (d, J=8.6 Hz, 2 H) 7.4 (d, J=8.6 Hz, 2 H) 7.4 (d, J=8.6 Hz, 2 H) 7.7 (d, J=8.6 Hz, 2 H) 7.9 (m, 4 H) 8.2 (d, J=9.9 Hz, 1 H) 10.2 (s, 1 H).

Step 11B: Conversion of D-2-[4'-(4-Isopropyl-phenylcarbamoyloxy)-biphenyl-4-sulfonylamino]-3-methyl-butyric acid tert-butyl ester to D-2-[4'-(4-Isopropyl-phenylcarbamoyloxy)-biphenyl-4-sulfonylamino]-3-methyl-butyric acid was done according to procedures in Step 11B for Example 6A. Yield: 34%. NMR: G8701-165. 1H NMR (400 MHz, DMSO-D6) δ ppm 0.8 (dd, J=12.4, 6.8 Hz, 6 H) 1.2 (d, J=6.8 Hz, 6 H) 2.0 (m, 1 H) 2.8 (m, 1 H) 3.6 (dd, J=9.3, 6.1 Hz, 1 H) 7.2 (d, J=8.6 Hz, 2 H) 7.4 (d, J=8.8 Hz, 2 H) 7.4 (d, J=8.6 Hz, 2 H) 7.8 (d, J=8.8 Hz, 2 H) 7.9 (m, 4 H) 8.1 (d, J=9.3 Hz, 1 H) 10.2 (s, 1 H) 12.6 (s, 1 H).

Example 6H

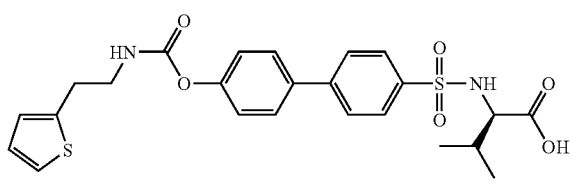

D-3-Methyl-2-[4'-(2-thiophen-2-yl-ethylcarbamoyloxy)-biphenyl-4-sulfonylamino]-butyric acid The title compound, D-3-Methyl-2-[4'-(2-thiophen-2-yl-ethylcarbamoyloxy)-biphenyl-4-sulfonylamino]-butyric acid, was prepared according to procedures similar to that of Example 6A.

Step 11A: Reaction of 2-(2-thienyl)ethyl isocyanate with D-2-(4'-Hydroxy-biphenyl-4-sulfonylamino)-3-methyl-butyric acid-tert -butyl ester to obtain D-3-Methyl-2-[4'-(2-thiophen-2-yl-ethylcarbamoyloxy)-biphenyl-4-sulfonylamino]-butyric acid tert-butyl ester was done according to procedures in Step 11A for Example 6A. Yield: 63%. NMR: G8701-169. 1H NMR (400 MHz, DMSO-D6) δ ppm 0.9 (dd, J=8.3, 7.1 Hz, 6 H) 1.2 (s, 9 H) 1.9 (m, 1 H) 3.0 (t, J=7.1 Hz, 2 H) 3.3 (m, 2 H) 3.5 (dd, J=9.6, 6.3 Hz, 1 H) 7.0 (m, 2 H) 7.2 (d, J=8.8 Hz, 2 H) 7.4 (dd, J=5.1, 1.3 Hz, 1 H) 7.7 (d, J=8.6 Hz, 2 H) 7.8 (d, J=2.3 Hz, 4 H) 8.0 (t, J=5.7 Hz, 1 H) 8.2 (d, J=9.9 Hz, 1 H).

Step 11B: Conversion of D-3-Methyl-2-[4'-(2-thiophen-2-yl-ethylcarbamoyloxy)-biphenyl-4-sulfonylamino]-butyric acid tert-butyl ester to D-3-Methyl-2-[4'-(2-thiophen-2-yl-ethylcarbamoyloxy)-biphenyl-4-sulfonylaamino]-butyric acid was done according to procedures in Step 11B for Example 6A. Yield: 43%. NMR: G8701-175. 1H NMR (400 MHz, DMSO-D6) δ ppm 0.8 (dd, J=12.4, 6.8 Hz, 6 H) 2.0 (m, 1 H) 3.0 (t, J=7.1 Hz, 2 H) 3.3 (m, 2 H) 3.6 (dd, J=9.2, 5.9 Hz, 1 H) 6.9 (dd, J=3.3 Hz, 1 H) 7.0 (dd, J=5.1, 3.3 Hz, 1 H) 7.2 (d, J=8.8 Hz, 2 H) 7.4 (dd, J=5.1, 1.3 Hz, 1 H) 7.7 (d, J=8.6 Hz, 2 H) 7.8 (s, 4 H) 8.0 (t, J=5.8 Hz, 1 H) 8.1 (d, J=9.3 Hz, 1 H).

Example 6I

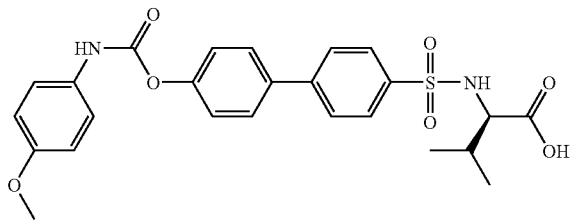

D-3-Methyl-2-[4'-(4-trifluoromethoxy-phenylcarbamoyloxy)-biphenyl-4-sulfonylamino]-butyric acid The title compound, D-3-Methyl-2-[4'-(4-trifluoromethoxy-phenylcarbamoyloxy)-biphenyl-4-sulfonylamino]-butyric acid, was prepared according to procedures similar to that of Example 6A.

Step 11A: Reaction of 4-methoxyphenyl isocyanate with D-2-(4'-Hydroxy-biphenyl-4-sulfonylamino)-3-methyl-butyric acid-tert -butyl ester to obtain D-2-[4'-(4-Methoxy-phenylcarbamoyloxy)-biphenyl-4-sulfonylamino]-3-methyl-butyric acid tert-butyl ester was done according to procedures in Step 11A for Example 6A. Yield: 49%. NMR: G8701-199. 1H NMR (400 MHz, DMSO-D6) δppm 0.9 (dd, J=8.3, 6.8 Hz, 6 H) 1.2 (s, 9 H) 1.9 (m, 1 H) 3.5 (dd, J=9.9, 6.3 Hz, 1 H) 3.7 (s, 3 H) 6.9 (d, J=9.1 Hz, 2 H) 7.4 (d, J=8.8 Hz, 2 H) 7.4 (d, J=8.8 Hz, 2 H) 7.7 (d, J=8.6 Hz, 2 H) 7.9 (m, 4 H) 8.2 (d, J=9.9Hz, 1 H) 10.1 (s, 1 H).

Step 11B: Reaction of D-2-[4'-(4-Methoxy-phenylcarbamoyloxy)-biphenyl-4-sulfonylamino]-3-methyl-butyric acid tert-butyl ester to D-3-Methyl-2-[4'-(4-trifluoromethoxy-phenylcarbamoyloxy)-biphenyl-4-sulfonylamino]-butyric acid was done according to procedures in Step 11B for Example 6A. Yield: 91%. NMR: G9241-4. 1H NMR (400 MHz, DMSO-D6) δ ppm 0.8 (dd, J=12.6, 6.8 Hz, 6 H) 1.9 (m, 1 H) 3.6 (dd, J=9.3, 5.8 Hz, 1 H) 3.7 (s, 3 H) 6.9 (d, J=9.1 Hz, 2 H) 7.4 (d, J=8.8 Hz, 2 H) 7.4 (d, J=8.8 Hz, 2 H) 7.8 (d, J=8.6 Hz, 2 H) 7.9 (m, 4 H) 8.1 (d, J=9.3 Hz, 1 H) 10.1 (s, 1 H) 12.6 (s, 1 H).

Example 6J

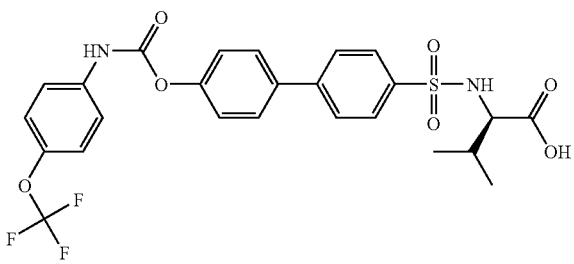

D-3-Methyl-2-[4'-(4-trifluoromethoxy-phenylcarbamoyloxy)-biphenyl-4-sulfonylamino]-butyric acid The title compound, D-3-Methyl-2-[4'-(4-trifluoromethoxy-phenylcarbamoyloxy)-biphenyl-4-sulfonylamino]-butyric acid, was prepared according to procedures similar to that of Example 6A.

Step 11A: To a solution of D-2-(4'-Hydroxy-biphenyl-4-sulfonylamino)-3-methyl-butyric acid-tert-butyl ester (300 mg, 0.74 mmol, 1 eq.) in diethyl ether (10 mL) were added with 4-(trifluoromethoxy)phenyl isocyanate (123 uL, 0.81 mmol, 1.1 eq.) and triethylamine (124 uL, 0.89 mmol, 1.2 eq.) under argon and stirred at room temperature. After reaction complete, regular work-up and flash column chromatography to provide D-3-Methyl-2-[4'-(4-trifluoromethoxy-phenylcarbamoyloxy)-biphenyl-4-sulfonylamino]-butyric acid tert-butyl ester in 37% yield. NMR: G8701-200. 1H NMR (400 MHz, DMSO-D6) □ ppm 0.9 (dd, J=8.1, 6.8 Hz, 6 H) 1.2 (s, 9 H) 1.9 (m, 1 H) 3.5 (dd, J=9.9, 6.3 Hz, 1 NMR: G8701-200. 1H NMR (400 MHz, DMSO-D6) δ ppm 0.9 (dd, J=8.1, 6.8 Hz, 6 H) 1.2 (s, 9 H) 1.9 (m, 1 H) 3.5 (dd, J=9.9, 6.3 Hz, 1 H) 7.4 (m, 4 H) 7.6 (d, J=9.3 Hz, 2 H) 7.8 (d, J=8.8 Hz, 2 H) 7.9 (m, 4 H) 8.2 (d, J=9.6 Hz, 1 H) 10.5 (s, 1 H).

Step 11B: Conversion of D-3-Methyl-2-[4'-(4-trifluoromethoxy-phenylcarbamoyloxy)-biphenyl-4-sulfonylamino]-butyric acid tert-butyl ester to D-3-Methyl-2-[4'-(4-trifluoromethoxy-phenylcarbamoyloxy)-biphenyl-4-sulfonylamino]-butyric acid was done according to procedures in Step 11B for Example 6A. Yield: 76%. NMR: G9241-5. 1H NMR (400 MHz, DMSO-D6) δ ppm 0.8 (dd, J=12.4, 6.8 Hz, 6 H) 2.0 (m, 1 H) 3.6 (dd, J=9.3, 5.8 Hz, 1 H) 7.4 (m, 4 H) 7.6 (d, J=9.1 Hz, 2 H) 7.8 (d, J=8.6 Hz, 2 H) 7.9 (m, 4 H) 8.1 (d, J=9.3 Hz, 1 H) 10.5 (s, 1 H).

Example 6K

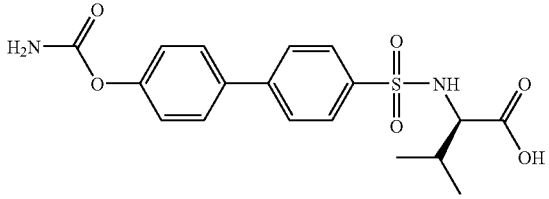

D-2-(4'-Carbamoyloxy-biphenyl-4-sulfonylamino)-3-methyl-butyric acid

The title compound, D-2-(4'-Carbamoyloxy-biphenyl-4-sulfonylamino)-3-methyl-butyric acid, was prepared according to procedures similar to that of Example 6A.

Step 11A: To a solution of D-2-(4'-Hydroxy-biphenyl-4-sulfonylamino)-3-methyl-butyric acid-tert-butyl ester (500 mg, 1.23 mmol, 1 eq.) in CH2Cl2 (2 mL) were added with chlorosulfonyl isocyanate (107 uL, 1.23 mmol, 1 eq.) under argon and stirred at room temperature for 16 hours. Reaction was complete as determined by TLC. After work-up and flash column chromatography, D-2-(4'-Carbamoyloxy-biphenyl-4-sulfonylamino)-3-methyl-butyric acid tert-butyl ester was obtained. Yield: 45%. NMR: G9241-38. 1H NMR (400 MHz, DMSO-D6) δ ppm 0.9 (dd, J=8.3, 6.8 Hz, 6 H) 1.1 (s, 9 H) 1.9 (m, 1 H) 3.5 (dd, J=9.9, 6.3 Hz, 1 H) 7.2 (d, J=8.8 Hz, 2 H) 7.7 (d, J=8.8 Hz, 2 H) 7.8 (d, J=1.0 Hz, 4 H) 8.2 (d, J=9.6 Hz, 1 H).

Step 11B: Conversion of D-2-(4'-Carbamoyloxy-biphenyl-4-sulfonylamino)-3-methyl-butyric acid tert-butyl ester to D-2-(4'-Carbamoyloxy-biphenyl-4-sulfonylamino)-3-methyl-butyric acid was done according to procedures in Step 11B for Example 6A. Yield: 85%. NMR: G9241-46. 1H NMR (400 MHz, DMSO-D6) δ ppm 0.8 (dd, J=12.4, 6.8 Hz, 6 H) 2.0 (m, 1 H) 3.6 (dd, J=9.3, 5.8 Hz, 1 H) 7.0 (s, 1 H) 7.2 (m, 3 H) 7.7 (d, J=8.8 Hz, 2 H) 7.8 (s, 4 H), 8.1 (d, J=9.3 Hz, 1 H).

Example 6L

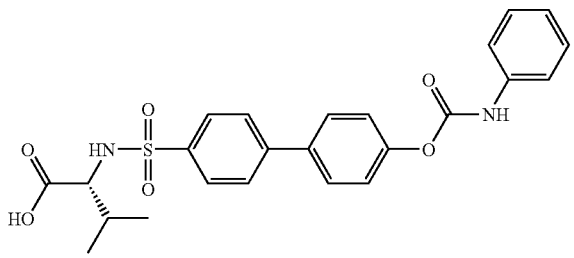

3-Methyl-2-(4'-phenylcarbamoyloxy-biphenyl-4-sulfonylamino)-butyric acid tert-butyl ester The title compound, 3-Methyl-2-(4'-phenylcarbamoyloxy-biphenyl-4-sulfonylamino)-butyric acid tert-butyl ester, was prepared according to procedures similar to that of Example 6A.

Step 11A: 2-(4'-Hydroxy-biphenyl-4-sulfonylamino)-3-methyl-butyric acid tert-butyl ester (300 mg, 0.74 mmol, 1 equiv) was dissolved in diethyl ether (7.5 mL), added with phenylisocyanate (0.08 mL, 0.74 mmol, 1 equiv) followed by Et3N (1 mL). The reaction mixture was stirred for 4 hours. Solid precipitated from the reaction mixture was collected by filtration, washed with ether to afford with 76% yield (295 mg).

1H NMR (400 MHz, CHLOROFORM-D) δ ppm 0.87 (d, J=7.07 Hz, 3 H) 1.03 (d, J=6.82 Hz, 3 H) 1.20 (s, 9 H) 2.07 (m, 1 H) 3.67 (dd, J=9.98, 4.42 Hz, 1 H) 5.13 (d, J=9.85 Hz, 1 H) 6.96 (s, 1 H) 7.14 (m, 1 H) 7.31 (d, J=8.59 Hz, 2 H) 7.36 (m, 2 H) 7.47 (d, J=8.34 Hz, 2 H) 7.58 (d, J=8.59 Hz, 2 H) 7.66 (d, J=8.34 Hz, 2 H) 7.91 (m, 2 H).

Step 11B: 3-Methyl-2-(4'-phenylcarbamoyloxy-biphenyl-4-sulfonylamino)-butyric acid tert-butyl ester (200 mg) was hydrolized according procedures in Step 11B for Example 6A to afford 3-Methyl-2-(4'-phenylcarbamoyloxy-biphenyl-4-sulfonylamino)-butyric acid in 88% yield (158 mg).

1H NMR (400 MHz, DMSO-D6) δ ppm 0.82 (d, J=6.82 Hz, 3 H) 0.85 (d, J=6.57 Hz, 3 H) 1.95 (m, 1 H) 3.56 (dd, J=9.22, 5.94 Hz, 1 H) 3.90 (s, 1 H) 7.07 (m, 1 H) 7.35 (m, 4 H) 7.53 (d, J=7.83 Hz, 2 H) 7.80 (d, J=8.59 Hz, 2 H) 7.86 (d, J=22.23 Hz, 4 H) 8.08 (d, J=9.35 Hz, 1 H) 10.29 (s, 1 H).

Example 6M

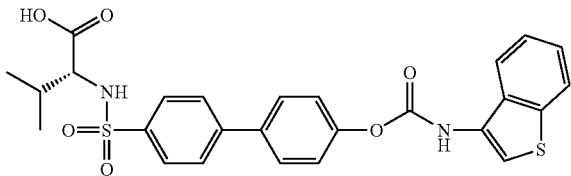

2-[4'-(Benzo[b]thiophen-3-ylcarbamoyloxy)-biphenyl-4-sulfonylamino]-3-methyl-butyric acid tert-butyl ester The title compound, 2-[4'-(Benzo[b]thiophen-3-ylcarbamoyloxy)-biphenyl-4-sulfonylamino]-3-methyl-butyric acid tert-butyl ester, was prepared according to procedures similar to that of Example 6A.

Step 11A: 2-(4'-Hydroxy-biphenyl-4-sulfonylamino)-3-methyl-butyric acid tert-butyl ester (300 mg, 0.74 mmol, 1.0 equiv.) was dissolved in diethyl ether (7.5 mL), added with 1-Benzothiophene-3-yl isocyanate (129.6 mg, 0.74 mmol, 1.0 equiv.) and 0.5 mL of Et₃N. Solid precipitated from the reaction mixture in 5 min. The mixture was continued to stir at room temperature for 2 hrs and the precipitate was collected by filtration, washed with ether to give in 43% yield (187 mg).

1H NMR (400 MHz, CHLOROFORM-D) δ ppm 0.87 (d, J=6.82 Hz, 3 H) 1.03 (d, J=6.82 Hz, 3 H) 1.20 (s, 9 H) 2.08 (m, 1 H) 3.68 (m, 1 H) 5.15 (d, J=10.11 Hz, 1 H) 7.35 (d, J=8.34 Hz, 2 H) 7.43 (m, 2 H) 7.60 (d, J=8.59 Hz, 2 H) 7.67 (d, J=8.34 Hz, 3 H) 7.74 (s, 1 H) 7.90 (t, J=9.09 Hz, 3 H).

Step 11B: 2-[4'-(Benzo[b]thiophen-3-ylcarbamoyloxy)-biphenyl-4-sulfonylamino]-3-methyl-butyric acid tert-butyl ester (180 mg, 0.31 mmol) was dissolved in methylene chloride under N₂ atmosphere, added with TFA (2 mL) at 0° C. and stirred for 4 hrs. Solvent was evaporated and the product dried under high vacuum to give 2-[4'-(Benzo[b]thiophen-3-ylcarbamoyloxy)-biphenyl-4-sulfonylamino]-3-methyl-butyric acid in 66% yield (108 mg).

1H NMR (400 MHz, MeOD) δppm 0.82 (d, J=6.82 Hz, 3 H) 0.89 (d, J=6.82 Hz, 3 H) 1.20 (s, 1 H) 3.54 (d, J=5.05 Hz, 1 H) 7.30 (m, 2 H) 7.35 (m, 2 H) 7.58 (s, 1 H) 7.66 (d, J=8.59 Hz, 2 H) 7.71 (d, J=8.59 Hz, 2 H) 7.78 (d, J=7.83 Hz, 1 H) 7.84 (d, J=8.59 Hz, 2 H) 7.92 (d, J=8.08 Hz, 1 H).

Example 6N

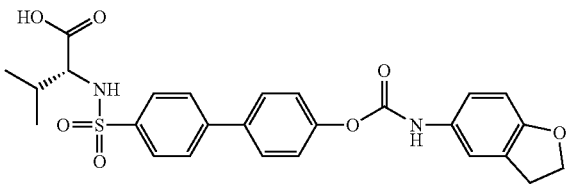

N-[(4'-{[2,3-dihydro-1-benzofuran-5-ylamino)carbonyl]oxy}-1,1'-biphenyl-4yl)sulfonyl]-D-valine The title compound, N-[(4'-{[2,3-dihydro-1-benzofuran-5-ylamino)carbonyl]oxy}-1,1'-biphenyl-4-yl)sulfonyl]-D-valine, was prepared according to procedures similar to that of Example 6A.

Step 11A and 11B: Yield 40%. 1H NMR (400 MHz, DMSO-D6) δ ppm 0.80 (d, J=6.82 Hz, 3 H) 0.85 (d, J=6.82 Hz, 3 H) 1.98 (m, 1 H) 3.17 (t, J=8.97 Hz, 2 H) 3.39 (s, 1 H) 4.50 (t, J=8.59 Hz, 2 H) 6.72 (d, J=8.34 Hz, 1 H) 7.19 (d, J=8.84 Hz, 1 H) 7.34 (d, J=8.59 Hz, 2 H) 7.40 (s, 1 H) 7.78 (d, J=8.59 Hz, 2 H) 7.85 (d, J=1.77 Hz, 4 H) 10.05 (s, 1 H).

Example 6O

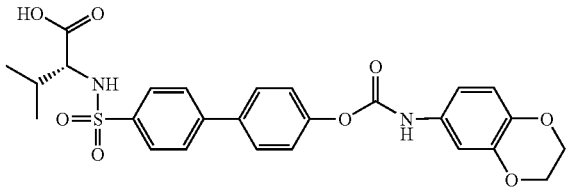

N-[(4'-{[(2,3-dihydro-1,4-benzodioxin-6-ylamino)carbonyl]oxy}-1,1'-biphenyl-4-yl)sulfonyl]-D-valine The title compound, N-[(4'-{[(2,3-dihydro-1,4-benzodioxin-6-ylamino)carbonyl]oxy}-1,1'-biphenyl-4-yl)sulfonyl]-D-valine, was prepared according to procedures similar to that of Example 6A.

Step 11A and: Yield 62%. 1H NMR (400 MHz, DMSO-D6) δ ppm 0.80 (d, J=6.82 Hz, 3 H) 0.85 (d, J=6.82 Hz, 3 H) 1.98 (m, 1 H) 3.42 (s, 1 H) 4.21 (m, 4 H) 6.81 (d, J=8.84 Hz, 1 H) 6.94 (d, J=10.86 Hz, 1 H) 7.09 (s, 1 H) 7.34 (d, J=8.84 Hz, 2 H) 7.78 (d, J=8.84 Hz, 3 H) 7.85 (d, J=1.77 Hz, 4 H) 10.11 (s, 1H).

Example 6P

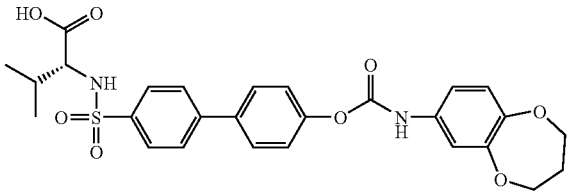

N-[(4'-{[(3,4-dihydro-2H-1,5-benzodioxepin-7-ylamino)carbonyl]oxy}-1,1'-biphenyl-4-yl)sulfonyl]-D-valine The title compound, N-[(4'-{[(3,4-dihydro-2H-1,5-benzodioxepin-7-ylamino)carbonyl]oxy}-1,1'-biphenyl-4-yl)sulfonyl]-D-valine, was prepared according to procedures similar to that of Example 6A.

Step 11A and 11B: Yield 55%. 1H NMR (400 MHz, DMSO-D6) δ ppm 0.80 (d, J=6.82 Hz, 3 H) 0.85 (d, J=6.82 Hz, 3 H) 1.97 (m, 1 H) 2.08 (m, 2 H) 3.45 (s, 1 H) 4.08 (m, 4 H) 6.94 (d, J=8.59 Hz, 1 H) 7.06 (d, J=2.53 Hz, 1 H) 7.18 (d, J=2.27 Hz, 1 H) 7.35 (d, J=8.59 Hz, 2 H) 7.79 (d, J=8.59 Hz, 2 H) 7.85 (d, J=3.79 Hz, 4 H) 7.88 (s, 1 H) 10.21 (s, 1 H).

Example 6Q

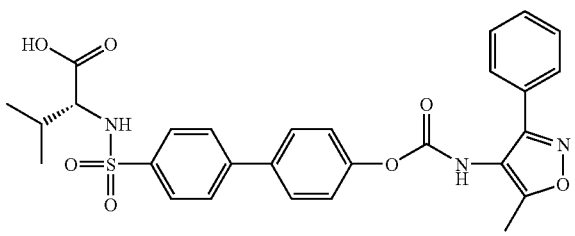

N-[(4'-{[(5-methyl-3-phenylisoxazol-4-yl)amino) carbonyl]oxy}-1,1'-biphenyl-4-yl)sulfonyl]-D-valine The title compound, N-[(4'-{[(5-methyl-3-phenylisoxazol-4-yl)amino)carbonyl]oxy}-1,1'-biphenyl-4-yl)sulfonyl]-D-valine, was prepared according to procedures similar to that of Example 6A.

Step 11B: Yield 75%.1H NMR (400 MHz, ACETONITRILE-D3) δ ppm 0.63 (d, J=6.82 Hz, 3 H) 0.74 (d, J=6.57 Hz, 3 H) 1.83–1.88 (m, 1 H) 2.20 (s, 1 H) 2.34 (m, 3 H) 3.81 (s, 1 H) 6.56 (s, 1 H) 6.66 (s, 1 H) 7.12 (d, J=7.83 Hz, 1 H) 7.45 (d, J=4.80 Hz, 4 H) 7.59 (m, 4 H) 7.68 (d, J=3.54 Hz, 2 H) 7.80 (d, J=8.08 Hz, 2 H).

Example 6R

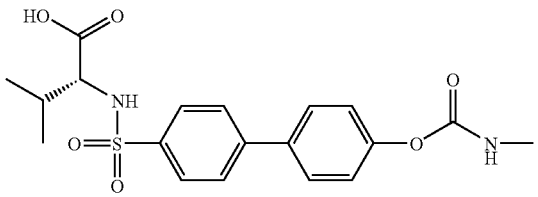

N-[(4'-{[(methylamino)carbonyl]oxy}-1,1'-biphenyl-4-yl)sulfonyl]-D-valine

The title compound, N-[(4'-{[(methylamino)carbonyl] oxy}-1,1'-biphenyl-4-yl)sulfonyl]-D-valine, was prepared according to procedures similar to that of Example 6A.

Step 11B: Yield 90%. 1H NMR (400 MHz, MeOD) δ ppm 0.80 (d, J=8.34 Hz, 3 H) 0.87 (d, J=6.82 Hz, 3 H) 1.91–2.02 (m, 1 H) 2.71 (s, 3 H) 3.52 (d, J=5.05 Hz, 1 H) 7.11 (d, J=8.84 Hz, 2 H) 7.58 (d, J=8.84 Hz, 2 H) 7.66 (d, J=8.59 Hz, 2 H) 7.81 (d, J=8.59 Hz, 2 H).

Example 6S

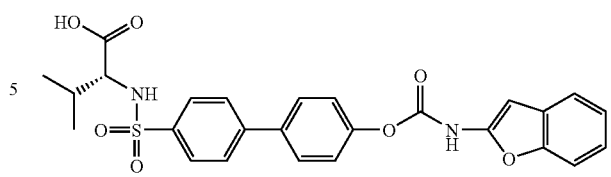

N-[(4'-{[(1-benzofuran-2-ylamino)carbonyl]oxy}-1,1'-biphenyl-4-yl)sulfonyl]-D-valine Step 12A: 2-(4'-Hydroxy-biphenyl-4-sulfonylamino)-3-methyl-butyric acid (314 mg, 0.9 mmol) dissolved in methylene chloride (10 mL) and diethyl ether (20 mL) was added with benzofuran isocyanate (143 mg, 0.9 mmol, 1 equiv) and triethyl amine (363 mg, 3.6 mmol, 4 equiv). The mixture was stirred at room temperature overnight. Solid precipitated from reaction mixture was collected by filtration followed by column chromatography (silica gel, 5% MeOH/CH2Cl2). 76 mg of white solid was obtained in 16% yield.

1H NMR (400 MHz, DMSO-D6) δ ppm 0.74–1.00 (m, 6 H) 1.90–2.07 (m, 1 H) 3.22–3.48 (m, 1 H) 6.86 (d, J=8.59 Hz, 2 H) 7.10–7.28 (m, 2 H) 7.33–7.62 (m, 4 H) 7.69–7.83 (m, 4 H) 7.86 (s, 1 H).

Examples 7A and 7B were made based on Scheme 13.

Example 7A

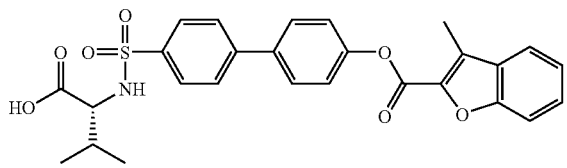

D-3-Methyl-benzofuran-2-carboxylic acid 4'-(1-carboxy-2-methyl-propylsulfamoyl)-biphenyl-4-yl ester Step 13A: A mixture of D-2-(4'-Hydroxy-biphenyl-4-sulfonylamino)-3-methyl-butyric acid tert-butyl ester (305 mg, 0.75 mmol, 1 eq), 3-Methyl-benzofuran-2-carboxylic acid (131 mg, 0.74 mmol, 1 eq), 4-dimethylaminopyridine (DMAP, 95 mg, 0.77 mol, 1 eq), and 1,3-Dicyclohexylcarbodiimide (DCC, 240 mg, 1.17 mmol, 1.6 eq) dissolved in 5 mL of dichloromethane under nitrogen atmosphere was allowed to react at room temperature for 3.5 hrs. Regular work-up and column chromatography (10% EtOAc in hexane) to give D-3-Methyl-benzofuran-2-carboxylic acid 4'-(1-tert-butoxycarbonyl-2-methyl-propylsulfamoyl)-biphenyl-4-yl ester (300 mg) in 71% yield. NMR: G8475-101. 1H NMR (400 MHz, CHLOROFORM-D) δ ppm 0.9 (d, J=7.1 Hz, 3 H) 1.0 (d, J=6.8 Hz, 3 H) 1.2 (s, 9 H) 2.1 (m, 1 H) 2.7 (s, 3 H) 3.7 (dd, J=10.0, 4.4 Hz, 1 H) 5.1 (d, J=9.9 Hz, 1 H) 7.4 (m, 3 H) 7.5 (m, 1 H) 7.6 (t, J=8.0 Hz, 3 H) 7.7 (m, 3 H) 7.9 (d, J=8.3 Hz, 2 H).

Step 13B: Removal of t-butyl ester was done according to procedures in Step 11B for Example 6A in quantitative yield. 1H NMR (400 MHz, DMSO-D6) δ ppm 0.8 (dd, J=12.1, 6.8 Hz, 6 H) 2.0 (m, 1 H) 2.7 (s, 3 H) 3.6 (dd, J=9.2, 5.9 Hz, 1 H) 7.4 (t, J=7.6 Hz, 1 H) 7.5 (d, J=8.8 Hz, 2 H) 7.6 (t, J=8.2 Hz, 1 H) 7.8 (d, J=8.3 Hz, 1 H) 7.9 (m, 7 H) 8.1 (d, J=9.3 Hz, 1 H).

Example 7B

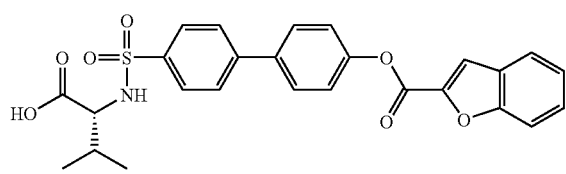

Benzofuran-2-carboxylic acid 4'-(1-tert-butoxycarbonyl-2-methyl-propylsulfamoyl)-biphenyl-4-yl ester The title compound, Benzofuran-2-carboxylic acid 4'-(1-tert-butoxycarbonyl-2-methyl-propylsulfamoyl)-biphenyl-4-yl ester, was prepared according to procedures similar to that of Example 7A.

Step 13A: 2-Benzofuran carbocarboxylic acid (400.5 mg, 2.47 mmol, 1 equiv.) dissolved in dry $CH_2Cl_2$ (50 mL) was added with DCC (1.019 g, 4.94 mmol, 2 equiv) and stirred under $N_2$ for 15 min. Then 2-(4'-Hydroxy-biphenyl-4-sulfonylamino)-3-methyl-butyric acid tert-butyl ester (1.0 g, 2.47 mmol, 1 equiv.) was introduced to the reaction mixture, followed by the addition of DMAP (50 mg, 0.41 mmol,). The mixture was allowed to stir at room temperature overnight. The reaction mixture was then diluted with $CH_2Cl_2$, washed with $H_2O$ and brine. Organic layer dried over $MgSO_4$ and solvent removed to yield crude product. Residue was dissolved in EtOAc and purified by column chromatograph (silica gel, 20% EtOAc/n-Hexane) to afford G9058-53-1 in 30.5% yield (325 mg).

1H NMR (400 MHz, CHLOROFORM-D) δ ppm 0.87 (d, J=6.82 Hz, 3 H) 1.03 (d, J=6.82 Hz, 3 H) 1.21 (s, 9 H) 2.07 (m, 1 H) 3.68 (dd, J=9.85, 4.55 Hz, 1 H) 5.15 (d, J=9.85 Hz, 1 H) 7.37 (m, 3 H) 7.53 (t, J=7.83 Hz, 1 H) 7.66 (m, 5 H) 7.77 (m, 2 H) 7.92 (d, J=8.34 Hz, 2 H).

Step 13B: Benzofuran-2-carboxylic acid 4'-(1-tert-butoxycarbonyl-2-methyl-propylsulfamoyl)-biphenyl-4-yl ester (325 mg) was dissolved in dichloromethane (15 mL) and added with TFA. The solution was stirred at room temperature for 7 hrs. Solvent was removed by rotovap and crude product purified by column chromatography (5–20% MeOH/EtOAc) to yield Benzofuran-2-carboxylic acid 4'-(1-carboxy-2-methyl-propylsulfamoyl)-biphenyl-4-yl ester in 76% yield (241 mg).

1H NMR (400 MHz, DMSO-D6) δ ppm 0.80 (d, J=6.57 Hz, 3 H) 0.87 (d, J=6.82 Hz, 3 H) 2.04 (m, 1 H) 3.24 (m, 1 H) 7.43 (t, J=7.58 Hz, 1 H) 7.49 (d, J=8.84 Hz, 2 H) 7.60 (t, J=7.96 Hz, 1 H) 7.70 (d, J=9.85 Hz, 1 H) 7.85 (m, 7 H) 8.08 (s, 1 H)

Examples 8A, 8B, 8C, 8D, 8E, 8F, 8G were made based on Scheme 14.

Example 8A

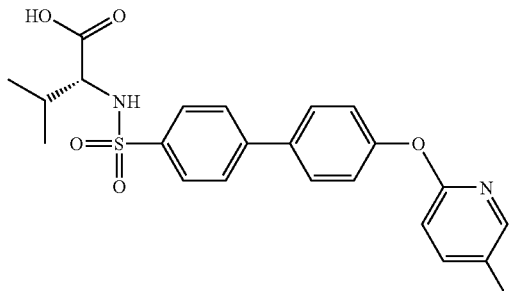

3-Methyl-2-[4'-(5-trifluoromethyl-pyridin-2-yloxy)-biphenyl-4-sulfonylamino]-butyric acid tert-butyl ester Step 14A: 2-(4'-Hydroxy-biphenyl-4-sulfonylamino)-3-methyl-butyric acid tert-butyl ester (100 mg, 0.25 mmol, 1.0 equiv.), 2-Chloro-5-trifluoro methyl pyridine (45.4 mg, 0.25 mmol, 1 equiv.), and $K_2CO_3$ (86.4 mg, 0.63 mmol, 2.5 equiv) were mixed in DMF (8 mL) and heat to 110° C. for 4.5 hr. Reaction was complete as determined by TLC. Then the reaction mixture was cool to room temperature, diluted with EtOAc, washed with brine and dried over $MgSO_4$. After removing solvent, crude product was purified by column chromatography (silica gel, 20% EtOAc/n-Hexane) to afford G9058-109-1 in 74% yield (100 mg).

1H NMR (400 MHz, CHLOROFORM-D) δ ppm 0.80 (d, J=6.82 Hz, 3 H) 0.96 (d, J=6.82 Hz, 3 H) 1.14 (s, 9 H) 2.01 (m, 1 H) 3.61 (m, 1 H) 5.07 (d, J=9.85 Hz, 1 H) 7.03 (d, J=8.59 Hz, 1 H) 7.19 (s, 1 H) 7.21 (s, 1 H) 7.55 (d, J=8.59 Hz, 2 H) 7.62 (d, J=8.59 Hz, 2 H) 7.85 (d, J=2.02 Hz, 2 H) 7.88 (d, J=6.06 Hz, 1 H) 8.40 (s, 1 H).

Step 14B: 3-Methyl-2-[4'-(5-trifluoromethyl-pyridin-2-yloxy)-biphenyl-4-sulfonylamino]-butyric acid tert-butyl ester (97 mg) was dissolved in $CH_2Cl_2$ (6 mL) and added with TFA (2 mL). Reaction was complete in 6 hrs as determined by TLC. After removing solvent, residue was purified by column chromatography (10% MeOH/$CH_2Cl_2$) to afford 3-Methyl-2-[4'-(5-trifluoromethyl-pyridin-2-yloxy)-biphenyl-4-sulfonylamino]-butyric acid in 66% yield (54.5 mg).

1H NMR (400 MHz, MeOD) δ ppm 0.81 (d, J=6.82 Hz, 3 H) 0.88 (d, J=6.82 Hz, 3 H) 1.97 (m, 1 H) 3.55 (d, J=5.31 Hz, 1 H) 7.09 (d, J=8.59 Hz, 1 H) 7.19 (d, J=8.59 Hz, 2 H) 7.68 (dd, J=14.65, 8.59 Hz, 4 H) 7.83 (d, J=8.34 Hz, 2 H) 8.02 (d, J=11.37 Hz, 1 H) 8.35 (d, J=2.53 Hz, 1 H).

Example 8B

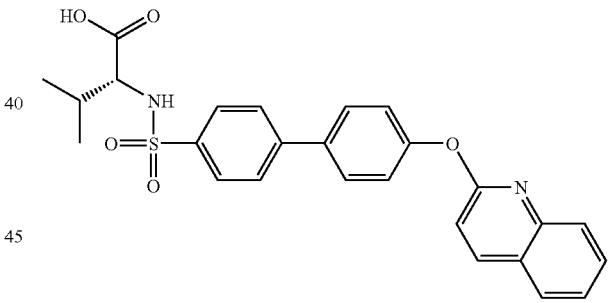

3-Methyl-2-[4'-(quinolin-2-yloxy)-biphenyl-4-sulfonylamino]-butyric acid tert-butyl ester The title compound, 3-Methyl-2-[4'-(quinolin-2-yloxy)-biphenyl-4-sulfonylamino]-butyric acid tert-butyl ester, was prepared according to procedures similar to that of Example 8A.

Step 14A [9058-120-1]: 2-(4'-Hydroxy-biphenyl-4-sulfonylamino)-3-methyl-butyric acid tert-butyl ester (200 mg, 0.49 mmol, 1 equiv.), 2-Chloroquinoline (242 mg, 1.48 mmol, 3 equiv) and $Cs_2CO_3$ (402 mg, 1.235 mmol, 2.5 equiv.) were mixed in DMF (8 mL) and stirred at 100° C. for 7 hrs. Reaction mixture was cool to room temperature then placed in an ice bath and added with water. The solid precipitated from the mixture was collected by filtration and washed with water. After drying, 174 mg of yellow solid was obtained in 66% yield.

1H NMR (400 MHz, CHLOROFORM-D) δ ppm 0.88 (d, J=6.82 Hz, 3 H) 1.03 (d, J=6.82 Hz, 3 H) 1.22 (s, 9 H) 2.07 (m, 1 H) 3.68 (dd, J=9.85, 4.55 Hz, 1 H) 5.15 (d, J=9.85 Hz, 1 H) 7.15 (d, J=8.84 Hz, 1 H) 7.38 (d, J=8.84 Hz, 2 H) 7.45 (m, 1 H) 7.63 (m, 3 H) 7.71 (d, J=8.84 Hz, 2 H) 7.81 (t, J=8.72 Hz, 2 H) 7.91 (d, J=8.59 Hz, 2 H) 8.17 (d, J=8.34 Hz, 1 H).

Step 14B [9058-121-2]: 3-Methyl-2-[4'-(quinolin-2-yloxy)-biphenyl-4-sulfonylamino]-butyric acid tert-butyl ester (164 mg) was dissolved in dichloroethane (12 mL) and hydrolyzed with TFA (4 mL) at room temperature over a period of 4 hrs. Solvent was removed and crude was purified by column chromatography (Eluent 10% MeOH/DCE) to afford 3-Methyl-2-[4'-(quinolin-2-yloxy)-biphenyl-4-sulfonylamino]-butyric acid in 58% yield (84.8 mg).

1H NMR (400 MHz, MeOD) δ ppm 0.82 (d, J=6.82 Hz, 3 H) 0.88 (d, J=6.82 Hz, 3 H) 1.97 (m, 1 H) 3.60 (d, J=5.56 Hz, 1 H) 7.10 (d, J=8.84 Hz, 1 H) 7.25 (d, J=8.84 Hz, 2 H) 7.39 (t, J=6.82 Hz, 1 H) 7.56 (t, J=7.71 Hz, 1 H) 7.63 (d, J=0.51 Hz, 1 H) 7.65 (d, J=1.26 Hz, 1 H) 7.68 (m, 1 H) 7.69 (d, J=2.27 Hz, 1 H) 7.72 (m, 1 H) 7.74 (m, 1 H) 7.79 (dd, J=7.83, 1.26 Hz, 1 H) 7.82 (m, 1 H) 7.85 (m, 1 H) 8.23 (d, J=8.84 Hz, 1 H).

Example 8C

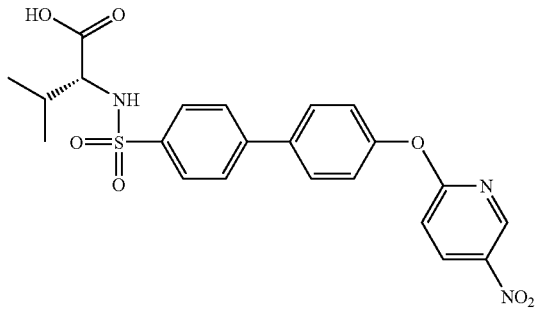

N-({4'-[(5-nitropyridin-2-yl)oxy]-1,1'-biphenyl-4-yl}sulfonyl)-D-valine

The title compound, N-({4'-[(5-nitropyridin-2-yl)oxy]-1,1'-biphenyl-4-yl}sulfonyl)-D-valine , was prepared according to procedures similar to that of Example 8A.

Step 14A and 14B: Yield 60%. 1H NMR (400 MHz, MeOD) δ ppm 0.82 (d, J=6.82 Hz, 3 H) 0.88 (d, J=6.82 Hz, 3 H) 1.96 (m, 1 H) 3.58 (d, J=5.31 Hz, 1 H) 7.11 (d, J=9.09 Hz, 1 H) 7.22 (d, J=8.84 Hz, 2 H) 7.70 (dd, J=11.87, 8.84 Hz, 4 H) 7.83 (d, J=8.59 Hz, 2 H) 8.52 (dd, J=9.09, 2.78 Hz, 1 H) 8.91 (d, J=3.28 Hz, 1 H).

Example 8D

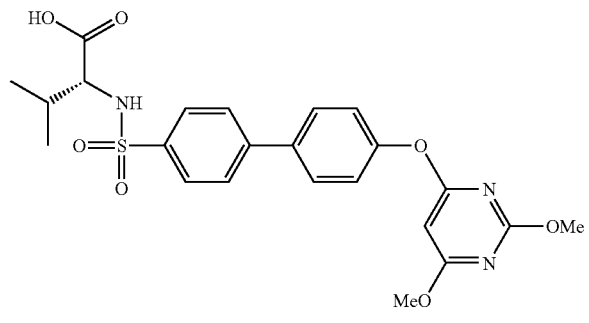

N-({4'-[(2,6-dimethoxypyrimidin-4-yl)oxy]-1,1'-biphenyl-4-yl}sulfonyl)-D-valine

The title compound, N-({4'-[(2,6-dimethoxypyrimidin-4-yl)oxy]-1,1'-biphenyl-4-yl}sulfonyl)-D-valine, was prepared according to procedures similar to that of Example 8A.

Step 14A and 14B: Yield 82%. 1H NMR (400 MHz, MeOD) δ ppm 0.81 (d, J=6.82 Hz, 3 H) 0.88 (d, J=6.82 Hz, 3 H) 1.97 (m, 1 H) 3.56 (d, J=5.31 Hz, 1 H) 3.78 (s, 3 H) 3.85 (s, 3 H) 5.73 (s, 1 H) 7.18 (d, J=8.84 Hz, 2 H) 7.66 (d, J=8.84 Hz, 3 H) 7.70 (d, J=8.84 Hz, 3 H) 7.81 (s, 1 H) 7.83 (s, 1 H).

Example 8E

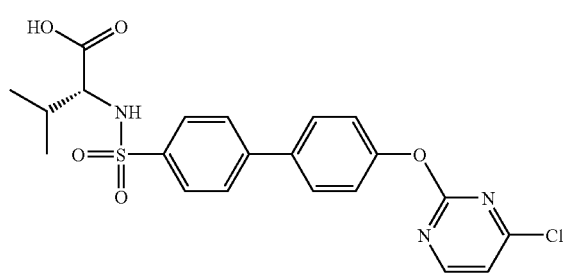

N-({4'-[(4-chloropyrimidin-2-yl)oxy]-1,1'-biphenyl-4-yl}sulfonyl)-D-valine

The title compound, N-({4'-[(4-chloropyrimidin-2-yl)oxy]-1,1'-biphenyl-4-yl}sulfonyl)-D-valine, was prepared according to procedures similar to that of Example 8A.

Step 14A and 14B: Yield 59%. 1H NMR (400 MHz, DMSO-D6) δ ppm 0.80 (d, J=6.82 Hz, 3 H) 0.85 (d, J=6.82 Hz, 3 H) 1.97 (m, 1 H) 3.47 (s, 1 H) 7.24 (d, J=5.81 Hz, 1 H) 7.42 (d, J=8.84 Hz, 2 H) 7.87 (d, 7 H) 8.66 (d, J=5.56 Hz, 1 H).

Example 8F

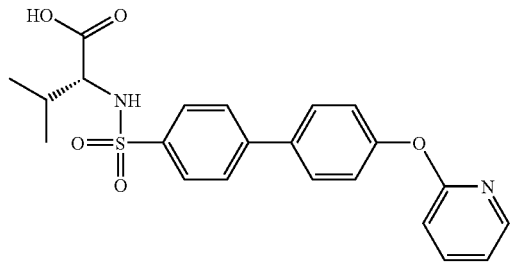

N-{[4'-(pyridin-2-yloxy)-1,1'-biphenyl-4-yl]sulfonyl}-D-valine

The title compound, N-{[4'-(pyridin-2-yloxy)-1,1'-biphenyl-4-yl]sulfonyl}-D-valine, was prepared according to procedures similar to that of Example 8A.

Step 14A and 14B: Yield 83%. 1H NMR (400 MHz, DMSO-D6) δ ppm 0.82 (d, J=6.82 Hz, 3 H) 0.85 (d, J=6.82 Hz, 3 H) 1.85–2.02 (m, 1 H) 3.57 (dd, J=10.48, 4.67 Hz, 1 H) 7.10 (d, J=9.85 Hz, 1 H) 7.17 (dd, J=7.20, 4.93 Hz, 1 H) 7.26 (d, J=8.84 Hz, 2 H) 7.79 (d, J=8.84 Hz, 2 H) 7.82–7.95 (m, 4 H) 8.09 (d, J=9.35 Hz, 1 H) 8.13–8.28 (m, 1 H).

Example 8G

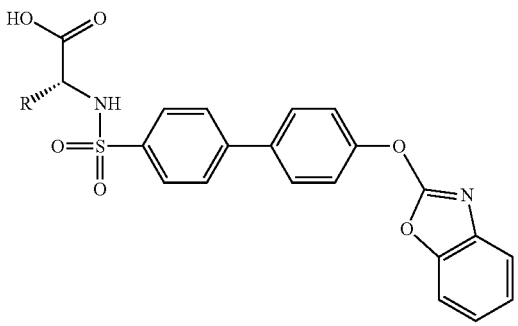

N-{[4'-(1,3-benzoxazol-2-yloxy)-1,1'-biphenyl-4-yl]sulfonyl}-D-valine

The title compound, N-{[4'-(1,3-benzoxazol-2-yloxy)-1,1'-biphenyl-4-yl]sulfonyl}-D-valine, was prepared according to procedures similar to that of Example 8A.

Step 14A and 14B: Yield 85%. 1H NMR (400 MHz, DMSO-D6) δ ppm 0.82 (d, J=6.82 Hz, 3 H) 0.85 (d, J=6.82 Hz, 3 H) 1.86–2.05 (m, 1 H) 3.58 (dd, J=9.22, 5.94 Hz, 1 H) 7.32 (d, J=9.35 Hz, 1 H) 7.53 (d, J=7.33 Hz, 1 H) 7.61–7.73 (m, 3 H) 7.81–7.99 (m, 6 H) 8.10 (d, J=9.35 Hz, 1 H).

Example 9A was made based on Scheme 15.

Example 9A

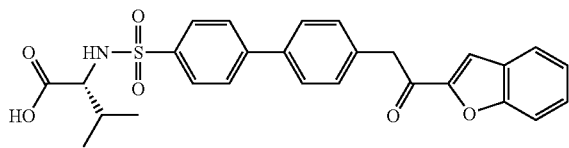

N-({4'-[2-(1-benzofuran-2-yl)-2-oxoethyl]-1,1'-biphenyl-4-yl}sulfonyl)-D-valine

Step 15A: (4-Bromophenyl)-acetic acid (5.0 g, 23.2 mmol, 1 eq.) dissolved in thionyl chloride (50 mL) was heat to reflux for 1 hr. under nitrogen atmosphere. The solution was cool to room temperature and solvent was evaporated. Residue thus obtained was dissolved in anhydrous methylene chloride and used in Step 15B.

Step 15B: Benzofuran-2-yl-trimethyl-silane (3.4 g, 17.86 mmol) was dissolved in methylene chloride (40 mL) and cool to −78° C. 4-Bromophenyl-acetyl chloride (19.65 mmol, 1.1 equiv.) was added at this temperature. Under vigorous stirring, a solution of TiCl₄ (23 mL, 1M, 23.2 mmol, 1.3 equiv.) in CH₂Cl₂ was added dropwise and stirring continued for 20 min. Then the reaction was quenched with H₂O (100 mL), cooling bath was removed and the mixture was allowed to warm up to room temperature. It was then diluted with H₂O (100 mL) and extracted with CH₂Cl₂ (3×). Organic layers were combined, washed with brine, dried over MgSO₄, solvent evaporated. Crude product thus obtained was subject to column purification. (silica gel, 10% EtOAC/Hexane). 980 mg of 1-Benzofuran-2-yl-2-(4-bromo-phenyl)-ethanone was obtained in 17% yield.

1H NMR (400 MHz, CHLOROFORM-D) δ ppm 4.34 (s, 2 H) 7.34 (d, J=8.59 Hz, 2 H) 7.44 (d, 1 H) 7.58 (d, J=8.59 Hz, 2 H) 7.62 (d, J=5.81 Hz, 1 H) 7.67 (s, 1 H) 7.71 (m, 1 H) 7.84 (t, J=6.19 Hz, 1 H).

Step 15C: A solution of 3-Methyl-2-(4-tributylstannanyl-benzenesulfonylamino)-butyric acid tert-butyl ester (347.5 mg, 0.58 mmol, 1.0 equiv.), 1-Benzofuran-2-yl-2-(4-bromophenyl)-ethanone (200 mg, 0.64 mmol, 1.1 equiv.) and Pd(PPh₃)₄ (66 mg, 0.06 mmol, 10%) in anhydrous toluene (10 mL) was heat to reflux for 7 hrs. Reaction was complete as determined by TLC. Solvent was removed by rotovap and crude product purified by column chromatography (silica gel, 20% EtOAc/n-Hexane) to afford 2-[4'-(2-Benzofuran-2-yl-2-oxo-ethyl)-biphenyl-4-sulfonylamino]-3-methyl-butyric acid tert-butyl ester in 20% yield (62 mg).

1H NMR (400 MHz, CHLOROFORM-D) δ ppm 0.79 (d, J=6.82 Hz, 3 H) 0.95 (d, J=6.82 Hz, 3 H) 1.11 (s, 9 H) 3.58 (dd, J=9.85, 4.55 Hz, 1 H) 4.26 (s, 2 H) 5.05 (d, J=9.85 Hz, 1 H) 7.26 (t, J=7.07 Hz, 1 H) 7.43 (m, 5 H) 7.56 (m, 4 H) 7.65 (d, J=7.83 Hz, 1 H) 7.81 (d, J=8.59 Hz, 2 H).

Step 15D: 2-[4'-(2-Benzofuran-2-yl-2-oxo-ethyl)-biphenyl-4-sulfonylamino]-3-methyl-butyric acid tert-butyl ester (62 mg) was dissolved in anhydrous CH₂Cl₂ (6 mL) and added with TFA (2 mL). The reaction mixture was stirred at room temperature for 3 hrs. Solvent was removed, crude product was purified by column chromatography (10% MeOH/CH₂Cl₂) to afford 2-[4'-(2-Benzofuran-2-yl-2-oxo-ethyl)-biphenyl-4-sulfonylamino]-3-methyl-butyric acid in 19% yield (10.7 mg).

1H NMR (400 MHz, DMSO-D6) δ ppm 0.79 (d, J=6.82 Hz, 3 H) 0.84 (m, J=6.82 Hz, 3 H) 1.97 (m, 1 H) 3.33 (s, 1 H) 4.42 (s, 2 H) 7.39 (t, J=7.07 Hz, 1 H) 7.47 (d, J=8.34 Hz, 2 H) 7.57 (t, J=8.59 Hz, 1 H) 7.73 (m, 3 H) 7.83 (d, 4 H) 7.88 (d, J=8.84 Hz, 1 H) 8.13 (s, 1 H) 10.08 (s, 1 H).

Example 10A was made based on Scheme 16.

Example 10A

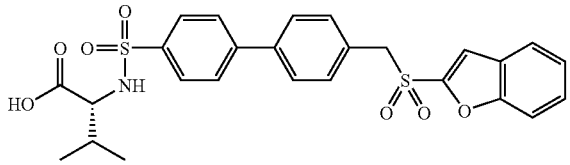

D-2-[4'-(Benzofuran-2-sulfonylmethyl)-biphenyl-4-sulfonylamino]-3-methyl-butyric acid Step 16A: Starting material 2-[1,2,3]Thiadiazol-4-yl-phenol was prepared according to literature procedure (M. A. Abramov, W. Dehaen, B. D'hooge, M. L. Petrov, S. Smeets, S. Toppet and M. Voets Tetrahedron, 2000, 56, 3933–3940). 2-[1,2,3]Thiadiazol-4-yl-phenol (241 mg, 1.35 mmol), 2-(4-Bromomethyl-phenyl)-4,4,5,5-tetramethyl-[1,3,2]dioxaborolane (406 mg, 1.37 mmol, 1 eq), and K₂CO3 (396 mg, 2.87 mmol, 1.9 eq) was mixed in 8 mL of CH3CN and heat to 90° C. under nitrogen atmosphere. After reaction was complete as monitored by TLC, the mixture was cool to room temperature and solvent evaporated. The resulting crude material was subject to column chromatography (20% EtOAc in hexane) to give 2-[4-(4,4,5,5-Tetramethyl-[1,3,2]dioxaborolan-2-yl)-benzylsulfanyl]-benzofuran (198 mg) in 40% yield. NMR: G8475-125. 1H NMR (400 MHz, CHLOROFORM-D) δ ppm 1.3 (s, 12 H)4.1 (s, 2 H) 6.6 (d, J=1.0 Hz, 1 H) 7.2 (m, 4 H) 7.4 (d, J=7.8 Hz, 2 H) 7.7 (d, J=8.1 Hz, 2 H).

Step 16B: Suzuki coupling of D-2-(4-Bromo-benzenesulfonylamino)-3-methyl-butyric acid methyl ester with 2-[4-(4,4,5,5-Tetramethyl-[1,3,2]dioxaborolan-2-yl)-benzylsulfanyl]-benzofuran was carried out according to procedures in Step 5B for Example 2A to give D-2-[4'-(Benzofuran-2-ylsulfanylmethyl)-biphenyl-4-sulfonylamino]-3-methyl-butyric acid methyl ester in 54% yield. NMR:

G8475-165. 1H NMR (400 MHz, BENZENE-D6) δ ppm 0.7 (d, J=6.8 Hz, 3 H) 0.9 (d, J=6.8 Hz, 3 H) 1.9 (m, 1 H) 3.0 (s, 3 H) 4.0 (m, 3 H) 5.0 (d, J=10.1 Hz, 1 H) 6.6 (d, J=1.0 Hz, 1 H) 7.1 (m, 4 H) 7.3 (m, 6 H)7.3 (s, 1 H) 7.4 (m, 1 H).

Step 16C: A solution of D-2-[4'-(Benzofuran-2-ylsulfanylmethyl)-biphenyl-4-sulfonylamino]-3-methyl-butyric acid methyl ester (75 mg, 0.15 mmol, 1 eq) in 4 mL of THF was placed in ice bath. 125 mg of MCPBA (77%, 0.55 mmol, 3.7 eq) in 3 mL of THF was added dropwise. After addition complete, ice bath was removed and the reaction was allowed to warm to room temperature and stir for 12 hrs. TLC indicated reaction was complete. Regular work-up and column chromatography (20% EtOAc in hexane) to afford D-2-[4'-(Benzofuran-2-sulfonylmethyl)-biphenyl-4-sulfonylamino]-3-methyl-butyric acid methyl ester (56 mg) in 70% yield. NMR: G8475-166. 1H NMR (400 MHz, CHLOROFORM-D) □ ppm 0.9 (dd, J=33.3, 6.8 Hz, 6 H) 2.0 (m, 1 H) 3.4 (s, 3 H) 3.8 (dd, J=10.1, 5.3 Hz, 1 H) 4.6 (s, 2 H) 5.1 (d, J=10.1 Hz, 1 H) 7.4 (m, 4 H) 7.5 (m, 3 H) 7.6 (m, 1 H) 7.7 (m, 3 H) 7.9 (d, J=8.8 Hz, 2 H).

Step 16D [: Hydrolysis of D-2-[4'-(Benzofuran-2-sulfonylmethyl)-biphenyl-4-sulfonylamino]-3-methyl-butyric acid methyl ester was carried out according to procedures in Step 1D for Example 1A in quantitative yield. 1H NMR (400 MHz, DMSO-D6) δ ppm 0.8 (dd, J=12.1, 6.8 Hz, 6 H) 1.9 (m, 1 H) 3.5 (dd, J=9.3, 6.1 Hz, 1 H) 5.0 (s, 2 H) 7.4 (d, J=8.3 Hz, 2 H) 7.4 (m, 1 H) 7.6 (m, 1 H) 7.7 (d, J=1.0 Hz, 1 H) 7.7 (d, J=8.3 Hz, 2 H) 7.8 (m, 6 H) 8.1 (d, J=9.1 Hz, 1 H).

The following compounds (11A–11B) were prepared according to Scheme 6B.

Example 11A

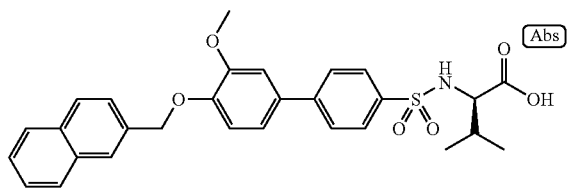

3-Methyl-2-[4'-(naphthalen-2-ylmethoxy)-3'-methoxy-biphenyl-4-sulfonylamino]-butyric acid.

¹H NMR (400 MHz, DMSO): δ 0.806(d, 3H), 0.837(d, 3H), 1.94(m, 1H), 3.53(t, 1H), 3.90(s, 3H), 5.33(s, 2H), 7.20(d, 1H), 7.27(m, 1H), 7.34(s, 1H), 7.54(d, 2H), 7.61(d, 1H), 7.89(m, 8H); ES⁺ m/z 518.2 (M–H); HRMS (C29H29NO6S): calcd; 520.17884. found; 520.17839 (M+H).

Example 11B

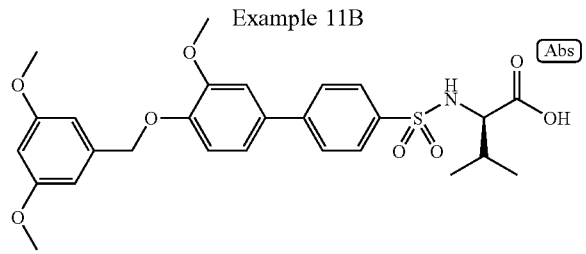

2-[4'-(3,5-Dimethoxy-benzyloxy)-3'-methoxy-biphenyl-4-sulfonylamino]-3-methyl-butyric acid ¹H NMR (400 MHz, DMSO): δ 0.808(d, 3H), 0.838(d, 3H), 1.94(m, 1H), 3.74(s, 6H), 3.89(s, 3H), 5.09(s, 2H), 6.45(t, 1H), 6.62(d, 2H), 7.11(d, 1H), 7.25(d, 1H), 7.32(d, 1H), 7.79(d, 2H), 7.85(d, 2H), 8.02(d, 1H); ES⁺ m/z 528.2 (M–H); HRMS (C27H31NO8S): calcd; 530.18432. found; 530.18367 (M+H).

The following compounds (12A–12R) were made using procedures described in scheme 17.

Example 12A

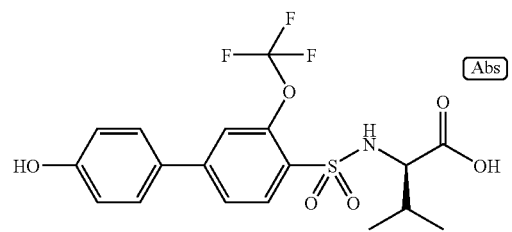

2-(4'-Hydroxy-3-trifluoromethoxy-biphenyl-4-sulfonylamino)-3-methyl-butyric acid ¹H NMR (400 MHz, DMSO): δ0.825(d, 3H), 0.875(d, 3H), 2.04(m, 1H), 3.70(m, 1H), 6.89(d, 2H), 7.59(m, 2H), 7.75(dd, 1H), 7.94(d, 1H), 8.16(d, 1H); ES⁺ m/z 432.1 (M–H); HRMS (C18H18F3NO6S): calcd; 451.11451. found; 451.11461 (M+NH4).

Example 12B

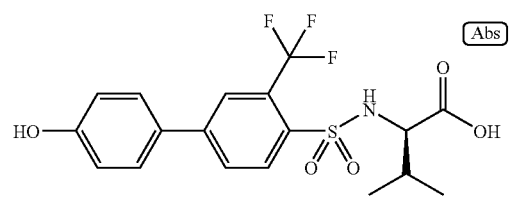

2-(4'-Hydroxy-3-trifluoromethyl-biphenyl-4-sulfonylamino)-3-methyl-butyric acid

¹H NMR (400 MHz, DMSO): δ 0.850(m, 6H), 2.02(m, 1H), 3.60(m, 1H), 6.90(d, 2H), 7.67(d, 2H), 8.10(m, 3H); ES⁺ m/z 416.0 (M–H); HRMS (C18H18F3NO5S): calcd; 435.11960. found; 435.11966 (M+NH4).

Example 12C

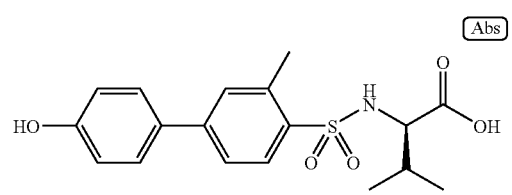

2-(4'-Hydroxy-3-methyl-biphenyl-4-sulfonylamino)-3-methyl-butyric acid

¹H NMR (400 MHz, DMSO): δ 0.810(t, 6H), 1.93(m, 1H), 2.64(s, 3H), 3.39(m, 1H), 6.87(m, 2H), 7.56(m, 3H), 7.81(d, 1H), 8.00(d, 1H); ES⁺ m/z 362.1 (M–H); HRMS (C18H21NO5S): calcd; 381.14786. found; 381.14808 (M+NH4).

Example 12D

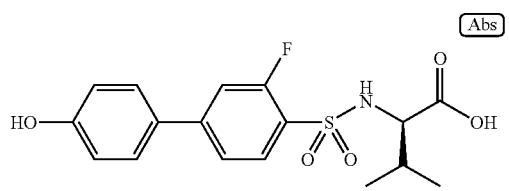

2-(3-Fluoro-4'-hydroxy-biphenyl-4-sulfonylamino)-3-methyl-butyric acid $^1$H NMR (400 MHz, DMSO): δ0.850(m, 6H), 2.02(m, 1H), 3.63(m, 1H), 6.87(d, 2H), 7.61(m, 3H), 7.76(t, 1H), 8.22(d, 1H); ES$^+$ m/z 366.0 (M–H); HRMS (C17H18FNO5S): calcd; 385.12279. found; 385.12276 (M+NH4).

Example 12E

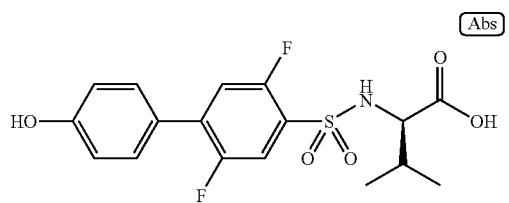

2-(2,5-Difluoro-4'-hydroxy-biphenyl-4-sulfonylamino)-3-methyl-butyric acid $^1$H NMR (400 MHz, DMSO): δ 0.880(m, 6H), 2.04(m, 1H), 3.69(m, 1H), 6.89(d, 1H), 7.45(m, 2H), 7.58(m, 2H), 8.45(d, 1H); ES$^+$ m/z 384.1 (M–H); HRMS (C17H17F2NO5S): calcd; 403.1137. found; 403.11328 (M+NH4).

Example 12F

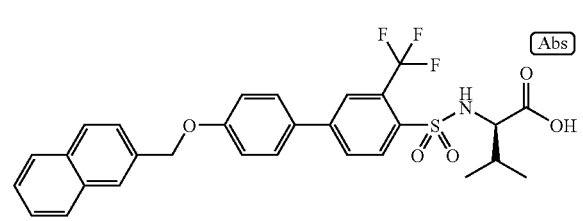

3-Methyl-2-[4'-(naphthalen-2-ylmethoxy)-3-trifluoromethyl-biphenyl-4-sulfonylamino]-butyric acid $^1$H NMR (400 MHz, DMSO): δ 0.900(d, 3H), 0.960(d, 3H), 2.06(m, 1H), 3.70(d, 1H), 4.19(s, 2H), 6.95(d, 1H), 7.43(m, 6H), 7.69(s, 1H), 7.75(m, 3H) 7.88 (m, 1H), 7.97(s, 1H), 8.15(d, 1H); ES$^+$ m/z 556.1 (M–H); HRMS (C29H26F3NO5S): calcd; 558.15566. found; 558.15484 (M+H).

Example 12G

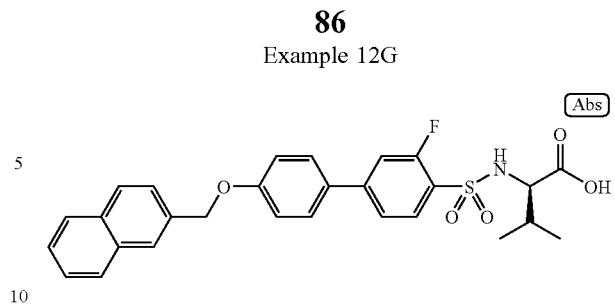

2-[3-Fluoro-4'-(naphthalen-2-ylmethoxy)-biphenyl-4-sulfonylamino]-3-methyl-butyric acid $^1$H NMR (400 MHz, MeOH): δ 0.920(d, 3H), 0.980(d, 3H), 2.10(m, 1H), 3.76(d, 1H), 4.19(s, 2H), 6.94(d, 1H), 7.43(m, 7H), 7.70(s, 1H), 7.78(m, 4H); ES$^+$ m/z 506.1 (M–H); HRMS (C28H26FNO5S): calcd; 508.15885. found; 508.15818 (M+H).

Example 12H

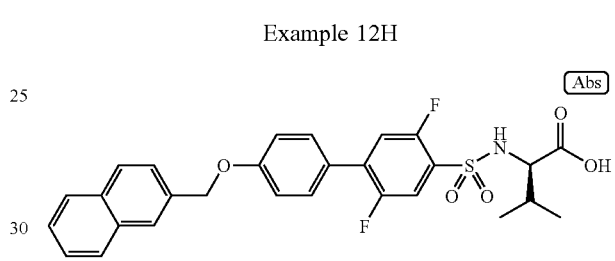

2-[2,5-Difluoro-4'-(naphthalen-2-ylmethoxy)-biphenyl-4-sulfonylamino]-3-methyl-butyric acid $^1$H NMR (400 MHz, MeOH): δ 0.910(d, 3H), 0.980(d, 3H), 2.09(m, 1H), 3.78(d, 1H), 4.16(s, 2H), 6.92(d, 1H), 7.37(m, 6H), 7.56(m, 1H), 7.67(s, 1H), 7.75(m, 4H); ES$^+$ m/z 524.1 (M–H); HRMS (C28H25F2NO5S): calcd; 526.14943. found; 526.14881 (M+H).

Example 12I

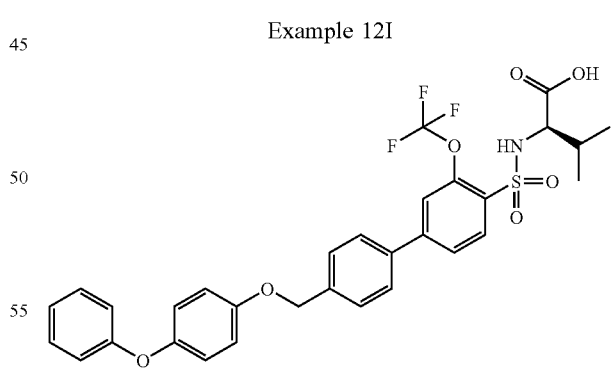

ES$^+$ m/z 614.1 (M–H)–HRMS: 616.16053 (M+H)+; 616.16114 Calc'd H NMR (400 MHz, DMSO): δ 0.83 (d, 3H, J=6.8 Hz), 0.088 (d, 3H, J=6.8 Hz), 2.06 (m, 1H), 3.74 (dd, 1H, J=5.6, 10 Hz), 5.18 (s, 2H), 5.35 (d, 1H, J=10 Hz), 6.92 (d, 2H, J=8 Hz), 7.00 (d, 2H, J=8 Hz), 7.07 (d, 2H, J=8 Hz), 7.34 (d, 2H, J=8 Hz), 7.61 (d, 2H, J=8 Hz), 7.69 (s, 1H), 7.79 (d, 2H, J=8 Hz), 7.88 (m, 1H), 8.02 (d, 1H, J=8 Hz), 8.24 (m, 1H), 12.70 (s, 1H).

87

Example 12J

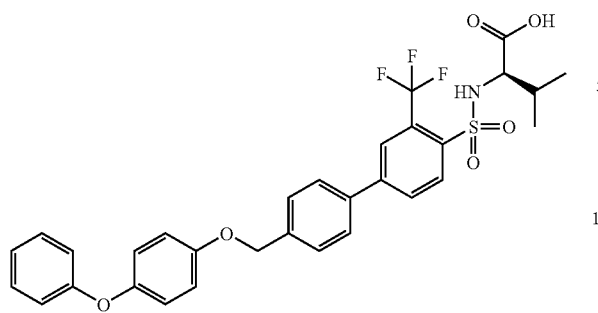

ES+ m/z 598.1 (M−H)−HRMS: 600.16554 (M+H)+; 600.16622 Calc'd H NMR (400 MHz, DMSO): δ 0.85 (d, 3H, J=6.8 Hz), 0.86 (d, 3H, J=6.8 Hz), 2.05 (m,

Example 12K

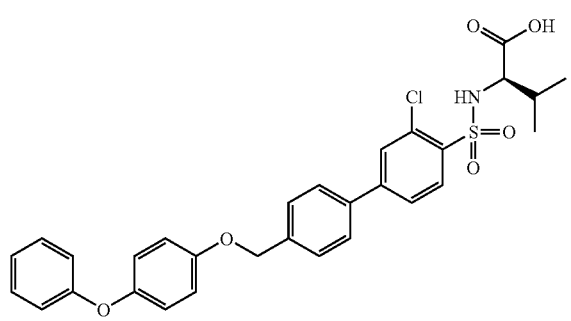

ES+ m/z 564.1 (M−H)−HRMS: 566.13860 (M+H)+; 566.13987 Calc'd H NMR (400 MHz, DMSO): δ 0.84 (d, 3H, J=6.8 Hz), 0.86 (d, 3H, J=6.8 Hz), 2.02 (m, 1H), 3.57 (dd, 1H, J=6, 9.2 Hz), 5.17 (s, 2H), 6.92 (d, 2H, J=8 Hz), 6.99 (d, 2H, J=8 Hz), 7.07 (m, 3H), 7.33 (m, 2H), 7.59 (d, 2H, J=8 Hz), 7.83 (m, 5H), 7.95 (d, 1H, J=1.6 Hz), 8.03 (d, 1H, J=8 Hz), 8.21 (m, 1H), 12.65 (s, 1H).

Example 12L

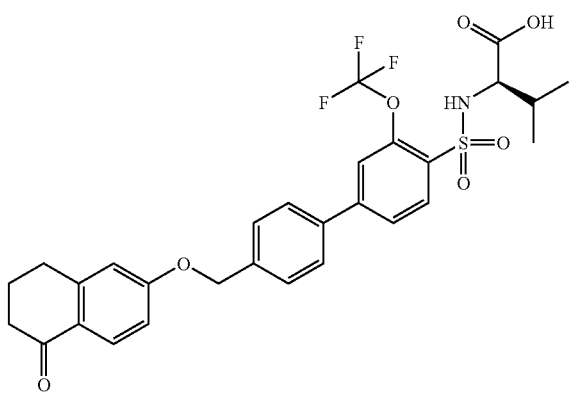

ES+ m/z 590.1 (M−H)−HRMS: 592.16098 (M+H)+; 592.16114 Calc'd ¹H NMR (400 MHz, DMSO): δ 0.83 (d, 3H, J=6.8 Hz), 0.88 (d, 3H, J=6.8 Hz), 2.05 (m, 3H), 2.53 (t, 2H, J=6 Hz), 2.91 (t, 2H, J=6 Hz), 3.74 (dd, 1H, J=5.6, 10 Hz), 5.28 (s, 2H), 6.98 (m, 2H), 7.60 (d, 2H, J=8 Hz), 7.69 (s, 1H), 7.85 (m, 4H), 8.02 (d, 1H, J=8 Hz), 8.25 (d, 1H, J=8 Hz), 12.70 (s, 1H).

88

Example 12M

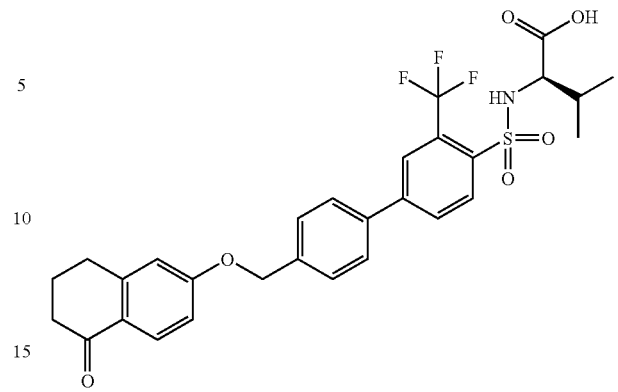

ES+ m/z 574.1 (M−H)−HRMS: 576.16522 (M+H)+; 576.16622 Calc'd ¹H NMR (400 MHz, DMSO): δ 0.85 (d, 3H, J=6.8 Hz), 0.86 (d, 3H, J=6.8 Hz), 2.04 (m, 3H), 2.53 (t, 2H, J=6 Hz), 2.91 (t, 2H, J=6 Hz), 3.63 (dd, 1H, J=6, 10 Hz), 5.29 (s, 2H), 6.98 (m, 2H), 7.61 (d, 2H, J=8 Hz), 7.85 (m, 3H), 8.20 (m, 4H), 12.70 (s, 1H).

Example 12N

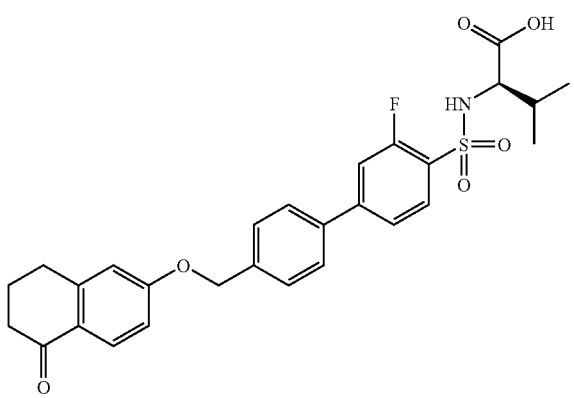

ES+ m/z 524.1 (M−H)−HRMS: 526.16859 (M+H)+; 526.16942 Calc'd ¹H NMR (400 MHz, DMSO): δ 0.84 (d, 3H, J=6.8 Hz), 0.87 (d, 3H, J=6.8 Hz), 2.02 (m, 3H), 2.53 (t, 2H, J=6 Hz), 2.91 (t, 2H, J=6 Hz), 3.66 (dd, 1H, J=6, 9.2 Hz), 5.27 (s, 2H), 6.98 (m, 2H), 7.58 (d, 2H, J=8 Hz), 7.70 (m, 1H), 7.83 (m, 5H), 8.30 (d, 1H, J=10 Hz), 12.65 (s, 1H).

Example 12O

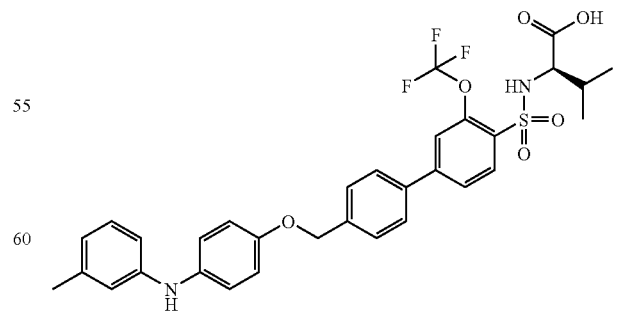

ES+ m/z 629.2 (M−H)−HRMS: 631.17159 (M+H)+; 631.17204 Calc'd ¹H NMR (400 MHz, DMSO): δ 0.83 (d, 3H, J=6.8 Hz), 0.88 (d, 3H, J=6.8 Hz), 2.07 (m, 1H), 2.30

(s, 3H), 3.74 (dd, 1H, J=5.6, 9.6 Hz), 5.20 (s, 2H), 6.68 (d, 1H, J=8 Hz), 6.95 (d, 1H, J=8 Hz), 7.06 (m, 4H), 7.62 (d, 2H, J=8 Hz), 7.69 (m, 2H), 7.80 (d, 2H, J=8 Hz), 7.87 (dd, 1H, J=1.6, 8 Hz), 8.03 (d, 1H, J=8 Hz), 8.25 (d, 2H, J=9.2 Hz), 12.70 (s, 1H).

Example 12P

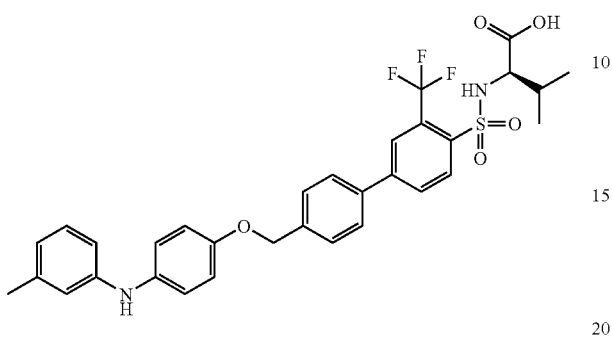

ES+ m/z 613.2 (M–H)–HRMS: 615.17639 (M+H)+; 615.17712 Calc'd $^1$H NMR (400 MHz, DMSO): δ 0.85 (d, 3H, J=6.8 Hz), 0.87 (d, 3H, J=6.8 Hz), 2.05 (m, 1H), 2.30 (s, 3H), 3.63 (dd, 1H, J=6, 9.6 Hz), 5.20 (s, 2H), 6.68 (d, 1H, J=8 Hz), 6.95 (d, 1H, J=8 Hz), 7.06 (m, 4H), 7.63 (d, 2H, J=8 Hz), 7.69 (t, 1H, J=8 Hz), 7.87 (d, 2H, J=8 Hz), 8.21 (m, 4H), 12.70 (s, 1H).

Example 12Q

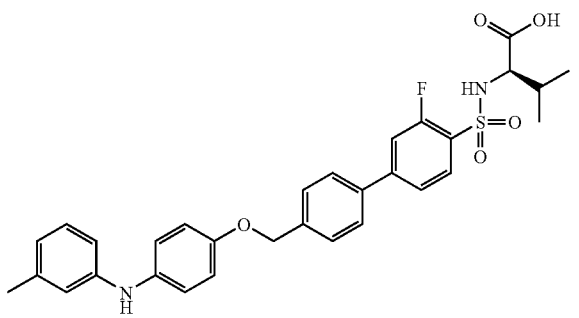

ES+ m/z 563.2 (M–H)–HRMS: 565.18038 (M+H)+; 565.18032 Calc'd $^1$H NMR (400 MHz, DMSO): δ 0.84 (d, 3H, J=6.8 Hz), 0.87 (d, 3H, J=6.8 Hz), 2.04 (m, 1H), 2.30 (s, 3H), 3.66 (dd, 1H, J=6, 9.6 Hz), 5.19 (s, 2H), 6.68 (d, 1H, J=8 Hz), 6.95 (d, 1H, J=8 Hz), 7.06 (s, 4H), 7.60 (d, 2H, J=8 Hz), 7.70 (m, 2H), 7.83 (m, 4H), 8.31 (d, 1H, J=9.2 Hz), 12.70 (s, 1H).

Example 12R

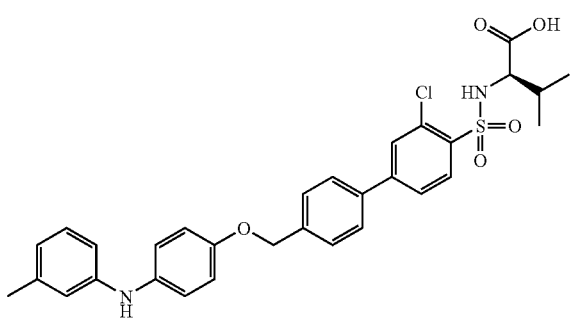

ES+ m/z 579.1 (M–H)–HRMS: 581.15050 (M+H)+; 581.15077 Calc'd $^1$H NMR (400 MHz, DMSO): δ0.84 (d, 3H, J=6.8 Hz), 0.86 (d, 3H, J=6.8 Hz), 2.02 (m, 1H), 2.30 (s, 3H), 3.58 (dd, 1H, J=6.4, 9.6 Hz), 5.20 (s, 2H), 6.68 (d, 1H, J=8 Hz), 6.95 (d, 1H, J=8 Hz), 7.06 (s, 4H), 7.60 (d, 2H, J=8 Hz), 7.62 (d, 2H, J=8 Hz), 7.83 (m, 3H), 7.95 (d, 1H, J=1.6), 8.03 (d, 1H, J=8 Hz), 8.22 (d, 1H, J=9.6 Hz), 12.70 (s, 1H).

Examples 13A, 13B, 13C were made based on Scheme 5.

Example 13A

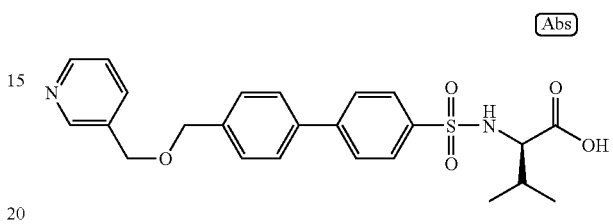

3-Methyl-2-[4'-(pyridin-3-ylmethoxymethyl)-biphenyl-4-sulfonylamino]-butyric acid $^1$H NMR (400 MHz, MeOD): δ; ES+ m/z (M+H) 455.1; HRMS (M+H) m/z calcd 455.16352. found 455.16317; ($C_{24}H_{26}N_2O_5S$):

Example 13B

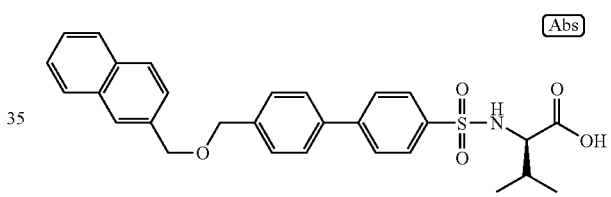

3-Methyl-2-[4'-(naphthalen-2-ylmethoxymethyl)-biphenyl-4-sulfonylamino]-butyric acid $^1$H NMR (400 MHz CDCl$_3$): δ0.85 (d, 3H), 0.95 (d, 3H),2.10 (m, 1H), 3.83 (m, 1H), 4.63 (s, 2H), 4.74 (s, 2H), 5.25 (bs, 1H), 7.44–7.55 (m, 7H), 7.65 (d, 2H), 7.82–7.90 (m, 6H); ES+ m/z (M–H) 502.1; HRMS (M+H) m/z calcd 504.18392. found 504.18503; ($C_{29}H_{29}NO_5S$):

Example 13C

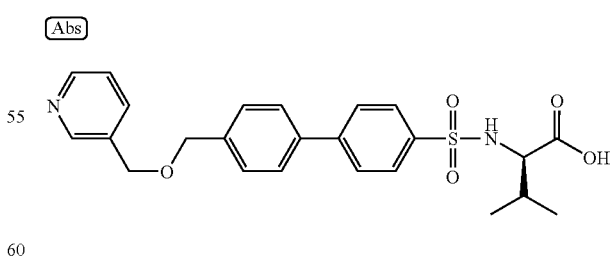

3-Methyl-2-[4'-(pyridin-3-ylmethoxymethyl)-biphenyl-4-sulfonylamino]-butyric acid $^1$H NMR (400 MHz, DMSO): δ 0.81 (d, 3H), 0.84 (d, 3H), 1.95 (m, 1H), 3.55 (dd, 1H), 4.56 (s, 2H), 4.63 (d, 2H), 7.44 (d, 2H), 7.50 (d, 1H), 7.70 (d, 2H), 7.74 (d, 1H), 7.84 (m, 4H), 8.08 (m, 2H); ES+ m/z (M+H) 455.1; HRMS (M+H) m/z calcd 455.16352. found 455.16290; ($C_{24}H_{26}N_2O_5S$)

Example 14

Activity

Aggrecanase-1 FRET Assay

The following protocol was used:

Fluorimeter was started and temperature set to 30° C., about 30 min before setting up the assay. The following reagents are used:

Buffer: 50 mM HEPES, pH 7.5, 100 mM NaCl, 5 mM $CaCl_2$, 0.1% CHAPS, 5% glycerol.

rAggl: 5 µg/ml (final concentration in the assay):

Substrate: Abz-TEGARGSVI-Dap(Dnp) (Abz:o-aminobenzoyl; Dnp: 2,4 dinitrophenyl) (Anaspec Inc), stored at 4° C.). Make a stock at 2 mg/ml in 100% DMSO. Measure the absorbance at 354 nm ($\epsilon=18172$ $M^{-1}$ $cm^{-1}$) to determine the exact concentration. Dilute to 62.5 µM in buffer. Store unused 100% DMSO stock at −80° C. Final concentration of substrate in the assay is 25 µM. This concentration is much less than the $K_m$ ($K_m=1.1+/-0.2$ mM as determined by Jin and Cowling)

Inhibitors. Make up inhibitors at 10× starting concentration in 100% DMSO. Perform serial dilutions (in duplicate) across the nunc plate in 100% DMSO;

Dilution plates: Nunc, polypropylene low binding (Nalgene)

Assay plate: Fluoronunc (Nalgene)

Fluorimeter: GeminiXS (Molecular Devices).

The assay is performed as follows (The plates are set up so that the final column (12) is used for controls. Total reaction volume is 100 µl. Each compound is assayed in duplicate, so 4 compounds are screened per plate):

1) Add buffer to the entire 96-well plate (30 µl/well).
2) Dilute rAgg1 to 25 µg/ml buffer just prior to addition on the plate. Add 20 µl/well to all wells. Mix 6 times.
3) Add 10 µl/well of 10× inhibitors from the working plate, except column 12. Mix 6 times. To wells 12A–F, add 10× controls (see reference compounds below).
4) To wells 12G–H add 10 µl 100% DMSO.
5) Incubate for 10–15 min at 30° C.
6) Add 40 µl/well of 62.5 µM substrate. Mix 6 times.

The reaction is monitored for 30–40 min at 30° C. λex: 340 nm and λem: 420 nm). The fluorescence is linear during this time and the slope of the line (Vmax/sec) represents the initial reaction rate, υ. The maximal rate of cleavage of substrate is determined in the absence of inhibitor.

The percent inhibition of activity in the presence of inhibitor is calculated as follows:

% inhibition=(1−υ(Rate, RFU/sec)/Maximal Rate (RFU/sec))*100

The IC50 was obtained by fitting the initial rate, υ, or % inhibition at each concentration of inhibitor to the following equation in Excel.

y=(a−d)/(1+C/IC$_{50}$)^n)+d

This model describes a sigmoidal curve with an adjustable baseline, a. y is the % inhibition or initial rate of reaction, C is the concentration of inhibitor under test. a is the limiting response as C approaches zero. As C increases without bound y tends toward its lower limit, d. y is halfway between the lower and upper asymptotes when C=IC$_{50}$. n is the Hill coefficient. The sign of n is positive when the response increases with increasing dose and is negative when the response decreases with increasing dose (inhibition).

Table 1 lists the activities for selected compounds of the Examples.

TABLE 1

| Example | IC50 (µM) |
|---------|-----------|
| 1A | 0.2 |
| 1B | 0.8 |
| 1C | 0.2 |
| 1D | 0.4 |
| 1E | 0.6 |
| 1F | 1.5 |
| 1H | 0.23 |
| 2A | 1.0 |
| 2B | 1.5 |
| 2C | 0.8 |
| 2D | 5.5 |
| 2K | 0.5 |
| 3A | 0.35 |
| 4A | 1.2 |
| 5A | 0.4 |
| 6A | 3.6 |
| 6B | 0.6 |
| 6C | 1.1 |
| 6S | 4.5 |
| 7A | 0.09 |
| 7B | 0.345 |
| 11A | 8.9 |
| 11B | 16.7 |
| 12A | 200 |
| 12B | 67 |

The disclosures of each patent, patent application, and publication cited or described in this document are hereby incorporated herein by reference, in their entireties.

Various modifications of the invention, in addition to those described herein, will be apparent to those skilled in the art from the foregoing description. Such modifications are also intended to fall within the scope of the appended claims.

What is claimed:

1. A compound the formula I:

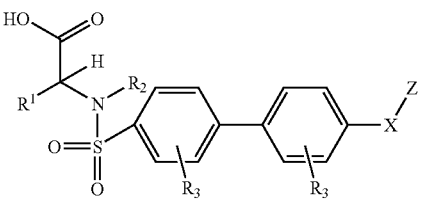

I wherein:

R$^1$ is H or C1–C6 alkyl;

R$^2$ is H, C1–C6 alkyl, (CH$_2$)$_n$R$^{2'}$, phenyl, or benzyl;

n is 0–6;

R$^{2'}$ is aryl, heteroaryl, cycloalkyl, or heterocycloalkyl;

R$^3$ is, independently with respect to each occurrence, H, halogen, OC(halogen)$_3$, C(halogen)$_3$, alkoxy, or C1–C6 alkyl;

X is selected from CH$_2$O, OCH$_2$, C(R$^3$)=C(R$^3$), C(R$^3$)$_2$—C(R$^3$)$_2$, CH$_2$NHC(=O), O(C=O)NH, O, C(=O)CH$_2$, SO$_2$CH$_2$C(=O)NH, SO$_2$NH, OC(=O), CH$_2$S(O), and CH$_2$S(O)$_2$; and Z is at least one aryl or heteroaryl moiety.

2. The compound of claim 1 wherein Z is pyridine, pyrimidine, pyrazine, pyridazine, phenyl, naphthalene, furan, thiophene, pyrrole, pyrazole, imidazole, oxazole, isoxazole, thiazole, benzothiazole, quinoline, or isoquinoline, or

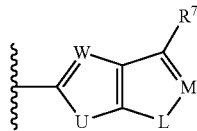

wherein:
U is selected from S, O, C($R^3$)=C($R^3$), C($R^3$)=N, and N($R^4$);
W is selected from C($R^3$), and N;
M is selected from C($R^3$), and N;
L is selected from S, O, C($R^3$)=C($R^3$), C($R^3$)=N, and N($R^4$);
$R^4$ and $R^5$ are, independently with respect to each occurrence, a bond to the other, H, C1–C6 alkyl, or phenyl; and
$R^7$ is selected from a bond to $R^3$, H, halogen, C(halogen)$_3$, $NR^4R^5$, $N[(CH_2)_2]_2O$, $N[(CH_2)_2]_2NR^4$, $NHSO_2R^4$, $NR^4C(=O)R^5$, $NHC(=O)OR^4$, $NO_2$, $SO_2NR^4R^5$, $SO_2R^4$, $OR^4$, $C(=O)R^4$, $COOR^4$, $CONR^4R^5$, CN, phenyl, heteroaryl, C1–C6 alkyl, C2–C6 alkenyl, or C2–C6 alkynyl.

3. The compound of claim 2 wherein $R^7$ is substituted with $NR^4R^5$, $N[(CH_2)_2]_2O$, $N[(CH_2)_2]_2NR^4$, $NHSO_2R^4$, $NR^4C(=O)R^5$, $NHC(=O)OR^4$, $NO_2$, $SO_2NR^4R^5$, $SO_2R^4$, $OR^8$, $C(=O)R^4$, $COOR^4$, $CONR^4R^5$, CN, phenyl, or heteroaryl, wherein $R^8$ is selected from H, phenyl, heteroaryl, and C1–C6 alkyl.

4. The compound of claim 3 wherein $R^8$ is substituted with $NR^4R^5$, $N[(CH_2)_2]_2O$, $N[(CH_2)_2]_2NR^4$, $NR^4SO_2R^5$, $NR^4C(=O)R^5$, $NHC(=O)OR^4$, $NO_2$, $SO_2NR^4R^5$, $SO_2R^4$, $C(=O)R^4$, $COOR^4$, $CONR^4R^5$, CN, phenyl, or heteroaryl.

5. The compound of claim 1 wherein $R^1$ is H or branched alkyl.

6. The compound of claim 1 wherein $R^1$ is isopropyl.

7. The compound of claim 1 wherein $R^3$ is halogen, $CF_3$, $OCH_3$, or $CH_3$.

8. The compound of claim 1 wherein X is $CH_2O$, $OCH_2$, C($R^3$)=C($R^3$), or $CH_2NHC(=O)$.

9. The compound of claim 2 wherein $R^7$ is $CH_3$, ethyl, isopropyl, $CF_3$, CN, or $OCH_3$.

10. The compound of claim 3 wherein $R^8$ is CH3, phenyl, and benzyl.

11. The compound of claim 1 wherein Z is bicyclic.

* * * * *